United States Patent [19]

Eggler et al.

[11] Patent Number: 4,576,964
[45] Date of Patent: Mar. 18, 1986

[54] SUBSTITUTED HEXAHYDROBENZO[E]INDENE AND OCTAHYDROPHENANTHRENE CNS AGENTS AND PHARMACEUTICAL COMPOSITIONS THEREOF

[75] Inventors: James F. Eggler, Stonington; Michael R. Johnson, Gales Ferry; Lawrence S. Melvin, Jr., Ledyard, all of Conn.

[73] Assignee: Pfizer Inc., New York, N.Y.

[21] Appl. No.: 618,151

[22] Filed: Jun. 7, 1984

Related U.S. Application Data

[62] Division of Ser. No. 358,569, Mar. 16, 1982, Pat. No. 4,476,131.

[51] Int. Cl.$^4$ .................. A61K 31/22; C07C 43/10; C07C 43/205
[52] U.S. Cl. .................. 514/546; 514/548; 514/680; 514/719; 514/732; 568/326; 568/633; 568/660; 568/733; 560/139; 560/255
[58] Field of Search .............. 568/633, 326, 733, 660; 560/139, 255; 514/719, 732, 680, 546, 548

[56] References Cited

U.S. PATENT DOCUMENTS 4,188,495  2/1980  Althuis et al. .................. 568/633
4,476,131  10/1984 Eggler et al. .................. 568/633 X Primary Examiner—Bernard Helfin
Attorney, Agent, or Firm—Charles J. Knuth; Albert E. Frost; Paul D. Thomas

[57] ABSTRACT

Tricyclic benzo fused compounds of the formula

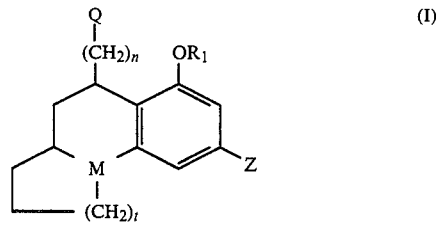

and pharmaceutically acceptable cationic and acid addition salts thereof, wherein n is zero, 1 or 2, and t is 1 or 2; M is CH or N, $R_1$ is H or certain acyl groups; Q is $CO_2R_4$, $COR_5$, $C(OR_7)R_5R_6$, CN, $CONR_9R_{10}$, $CH_2NR_9R_{10}$, $CH_2NHCOR_{11}$, $CH_2NHSO_2R_{12}$, 5-tetrazolyl or when n is 1, Q and $OR_1$ together form a lactone or certain reduced derivatives thereof; and Z is certain alkyl, alkoxy, alkoxyalkyl, aralkyl, aralkoxy, aryloxyalkyl or aralkoxyalkyl groups, are valuable central nervous system active agents, methods for their use, pharmaceutical compositions containing them and certain intermediates therefor.

15 Claims, No Drawings

SUBSTITUTED HEXAHYDROBENZO[E]INDENE AND OCTAHYDROPHENANTHRENE CNS AGENTS AND PHARMACEUTICAL COMPOSITIONS THEREOF

CROSS REFERENCE TO RELATED APPLICATIONS

This is a division of application Ser. No. 358,569 filed Mar. 16, 1982, and now U.S. Pat. No. 4,476,131.

BACKGROUND OF THE INVENTION

1. Field of the Invention

The invention relates to certain novel tricyclic benzo fused compounds, more particularly to certain hexahydropyrrolo[1,2-a]quinoline, hexahydro-1H-pyrido[1,2-a]quinoline, hexahydrobenzo[e]indene and octahydrophenanthrene compounds of the formula

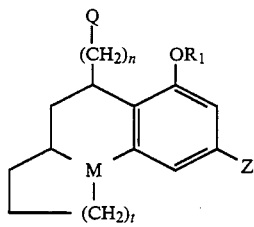

and pharmaceutically acceptable cationic and acid addition salts thereof, useful as CNS agents, especially as analgesic and antiemetic agents for use in mammals, including man; methods for their use, pharmaceutical compositions containing them and intermediates therefor.

2. Description of the Prior Art

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesics such as d-propoxyphene, codeine, and morphine, possess addictive liability. The need for improved and potent analgesics is, therefore, evident.

U.S. Pat. No. 4,188,495 discloses analgesic 1,9-dihydroxyoctahydrophenanthrenes, 1-hydroxyoctahydrophenanthren-9-ones and derivatives thereof which are prepared from intermediates of the formula

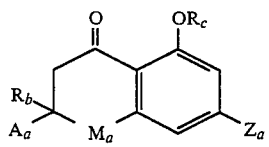

where $M_a$ is $CH_2$, $R_a$ and $R_b$ are certain alkyl and aralkyl groups and $R_c$ and $Z_a$ have many of the values given herein for $R_1$ and $Z$, respectively.

U.S. Pat. No. 4,260,764 discloses compounds of the above formula wherein $M_a$ is $NR_d$ where $R_d$ is a H or certain alkyl, aralkyl, carboxy substituted alkyl or acyl groups, and $R_a$, $R_b$, $R_c$ and $Z_a$ are as defined above.

Copending U.S. patent application, Ser. No. 358,765 filed concurrently herewith, discloses various substituted dodecahydrotriphenylenes, decahydro-1H-cyclopenta[1]phenanthrenes, decahydro-1H-pyrido[1,2-f]phenanthridines and decahydropyrrolo[1,2-f]phenanthridines having activity as CNS agents.

The nomenclature employed herein is based on Rigaudy and Klesney, I.U.P.A.C. Nomenclature of Organic Chemistry—1979 Edition, Permangon Press, New York, including the use of R and S to designate absolute stereochemistry and R* and S* to designate relative stereochemistry. Formulae showing dotted and heavy bonds are generally intended to specify relative stereochemistry, unless otherwise specified in the text.

SUMMARY OF THE INVENTION

It has now been found that certain hexahydropyrrolo[1,2-a]quinoline, hexhydro-1H-pyrido[1,2-a]-quinoline, hexahydrobenz[e]indene and octahydrophenanthrene compounds are useful in mammals as tranquilizers, anticonvulsants, diuretics, antidiarrheals, antitussives and as agents for treatment of glaucoma. They are particularly effective in mammals, including man, as analgesics and as agents for treatment and prevention of emesis and nausea, especially that induced by antineoplastic drugs. Said invention compounds, which are nonnarcotic and free of addiction liability, are of the formula

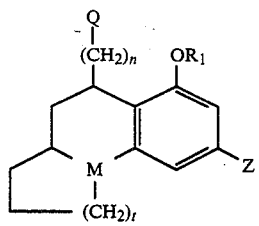

and pharmaceutically acceptable cationic and acid addition salts thereof, wherein n is 0, 1 or 2 and t is 1 or 2, M is CH or N, $R_1$ is H, benzyl, benzoyl, ($C_1$–$C_5$)-alkanoyl or —$CO(CH_2)_pNR_2R_3$ where p is an integer from 1 to 4, each of $R_2$ and $R_3$ is H or ($C_1$–$C_4$) alkyl or when taken together with the nitrogen atom to which they are attached, $R_2$ and $R_3$ are piperidino, pyrrolo, pyrrolidino, morpholino or alkylpiperazio having from one to four carbon atoms in the alkyl group;

Q is $CO_2R_4$, $COR_5$, $C(OR^7)R_5R_6$, CN, $CONR_9R_{10}$, $CH_2NR_9R_{10}$, $CH_2NHCOR_{11}$, $CH_2NHSO_2R_{12}$ or 5-tetrazolyl, and when n is 1 and Q and $OR_1$ are taken together, they form

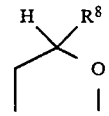

where $R_8$ is H, OH or ($C_1$–$C_4$)alkoxy;

$R_4$ is H, ($C_1$–$C_4$)alkyl or benzyl;

$R_5$ and $R_6$ are each H, ($C_1$–$C_4$) alkyl, phenyl or benzyl;

$R_7$ is H or ($C_2$–$C_4$) alkanoyl;

each of $R_9$ and $R_{10}$ where taken individually is H, ($C_1$–$C_6$)alkyl, phenyl or benzyl, $R_9$ and $R_{10}$ taken together with the nitrogen to which they are attached are piperidino, pyrrolidino, morpholino, or N-alkylpiperazino having from one to four carbon atoms in the alkyl group;

$R_{11}$ is $(C_1-C_5)$alkyl, phenyl, tolyl, benzyl, trifluoromethyl, furyl, thienyl or pyridyl;

$R_{12}$ is $(C_1-C_6)$alkyl, phenyl, tolyl or benzyl;

Z is $(C_5-C_{13})$alkyl, $(C_5-C_{13})$alkoxy, $(C_5-C_{13})$-alkoxyalkyl, $(C_8-C_{13})$pyridylalkyl, $(C_8-C_{13})$pyridyloxyalkyl, $(C_8-C_{13})$pyridylalkoxy, $(C_8-C_{13})$pyridylalkoxyalkyl, $(C_9-C_{14})$phenylalkyl, $(C_9-C_{14})$phenoxyalkyl, $(C_9-C_{14})$phenylalkoxy or $(C_9-C_{14})$-phenylalkoxyalkyl, wherein said phenyl groups are optionally substituted by chloro or fluoro; a pharmaceutically acceptable addition salt thereof when M is N, $R_1$ is $-CO(CH_2)_pNR_2R_3$, Q is $CH_2NR_9R_{10}$, or when Z contains a pyridyl group; or a pharmaceutically acceptable cationic salt thereof when Q is COOH.

Here and elsewhere in this application, the bracketed ranges of carbon atoms are intended to encompass the range of carbon atoms of the entire group which follows. For example $(C_1-C_5)$alkanoyl encompasses HCO— to $C_4H_9CO$—, while $(C_9-C_{14})$phenylalkyl encompasses $(C_6H_5)C_3H_6$— to $(C_6H_5)C_8H_{16}$—.

Compounds of the present invention having particular utility as intermediates are of the formulae

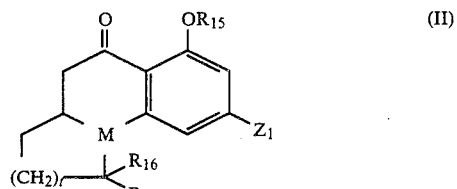

(II)

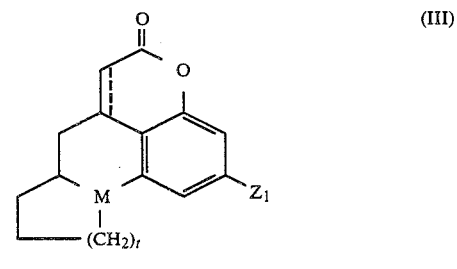

(III)

and

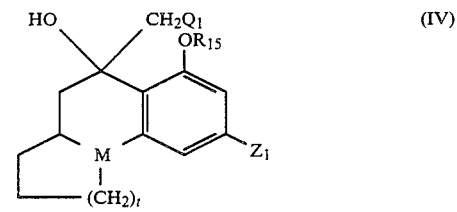

(IV)

where t and M are as defined above, the broken line is a bond or no bond, $R_{15}$ is H, $(C_1-C_4)$alkyl or benzyl; when M is N, $R_{16}$ and $R_{17}$ are each hydrogen or taken together they form =O (a carbonyl oxygen atom), and when M is CH, $R_{16}$ and $R_{17}$ are each H;

$Q_1$ is CN or $COOR_4$; and $Z_1$ is OH, benzyloxy, $(C_1-C_{13})$alkoxy, $(C_5-C_{13})$-alkyl, $(C_5-C_{13})$alkoxyalkyl, $(C_8-C_{13})$pyridylalkyl, $(C_8-C_{13})$pyridylalkoxy, $(C_8-C_{13})$pyridylalkoxyalkyl, $(C_9-C_{14})$phenylalkyl, $(C_9-C_{14})$phenoxyalkyl, $(C_9-C_{14})$-phenylalkoxy or $(C_9-C_{14})$phenylalkoxyalkyl.

Particularly preferred compounds of formula (I) are those wherein:

$R_1$ is H or acetyl, n is 1,

Q is $COOR_4$, especially those where $R_4$ is H, $CH_3$ or $C_2H_5$; $CH_2OR_7$, especially where $R_7$ is H or acetyl; CN, $CH_2NH_2$, $CONH_2$, $CH_2NHCOR_{11}$ or $CH_2NHSO_2R_{12}$;

Z is $(C_5-C_{13})$alkyl, especially $C(CH_3)_2(CH_2)_5CH_3$; $(C_5-C_{13})$alkoxy, especially $OCH(CH_3)(CH_2)_4CH_3$; $(C_5-C_{13})$-alkoxyalkyl, $(C_9-C_{14})$phenylalkyl, or $(C_9-C_{14})$phenylalkoxy, especially $OCH(CH_3)(CH_2)_3C_6H_5$. A more especially preferred value of Z is 5-phenyl-2-pentyloxy and 5-phenyl-2S-pentyloxy, i.e.

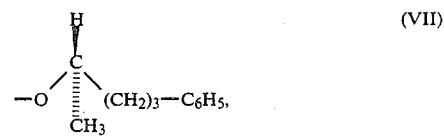

(VII)

is most preferred.

Particularly preferred intermediates of formula (II) and (III) are those wherein $R_{16}$ and $R_{17}$ are each hydrogen, $R_{15}$ is H, $CH_3$ or benzyl; and $Z_1$ is OH, benzyloxy, methoxy or one of the particularly preferred values of Z, above.

Particularly preferred compounds of formula (I) wherein M is N are those having the absolute or relative stereochemistry specified in the formula

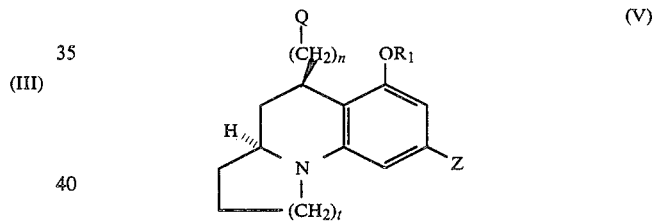

(V)

Particularly preferred compounds of formula (I) wherein M is CH are those having the absolute or relative stereochemistry specified in the formula

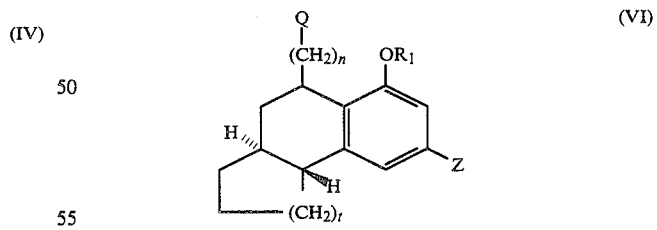

(VI)

The ring systems and numbering used herein for the compounds of the present invention are as follows:

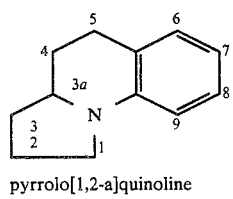

pyrrolo[1,2-a]quinoline

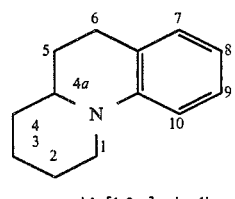

pyrido[1,2-a]quinoline

-continued benz[e]indene phenanthrene

Thus the compounds of formula (V) and (VI) are named as follows:

(V), t=1: 1,2,3,3aS,4,5R-hexahydro-5-[(CH$_2$)$_n$Q-substituent]-6-(OR$_1$-substituent)-8-(Z-substituent)-pyrrolo[1,2-a]quinoline;

(V), t=2: 2,3,4,4aS,5,6R-hexahydro-6-[(CH$_2$)$_n$Q-substituent]-7-(OR$_1$-substituent)-9-(Z-substituent)-1H-pyrido[1,2-a]quinoline;

(VI), t=1: 2,3,3aS,4,5,9bR-hexahydro-5-[(CH$_2$)$_2$Q-substituent]-6-(OR$_1$-substituent)-8-(Z-substituent)-1H-benz[e]indene; and (VI), t=2: 1,2,3,4,4aS,5,6,10bR-octahydro-6-[(CH$_2$)$_n$Q-substituent]-7-(OR$_1$-substituent)-9-(Z-substituent)-phenanthrene.

Likewise, the compounds of (II) are named as cyclic mono- or diketones having the above ring systems and numbering, the compounds of formula (III) are named as lactones of the corresponding compounds of formula (I) where R$_1$ is H, n is 1 and Q is COOH or the corresponding unsaturated carboxylic acid.

Also included in this invention are pharmaceutically acceptable cationic and acid addition salts of the compounds of formula (I). By pharmaceutically acceptable cationic salts of the compounds of the invention is meant the salts of those compounds of formula (I) where Q is a carboxylic acid group, said salts are formed by neutralization of the carboxylic acid by bases of pharmaceutically acceptable metals, ammonia and amines. Examples of such metals are sodium, potassium, calcium and magnesium. Examples of such amines are ethanolamine and N-methylglucamine.

By the term pharmaceutically acceptable acid addition salts is meant the addition salts formed between those compounds of formula (I) having one or more basic nitrogen atoms in substituents M, R$_1$, Q or Z, and a pharmaceutically acceptable acid. Examples of such acids are acetic, benzoic, hydrobromic, hydrochloric, citric, sulfosalicylic, tartaric, glycolic, malonic, maleic, fumaric, malic, 2-hydroxy-3-naphthoic, pamoic, salicylic, phthalic, succinic, gluconic, mandelic, lactic, sulfuric, phosphoric, nitric and methanesulfonic acids. Of course, when more than one basic nitrogen atom is present in the free base of formula (I), mono-, di- or higher addition salts may be obtained by employing one, two or more equivalents of acid to form the desired acid addition salt.

Compounds having the formulae (I), (III), (V) and (VI), above, contain asymmetric centers at the carbon sharing the ring juncture with M, at the carbon bearing —(CH$_2$)$_n$Q and M when it is CH. There may be additional asymmetric centers in the substituents Q, R$_1$ and Z. The present invention includes the racemates of formula (I), the diastereomeric mixtures, pure enantiomers and diastereomers thereof. The utility of the racemic mixtures, the diastereomeric mixtures, as well as of the pure enantiomers and diastereomers is determined by the biological evaluations described below.

As mentioned above, the compounds of the invention are particularly useful s analgesics, and as antiemetic and antinausea agents for use in mammals, including man. The invention further provides a method for producing analgesia in mammals and a method for prevention and treatment of nausea in a mammal subject to nausea, in each case by oral or parenteral administration of an effective amount of a compound of formula (I) or its pharmaceutically acceptable salt.

Also provided are pharmaceutical compositions for use as analgesics, as well as those suitable for use in prevention and treatment of nausea, comprising an effective amount of compound of the invention and a pharmaceutically acceptable carrier.

Also included within the scope and purview of the present invention are the valuable novel CNS agents of the formulae below.

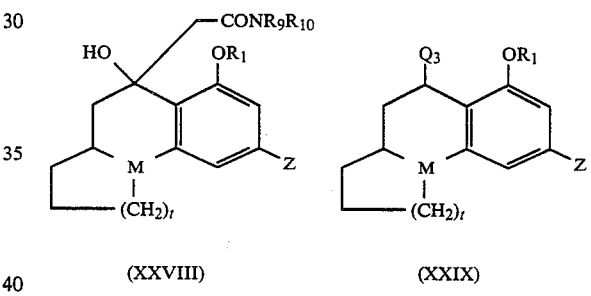

(XXVIII)    (XXIX)

where t, M, R$_1$, R$_9$, R$_{10}$ and Z are as previously defined and Q$_3$ is
CONHCOR$_4$,
CONHSO$_2$R$_{12}$ or

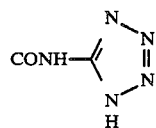

and R$_4$ and R$_{12}$ are as previously defined.

DETAILED DESCRIPTION OF THE INVENTION

Methods which can be employed to provide the valuable intermediates of formulae (IX), (IV) and (III) and their conversion to the therapeutically active compounds of formula (I) where M is N or CH and n is 1, are outlined in Flow Chart A.

FLOW CHART A

For compounds of the invention where M is N or CH and n is 1 or 2:

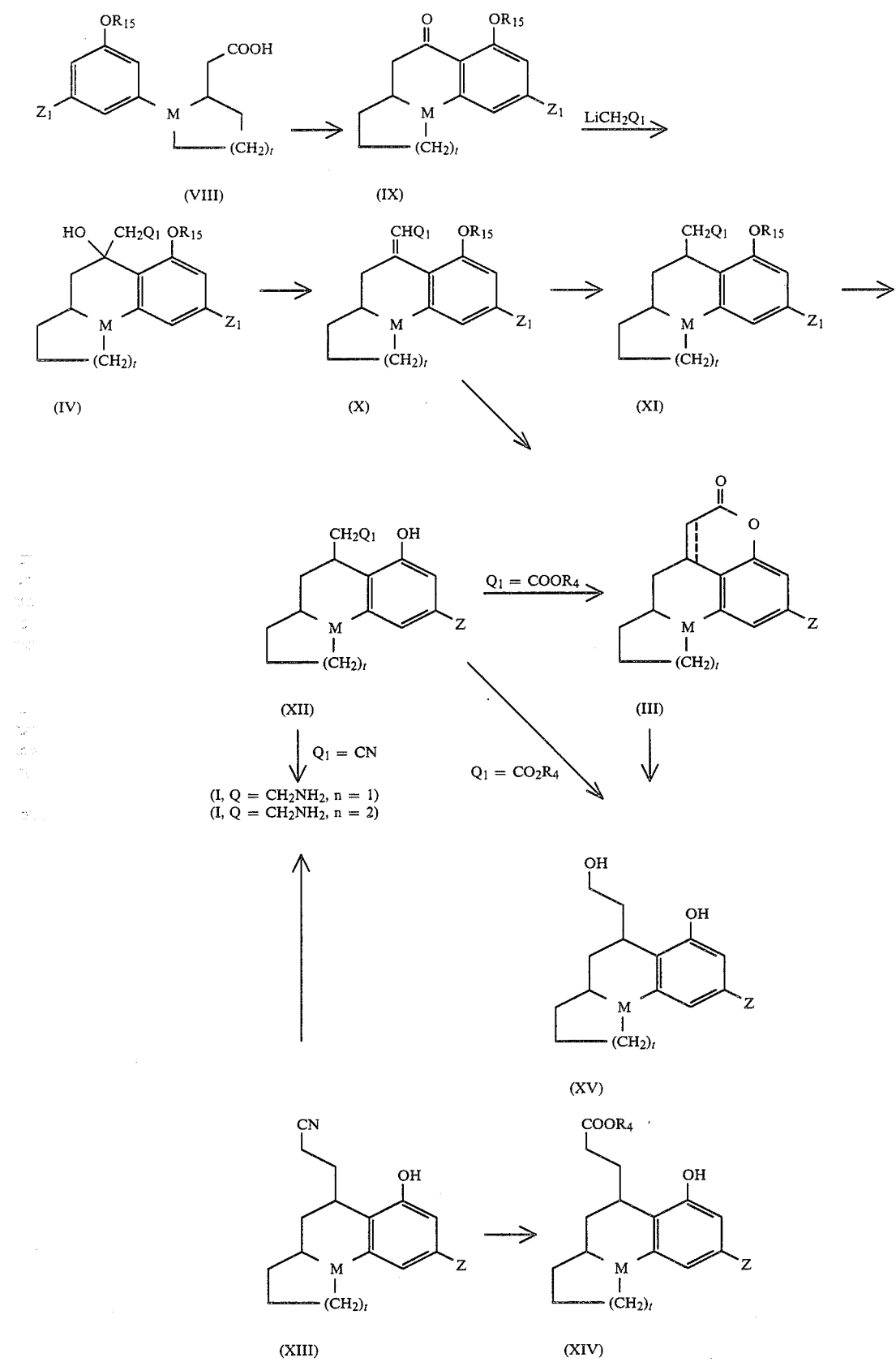

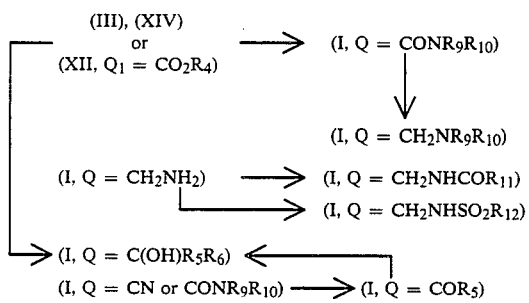

The enantiomeric or racemic starting materials of formula (VIII) wherein t, M, $R_{15}$ and $Z_1$ are as previously defined and $R_{15}$ is preferably benzyl or methyl are cyclized under dehydrating conditions to form the corresponding tricyclic ketones of formula (IX). In a typical reaction of this type the compound (VIII) is treated with a mixture of acetic acid/acetic anhydride or trifluoroacetic acid/trifluoroacetic anhydride in molar excess, at a temperature of from about 0° to 100° C. until the cyclization is substantially complete, which usually requires from a few minutes up to several hours. The volatiles are then evaporated under reduced pressure, the product isolated by standard extraction methods and purified if desired by crystallization or by chromatographic methods.

In the second step of this reaction sequence the ketone of formula (IX) is reacted under Reformatsky reaction conditions with an alpha-haloester or alpha-halonitrile in the presence of zinc metal, but preferably with a lithio acetic acid ester or lithio acetonitrile reagent of the formula $LiCH_2Q_1$, where $Q_1$ is $COOR_4$ or CN and $R_4$ is alkyl having from one to four carbon atoms. For an extensive review of the Reformatsky reaction, see, e.g. Rathke, *Organic Reactions*, 22, 423–460 (1975).

When the preferred lithio reagents, $LiCH_2Q_1$, are employed to prepare the intermediates of formula (IV), they may be prepared by any of several methods known in the art; see, for example, Fieser, "Reagents for Organic Chemistry", Wiley-Interscience, New York, Vol. 3, 1972. However, a preferred method, exemplified herein, employs a lithium dialkylamide and an acetic acid ester or nitrile of formula $CH_3Q_1$ in reaction inert solvent. A particularly preferred lithium dialkylamide is lithium dicyclohexylamide. The latter compound is prepared, for example, from equimolar amounts of n-butyl lithium and dicyclohexylamine in reaction inert solvent. In a typical reaction the two reagents are contacted under anhydrous conditions and in the presence of an inert atmosphere, e.g., nitrogen, at −80° to −70° C. in reaction inert solvent and to the resulting slurry is added an equimolar amount of reagent of formula $CH_3Q_1$ at the same temperature. The resulting lithio reagent, $LiCH_2Q_1$ is then reacted immediately with the intermediate ketone (IX) in reaction inert solvent also at a temperature of from about −80° to −70° C. The reaction is ordinarily completed in from about one to ten hours, after which the reaction mixture is quenched by addition of an equivalent amount of weak acid, e.g., acetic acid, to decompose the lithium salt of the desired product. The product is then isolated by standard methods and purified, if desired, as described above. Examples of the reaction inert solvents which may be employed and preferred such solvents are those mentioned above for the reaction employing haloester or halonitrile reagents.

The 5,5-(or 6,6-)hydroxy-$CH_2Q_1$-disubstituted compounds of formula (IV), obtained as described above, are then subjected to hydrogenolysis and removal of hydroxy protecting methyl or benzyl groups, $R_{15}$, to provide compounds of formulae (X), (XI) or a mixture thereof. The hydrogenolysis of compounds of formula (IV) where $Q_1$ is $COOR_4$ is ordinarily carried out by means of hydrogen in the presence of a noble metal catalyst. Examples of noble metals which may be employed are nickel, palladium, platinum and rhodium. The catalyst is ordinarily employed in catalytic amounts, e.g., from about 0.01 to 10 weight-percent and preferably from about 0.1 to 2.5 weight-percent, based on the compound of formula (IV). It is often covenient to suspend the catalyst on an inert support, a particularly preferred catalyst is palladium suspended on an inert support such as carbon.

One convenient method of carrying out this transformation is to stir or shake a solution of the compound of formula (IV) under an atmosphere of hydrogen in the presence of one of the above noble metal catalysts. Suitable solvents for this hydrogenolysis reaction are those which substantially dissolve the starting compound of the formula (IV) but which do not themselves suffer hydrogenation or hydrogenolysis. Examples of such solvents include the lower alkanols such as methanol, ethanol and isopropanol; ethers such as diethyl ether, tetrahydrofuran, dioxan and 1,2-dimethoxyethane; low molecular weight esters such as ethyl acetate and butyl acetate; tertiary amides such as N,N-dimethylformamide, N N-dimethylacetamide and N-methylpyrrolidone; and mixtures thereof. Introduction of the hydrogen gas into the reaction medium is usually accomplished by carrying out the reaction in a sealed vessel, containing the compound of formula (IV), the solvent, the catalyst and the hydrogen. The pressure inside the reaction vessel can vary from about 1 to about 100 kg/cm². The preferred pressure range, when the atmosphere inside the reaction vessel is substantially pure hydrogen, is from about 2 to about 5 kg/cm². The hydrogenolysis is generally run at a temperature of from about 0° to about 60° C., and preferably from about 25° to about 50° C. Utilizing the preferred temperature and pressure values, hydrogenolysis generally takes place in a few hours, e.g., from about 2 hours to about 24 hours.

The product is then isolated by standard methods known in the art, e.g., filtration to remove the catalyst and evaporation of solvent or partitioning between water and a water immiscible solvent and evaporation of the dried extract.

When the starting compound employed in the hydrogenolysis is of formula (IV) wherein $R_{15}$ is hydrogen or benzyl and $Q_1$ is $COOR_4$, the product obtained is ordinarily a mixture of the corresponding carboxylic acid or ester of formula (XII) and the lactone of formula (III) formed by elimination of the elements of $R_4OH$ from (XII), (XI) or (X) where $R_{15}=H$. The mixture thus obtained may be used as is or may be separated by well known methods, e.g., by crystallization and/or chromatography on silica gel.

Of course, when the starting compound for the hydrogenolyis is of formula (IV) wherein $R^{15}$ is alkyl, as defined above and $Q_1$ is $COOR_4$, the only product obtained is the corresponding $OR^{15}$-substituted derivative of formula (XI). Removal of the hydroxy protecting group $R^{15}$, by methods known in the art for cleaving ethers e.g., by means of HBr/acetic acid, then affords the desired compound of (XII) or its mixture with lactone (III).

In a preferred method for conversion of compounds of formula (IV) where $Q_1$ is CN to the corresponding compound of formula (XII), the compound (IV) is first dehydrated to form a 4-cyanomethylene derivative and this is hydrogenated by means of magnesium in methanol to form the hydroxy-protected derivative (XI) from which the protecting group is then removed. This sequence is outlined below for the case wherein $Q_1$ is CN and $R^{15}$ is $CH_2C_6H_5$.

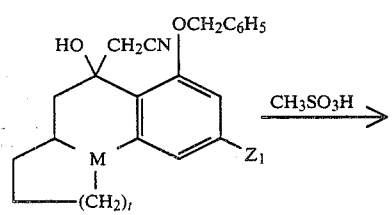

[(IV) $Q_1$ = CN, $R^{15}$ = $CH_2C_6H_5$]

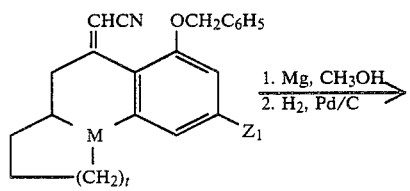

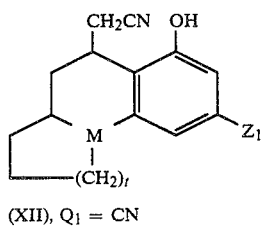

(XII), $Q_1$ = CN

Reaction of compounds (IV) wherein $Q_1$ is $COOR_4$ with amines of formula $R_9R_{10}NH$ leads to the corresponding amide CNS agents of the formula

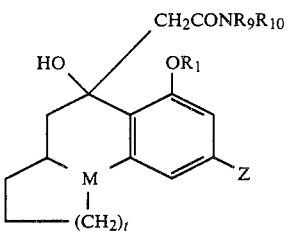

The dehydration of the above nitrile of formula (IV) is carried out in a reaction inert solvent, e.g., benzene, toluene or ethyl ether. To the solution of the starting 4-hydroxy compound is added an absorbent for water, e.g., molecular sieves, and a catalytic amount of methanesulfonic acid and the mixture stirred at room temperature, typically overnight. The dehydrated product is isolated by standard methods and reduced in methanol in the presence of magnesium metal at $-10°$ to $30°$ C., typically this reaction is complete in from about 4 to 48 hours. The benzyl protecting group is then removed by catalytic hydrogenation as described above.

The products of formulae (XII, $Q_1=CO_2R_4$) and (III), as well as mixtures thereof, are useful intermediates for production of the corresponding hydroxy compounds of formula (XV) by means of known reducing agents, e.g., hydrides such as lithium aluminum hydride or lithium borohydride, aluminum borohydride, borane, aluminum hydride and lithium triethylborohydride and by catalytic hydrogenation over noble metal catalysts. Preferred reducing agents are the above hydrides and especially preferred is lithium aluminum hydride for reasons of economy and efficiency. The reduction is carried out under anhydrous conditions and in the presence of a suitable reaction inert solvent e.g., ethyl ether, tetrahydrofuran, 1,2-dimethoxyethane and diethyleneglycol dimethylether. Typically, the compound of formula (XII, $Q_1=CO_2R_4$), the lactone (III) or mixture thereof dissolved in one of the above reaction inert solvents is added to a solution of an approximately equimolar amount of hydride, e.g., lithium aluminum hydride, in the same solvent and the mixture maintained at a temperature of from about $-50°$ to $50°$ C., and preferably from about $0°$ to $30°$ C. Under these conditions the reduction is substantially complete in from about 2 to 24 hours, after which the excess reducing agent is quenched, e.g., by cautious addition of wet solvent or ethyl acetate and the product isolated by known techniques, e.g., washing the reaction mixture with water and evaporation of the dried organic phase. Purification, if desired, is carried out, e.g., by recrystallization or column chromatography.

The lactones (III) wherein the broken line is no bond are also useful as intermediates for production of the corresponding lactols of formula (XXVI) by means of reagents and conditions known to selectively reduce the lactone carbonyl group to a carbinol without ring cleavage. A preferred such reagent is diisobutylaluminum hydride (DIBALH). In a typical reaction, the saturated lactone (III) is dissolved in a reaction inert solvent, such as an aromatic hydrocarbon solvent, preferably toluene, the solution is cooled to a temperature of from about $-90°$ to $-50°$ C., preferably about $-80°$ to $-60°$ C., under anhydrous conditions and in the presence of an inert atmosphere such as nitrogen or argon. An equimolar amount of DIBALH is then added slowly while maintaining the mixture within the preferred temperature range. After the addition is complete, the reaction is allowed to proceed under these conditions until substantially complete, which ordinarily requires from about one to ten hours. The reaction mixture is then quenched, for example, by addition of methanol, then allowed to warm to room temperature. The desired lactol (XXVI) is then isolated, e.g., by washing with water, drying and evaporation of solvent.

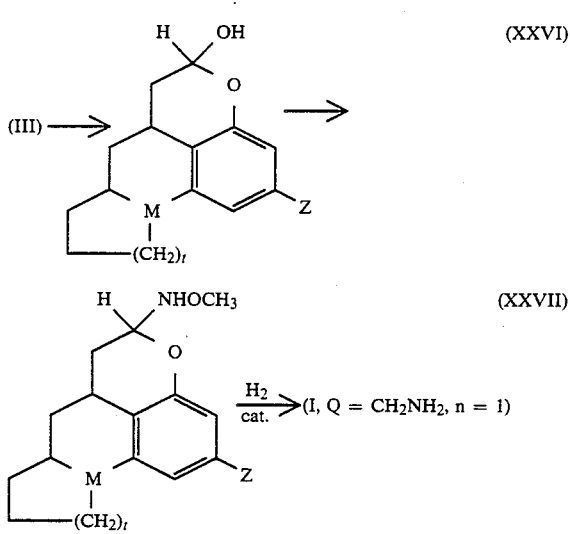

Reaction of the lactols of formula (XXVI) with alcohols of formula $(R_8)'OH$, where $(R_8)'$ is alkyl having from one to four carbon atoms, under acidic conditions known to convert lactols (hemiacetals) to acetals provides the corresponding acetals. In a typical reaction, the lactol is dissolved in a large excess, e.g., a solvent amount of the alcohol of formula $(R_8)'OH$, dry hydrogen chloride or concentrated sulfuric acid added in from a catalytic amount up to an amount equimolar to the lactol and the mixture maintained at a temperature of from about 0° C. up to the boiling point of the alcohol, preferably room temperature, until acetal formation is complete. The time required for completion is ordinarily about 4–48 hours. After which the acetal is isolated by known methods, e.g., by pouring into water, extracting with ether, drying the extracts and evaporation of solvent. The product thus provided is ordinarily a mixture of the alpha- and beta-anomeric acetals which can be separated, e.g., by chromatography on silica gel.

The lactols of formula (XXVI) are also useful intermediates for preparation of amines of formula (I, n=1, $Q=CH_2NH_2$) via an alkoxyamino intermediate, e.g., the methoxyamino compounds of formula (XXVII). The lactol is first reacted with an alkoxyamine, preferably methoxyamine. Equimolar amounts of the reactants are contacted in the presence of a suitable solvent such as, for example, methanol, ethanol, tetrahydrofuran, dimethylformamide, pyridine or mixtures thereof. Preferred solvents are ethanol, pyridine or their mixtures. The reaction can be carried out satisfactorily at a temperature in the range of from about −20° to 50° C.; however, a temperature of from about −10° to 25° C. is preferred. Under preferred conditions the reaction is ordinarily complete in from about one to six hours. The product of formula (XXVII) is then isolated by standard means, e.g., by evaporation of solvent and partitioning the residue between water and a water immiscible solvent, e.g., ethyl ether.

Catalytic hydrogenolysis of the alkoxyamino intermediate affords the corresponding tricyclic compound of formula (I) where Q is $CH_2NH_2$, n=1 and $R_1$ is H. The hydrogenolysis is carried out in the presence of hydrogen and a noble metal catalyst under conditions described above for hydrogenolysis of compounds of formula (IV). However, a particularly preferred method employs a nickel/aluminum alloy in the presence of aqueous alkali, e.g., sodium hydroxide or potassium hydroxide. The reaction of the aluminum with alkali produces the requisite hydrogen and continually provides fresh catalyst (nickel) for the reaction at the same time. In a particularly preferred embodiment of this reaction approximately equal weights of the methoxyamino compound (XXVII) and Raney alloy (1:1 by weight nickel/aluminum) are contacted in the presence of dilute aqueous alkali, e.g., sodium hydroxide and in the presence of a suitable solvent, e.g., methanol or ethanol. The mixture is heated at a temperature of from about 40° C. up to the reflux temperature of the mixture. The reaction is substantially complete in from about 1 to 10 hours, after which the product (I, $Q=CH_2NH_2$, n=1, $R_1=H$) is isolated by known methods and purified, e.g., by column chromatography.

The compounds of formula (I, $Q=CH_2NH_2$, n=1, $R_1=H$) can also be prepared by reduction of the compounds of formula (XII, $Q_1=CN$) employing hydrogen in the presence of a noble metal catalyst or by means of hydride reducing agents such as e.g., borane, aluminum hydride, lithium aluminum hydride or lithium triethylborohydride. A particularly preferred method employs lithium aluminum hydride in the presence of a reaction inert solvent, e.g., ethyl ether or tetrahydrofuran under conditions set forth above for reduction of the corresponding esters (XII, $Q_1=COOR_4$) with the same reagent to form compounds of formula (XV).

The compounds of the invention wherein n is zero and the imido derivatives of formula (XXIX) are obtained, for example, from the intermediate ketones of formula (IX) as outlined below.

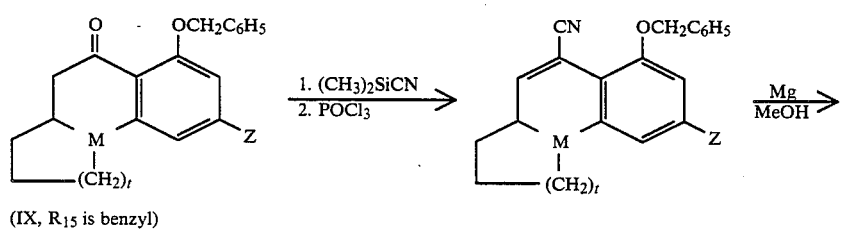

(IX, $R_{15}$ is benzyl)

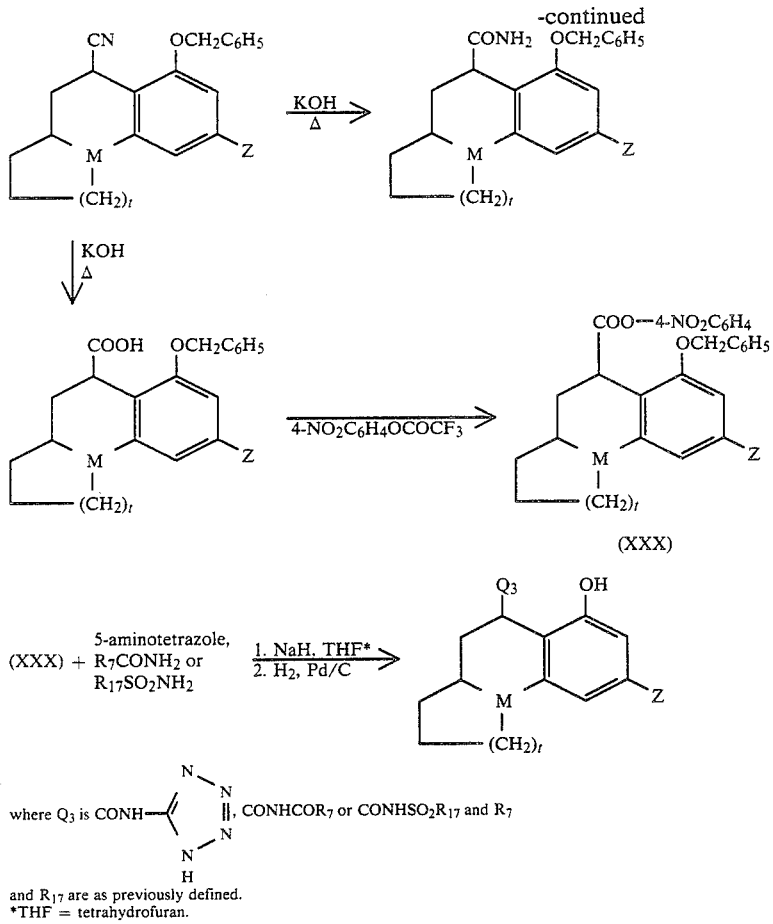

where $Q_3$ is CONH—[tetrazole], CONHCOR$_7$ or CONHSO$_2$R$_{17}$ and R$_7$ and R$_{17}$ are as previously defined.
*THF = tetrahydrofuran.

Hydrogenolysis of the benzyl group, e.g. with palladium-on-carbon catalyst, can likewise be carried out on any of the above intermediates, to provide the corresponding compound of formula (I) wherein R$_1$ is hydrogen and n is zero. The remaining compounds of formula (I), n is zero are obtained from the nitrile and carboxylate intermediates by methods analogous to those employed for the invention compounds (I) where n is 1 or 2.

The amides of formula (I, Q=CONR$_9$R$_{10}$) are prepared from the esters or acids wherein Q$_1$ is COOR$_4$ by reaction with ammonia or the appropriate amine of formula R$_9$R$_{10}$NH employing standard methods known in the art. Typically, approximately equimolar amounts of the ester, e.g., of formula (XII, Q$_1$=COOR$_4$), and the above amine or ammonia are contacted in the presence of solvent and at a temperature in the range of from about 0° to 100° C. Examples of solvents which may be successfully employed in this reaction are the lower alkanols such as methanol, ethanol, isopropanol and n-butanol; ethers such as diethylether, tetrahydrofuran, 1,2-dimethoxyethane and diethyleneglycol dimethylether; hydrocarbons such as hexane, benzene and toluene and mixtures thereof. Preferred solvents are methanol, ethanol, isopropanol, tetrahydrofuran, toluene and their mixtures.

When acids of formula (XII, Q$_1$=COOH) are employed to provide amides of formula (I, Q=CONR$_9$R$_{10}$), it is preferable to convert the acid to an activated derivative such as the acid halide or a mixed anhydride prior to reaction with the amine or ammonia of formula R$_9$R$_{10}$NH. Typically, the acid is first reacted with an equimolar amount of thionyl chloride to form the corresponding acid chloride by methods well known in the art, and the latter compound reacted with at least an equimolar amount of free base of formula R$_9$R$_{10}$NH, but preferably a molar excess of base, e.g., 2–3 moles, in the presence of a reaction inert organic solvent. The resulting amide is then isolated by filtration to remove precipitated amine hydrochloride salt and the product isolated by washing and evaporation of the filtrate. Preferred reaction inert solvents for this procedure are ethyl ether, tetrahydrofuran, chloroform or methylene chloride. It is also preferred that this reaction be carried out with compounds of formula (XII, Q$_1$=COOH) in which the hydroxy group is protected by acylation in order to prevent unwanted side reaction of the acid halide with the phenolic hydroxy group. A preferred acyl is acetyl. The resulting acyloxyamide, e.g., (I, Q=CONR$_9$R$_{10}$, R$_1$=CH$_3$CO) may then be converted to the corresponding hydroxy compound (R$_1$=H) by contacting the product thus obtained with dilute aqueous alkali, e.g., sodium hydroxide, potassium hydroxide or sodium carbonate.

The amides of formula (I, Q=CONR$_9$R$_{10}$) can be reduced by either catalytic hydrogenation or metal hydrides to provide the corresponding amine derivatives (I, Q=CH$_2$NR$_9$R$_{10}$) as described above for reduction of nitriles (XII, Q$_1$=CN) to provide the primary amines, (I, Q=CH$_2$NH$_2$).

Reaction of the latter primary amine compounds with, e.g., an acid halide of formula R$_{11}$COCl, R$_{11}$COBr or a mixed anhydride of formula $R_{11}COOCOalkyl$ where alkyl is $C_1$-$C_4$, employing the same methods and conditions described above for preparation of amides of formula (I, $Q=CONR_9R_{10}$), provides the desired amides of formula (I, $Q=CH_2NHCOR_{11}$). Similarly, use of a sulfonyl halide of formula $R_{12}SO_2Cl$ or $R_{12}SO_2Br$ affords the corresponding sulfonamide (I, $Q=CH_2NHSO_2R_{12}$) where $R_{12}$ is as previously defined.

The esters of formulae (I, $Q=COOR_4$), (XII) or (XIV) where $R_4$ is alkyl or the lactones of formula (III) also serve as starting materials for preparation of the tertiary alcohols. Said esters or lactones upon reaction with a molar excess of Grignard reagent, $R_5MgX$, where $R_5$ is ($C_1$-$C_4$)alkyl, phenyl or benzyl and X is Cl, Br or I, provide the corresponding compound of formula (I, $R_1=H$, $Q=(R_5)_2COH$). The reaction is ordinarily carried out at a temperature of from about 0° C. up to the reflux temperature of the solvent, preferably at room temperature. The reaction is ordinarily complete in from about 2-24 hours. The excess Grignard reagent is then decomposed and the product isolated by standard methods well known in the art. For example, water is added, the layers separated, the aqueous phase extracted with a water immiscible solvent, e.g., ethyl ether, and the product isolated from the combined extracts by evaporation of solvent. Purification, if desired, is accomplished by, e.g., recrystallization or column chromatography. Preferred reaction inert solvents for this reaction are ethyl ether and tetrahydrofuran.

Grignard reaction of the above described lactols of formula (XXVI) employing equimolar amounts of Grignard reagent and lactol under the above described conditions, similarly provides secondary alcohols of formula (I, n=1, $Q=CH(OH)R_5$, $R_1=H$).

Oxidation of the secondary alcohols or corresponding primary alcohols of formula (I, $Q=CH(OH)R_5$) provided above, employing an oxidizing agent known to oxidize primary and secondary alcohols to aldehydes and ketones, respectively, provides the corresponding compounds of formula (I, $Q=COR_5$) where $R_5$ is hydrogen, $C_1$-$C_4$alkyl, phenyl or benzyl. Oxidizing agents which can be employed for this oxidation are well known in the art, see, e.g., Sandler and Karo, "Organic Functional Group Preparations", Academic Press, New York, 1968, pp. 147-173. Preferred oxidizing agents, however, are chromic acid, chromic anhydride, potassium dichromate, manganese dioxide and lead tetraacetate and particularly preferred is chromic anhydride in pyridine. While the oxidation with the preferred agants above may be carried out over a wide range of temperature, e.g., from about 0° to 100° C., a preferred temperature is from about 10° to 50° C. The alcohol and a molar excess of chromic anhydride, e.g., a 100% molar excess, are contacted in aqueous pyridine. The oxidation is ordinarily complete at a temperature in the preferred range, in from about one to eight hours. After which the product is isolated by pouring the mixture into water, extraction with a water immiscible solvent, e.g., ethyl ether, methylene chloride or chloroform, and evaporation of solvent.

The compounds of formula (I) wherein Q is 5-tetrazolyl are obtained e.g., by reaction of the corresponding nitrile (I, Q=CN) with azide ion in the presence of acid by methods analogous to those disclosed in U.S. Pat. No. 4,081,455. The azide ion can be derived from a variety of sources. The only criterion appears to be that the particular source chosen be capable of releasing azide ion under the conditions employed. Suitable sources of azide ions are, e.g. metal azides, especially the alkali metal azides, trialkylsilyl azides having from one to four carbon atoms in each of the alkyl groups, such as trimethylsilyl azide. Preferred conditions for such reaction are disclosed in U.S. Pat. No. 4,081,455.

Flow Chart B, below, illustrates methods which can be employed to provide the invention compounds of formula (I) wherein n is 2.

FLOW CHART B

For compounds of formula (I), n=2:

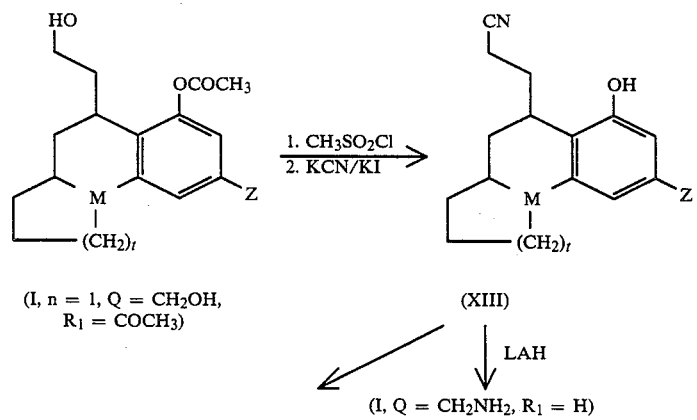

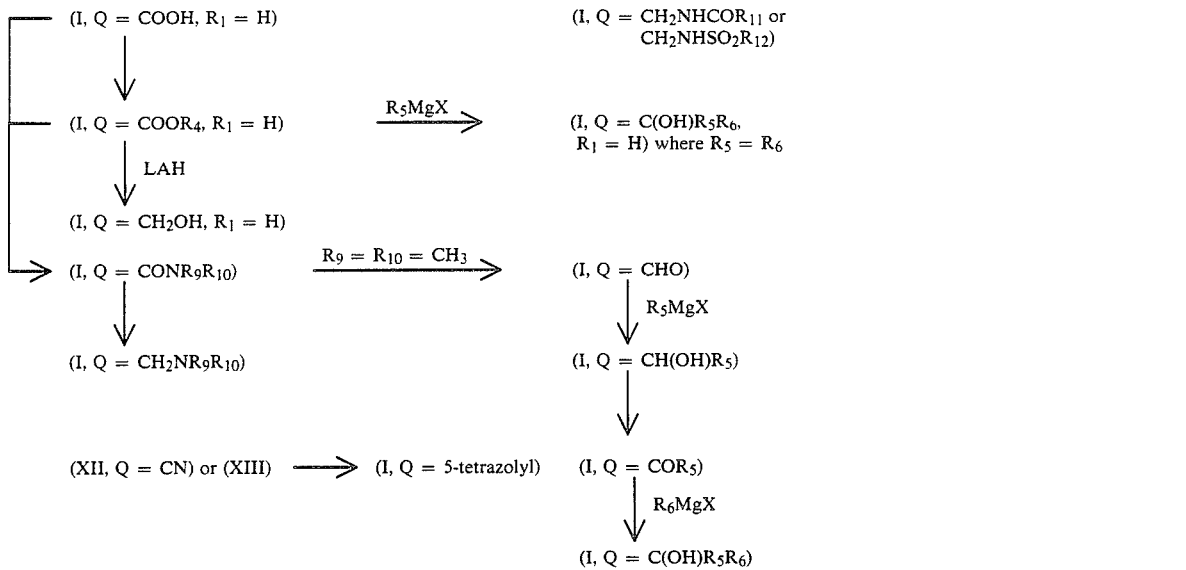

A primary alcohol of formula (I) wherein n is 1, Q is $CH_2OH$, $R_1$ is $COCH_3$ and t and Z are as previously defined is first converted to the corresponding alkylsulfonyl or arylsulfonyl ester wherein alkyl is, e.g., of from one to four carbon atoms and aryl is, e.g., phenyl or tolyl. As especially preferred sulfonyl ester is methylsulfonyl for reasons of economy and efficiency. In a typical such reaction the primary alcohol of formula (I), as defined above, and an equimolar amount of methanesulfonyl chloride are contacted in the presence of a solvent amount of pyridine or triethylamine which also acts as an acid acceptor. The resulting mixture is maintained at a temperature of from about $-10°$ to $40°$ C., preferably from about $0°$ to $30°$ C., at which temperature the reaction is complete in from about 15 minutes to four hours. The methanesulfonyl ester is then isolated by standard techniques, e.g., by evaporation of volatiles and partitioning of the residue between water and a water immiscible solvent, washing and evaporation of solvent.

The mesylate ester thus provided is further reacted with a molar excess, e.g., a 2-20 molar excess, of an alkali metal cyanide, preferably potassium cyanide and preferably in the presence of a catalytic amount of potassium iodide to afford the desired nitrile of formula (XIII) which corresponds to (I, n=2, Q=CN, $R_1$=H). This reaction is ordinarily carried out in the presence of a reaction inert polar solvent, preferably dimethylformamide, dimethylsulfoxide, diethyleneglycol dimethyl ether, or their mixtures with water; and at a temperature of from about $50°$ to $150°$ C., preferably $75°$ to $105°$ C. Under the above mentioned preferred conditions the formation of the desired nitrile is complete in from about one to six hours. The product is isolated by methods well known in the art, e.g., by evaporation of solvent, partitioning the residue between water and water immiscible solvent, e.g., chloroform or methylene chloride and evaporation of the solvent. The residue is purified, if desired, e.g., by chromatography. The nitrile, thus obtained, serves as precursor of the remaining compounds of formula (I, n=2) as shown in Flow Curve B.

Hydrolysis of the nitrile, employing methods and conditions well known in the art for conversion of nitriles to carboxylic acids, affords the acids of formula (I, n=2, Q=COOH). Typically, the nitrile in aqueous alcoholic alkali, e.g., sodium hydroxide is heated at reflux for about 4-24 hours and the product isolated by acidification of the mixture, extraction into a water immiscible solvent, e.g., ethyl ether or chloroform, and evaporation of solvent.

Esterification of the carboxylic acids obtained above with alcohols of the formula $R_7OH$ provides the corresponding esters of formula (I, n=2, Q=COOR$_4$) where $R_4$ is alkyl having from one to four carbon atoms. The esterification is typically carried out by contacting the carboxylic acid (I, n=2, Q=COOH) with a molar excess of alcohol, $R_4OH$, in the presence of a catalytic amount of a strong acid, e.g., hydrogen chloride or sulfuric acid, at a temperature of from about $25°$ C. up to the reflux temperature of the mixture, preferably $50°$ to $110°$ C., for about 4 to 24 hours. The ester is then isolated by neutralization of the mixture with, e.g., sodium hydroxide, filtration and evaporation of the filtrate.

Reduction of the compounds of formula (I, n=2, Q=COOR$_4$) by means of hydrogen and a noble metal catalyst or employing metal hydride reducing agents, e.g., lithium aluminum hydride, as described above for the corresponding compounds wherein n=1, provides the primary alcohols of formula (I, n=2, Q=CH$_2$OH).

The amides of formula (I, n=2, Q=CONR$_9$R$_{10}$) are obtained by reaction of the corresponding acids and esters wherein Q=COOR$_4$ by the methods previously described for the corresponding compounds wherein n=1. Similarly, the compounds of formula (I, n=2, Q=CH$_2$NR$_9$R$_{10}$) are obtained by reduction of the appropriate amide as described above for their counterparts wherein n=1.

The remaining compounds of formula (I, n=2) wherein Q is $CH_2NH_2$, $CH_2NHCOR_{11}$, $CH_2NHSO_2R_{12}$ and $C(OH)R_5R_6$ are also obtained by corresponding procedures previously defined for their counterparts wherein n=1.

The invention compounds of formula (I, Q=CHO) wherein n is 1 or 2 are preferably provided by reaction of the corresponding N,N-dialkylamide of formula (I, Q=CONR$_9$R$_{10}$) with disiamylborane [bis(1,2-dimethylpropyl)borane]. In a typical reaction the tertiary amide, e.g., N,N-dimethylamide, of formula (I) and a molar excess, e.g., a 100% molar excess, of disiamylborane are contacted in a reaction inert solvent, e.g., tetrahydrofuran at a temperature of from about 0° to 50° C., preferably room temperature until the formation of aldehyde is complete, typically from about 2 to 20 hours. The excess reducing reagent is then decomposed by cautious addition of water, the solvent evaporated, the residue isolated by partitioning between water and water immiscible solvent and the solvent evaporated.

Reaction of the aldehydes (I, Q=CHO) wherein n is zero or 2 with an equimolar amount of Grignard reagent, $R_5MgX$, employing methods and conditions previously described for reaction of esters of formula (I, n=1, Q=COOR$_4$) or the corresponding lactones of formula (III), affords the corresponding secondary alcohols of formula [I, Q=CH(OH)R$_5$].

Oxidation of the secondary alcohols of formula (I, Q=CH(OH)R$_5$) employing oxidizing agents and conditions known in the art to convert secondary alcohols to the corresponding ketones, provides the corresponding invention compounds of formula (I, Q=COR$_5$). Examples of oxidizing agents which can be employed in production of these ketones are potassium permanganate, potassium dichromate chromium trioxide and chromium trioxide in the presence of pyridine. In carrying out the oxidation to the starting secondary alcohol in a reaction inert solvent, e.g., dichloromethane, chloroform, benzene, pyridine, water or mixtures thereof, is added at least an equimolar amount, preferably a molar excess, e.g., 100-500% molar excess, of the oxidizing agent and the oxidation allowed to proceed to substantial completion. While this oxidation can be successfully carried out over a wide range of temperatures such as from 0° to 100° C., a preferred temperature when the preferred oxidizing agent is employed is in the range of from 10° to 30° C. Under these conditions the reaction is complete in from about one to six hours, typically two to four hours. A preferred solvent for the oxidation is aqueous pyridine when the oxidizing agent is chromium trioxide in the presence of pyridine. The product is isolated, for example, by pouring the reaction mixture into water, adjusting the mixture to an acidic pH and extraction with a water immiscible solvent, e.g., chloroform, methylene chloride or ethyl ether. Drying the extracts and evaporation of solvent affords the desired ketone.

Reaction of the ketones of formula (I, Q=COR$_5$) with an equimolar amount of a Grignard reagent of formula R$_6$MgX, wherein R$_6$ is as previously defined and is the same or different than R$_5$, employing methods and conditions described above for the reaction of esters of formula (I, or XXI, Q=COOR$_4$) or the lactones of formula (III), affords tertiary alcohols of the invention of formula (I, Q=C(OH)R$_5$R$_6$).

Flow Chart C, below, outlines an alternative method for preparing 5-(2-hydroxyethyl)hexahydropyrrolo[1,2-a]quinoline and 6-(2-hydroxyethyl)hexahydropyrido[1,2-a]quinoline compounds of the formula (XXV), (XV, M is N) or (I, n is 1, Q is CH$_2$OH).

In the initial step of this reaction sequence the 3-oxoadipate diester or 3-oxopimelate diester of formula (XVI), prepared by condensation of the half ester acid chloride of succinic or glutaric acid with ethyl lithioacetate in the presence of a condensing agent, e.g., dicyclohexylcarbodiimide; is contacted with a 3-(OR$_{15}$-substituted)-5-Z$_1$-substituted-aniline of formula (XVII) under hydrogenation conditions. Typically the reactants of formula (XVI) and (XVII) are combined in approximately equimolar amounts in the presence of acetic acid and shaken with a catalytic amount of platinum at ambient temperature under a hydrogen atmosphere until the reduction of the Schiff base formed is complete. After removal of catalyst and evaporation of the bulk of the acetic acid, the residue is added to refluxing HBr/acetic acid to affect cyclization and hydrolysis to the acid of formula (XVIII) or the ketolactam (XIX). When the product is the acid (XVIII), it is further cyclized under dehydration conditions to afford the corresponding compound (XIX). In the intermediates (XVIII) and (XIX) produced from starting anilines (XVII) wherein R$_{15}$ is alkyl or benzyl,

FLOW CHART C

For compounds of the invention where M is N, n is 1:

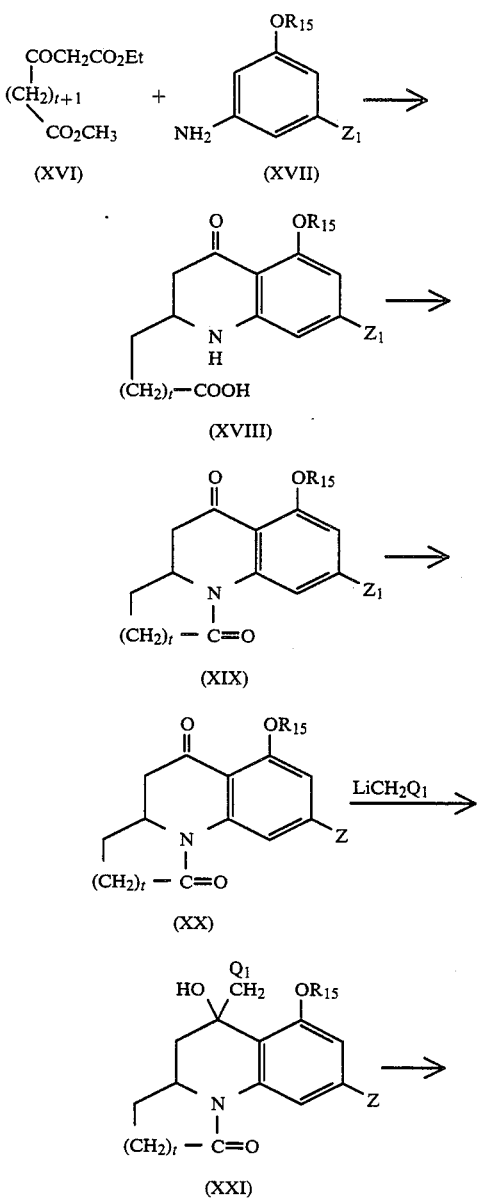

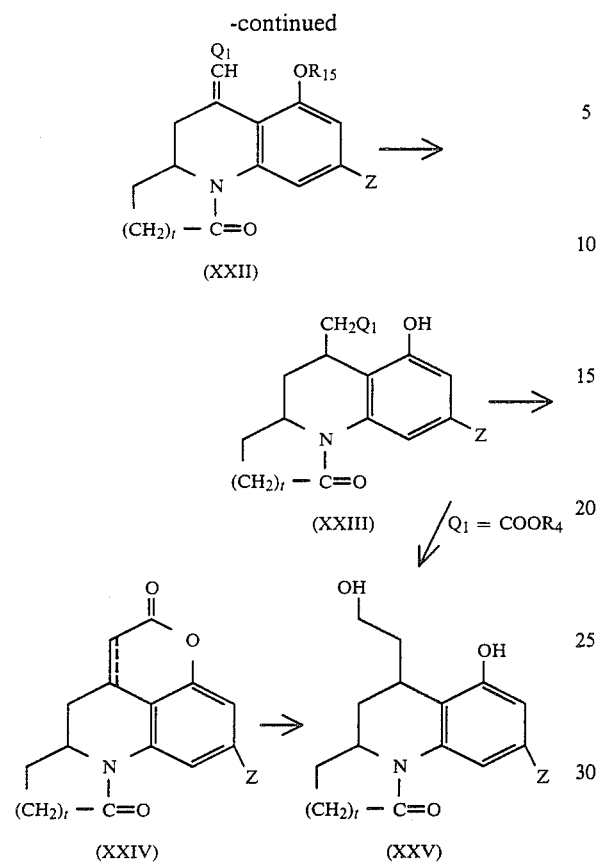

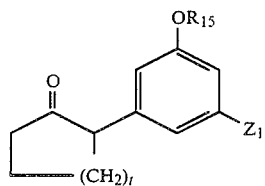

wherein t is as defined above, $R_{15}$ is methyl or benzyl and $Z_1$ is methoxy, benzyloxy, $(C_5-C_{13})$alkyl, $(C_5-C_{13})$alkoxyalkyl, $(C_9-C_{14})$phenylalkyl, or $(C_9-C_{14})$-phenylalkoxyalkyl. Condensation with alkyl acetate, dehydration, and hydrolysis of intermediate ester produces unsaturated acids of the formulae

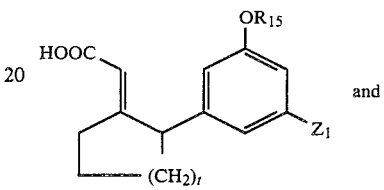

and

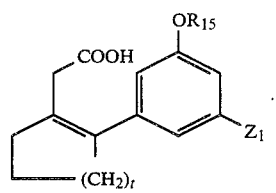

(XXIII)−(XXV)→(I, M=N) for remaining values of $Q_1$ and $R_1$ and/or $Z_1$ is alkoxy or benzyloxy, the ether groups are cleaved by the treatment with HBr/acetic acid, to give products wherein $R_{15}$ and $Z_1$ are H and OH, respectively. When this is the case, it is ordinarily preferable to complete the side chain, Z, by selective esterification, e.g., by reaction of intermediate (XIX, $R_1$=H, $Z_1$=OH) with the appropriate side chain precursor of formula $Z_2X$ where $Z_2$ plus an atom of oxygen forms Z, and X is a leaving group, e.g., Cl, Br, I, $CH_3SO_2O$ or $4—CH_3C_6H_4SO_2O$. A preferred value of X is $CH_3SO_2O$.

The remaining steps to form intermediates (XXI), (XXII), (XXIII), (XXIV) are carried out as previously described for the corresponding steps depicted in Flow Chart A to provide compounds of formulae (IV), (X), (XI), (XII) and (III). The final step, to reduce to lactam-lactone (XXIV), is ordinarily carried out by hydride reduction, preferably employing lithiun aluminum hydride, by methods described above for reduction of lactones (III).

One sequence available for the preparation of numerous starting compounds of formula (VIII, M is CH) employs as a first stage the heating of cyclohexanone or cyclopentanone with a suitable substituted phenyl Grignard in a high boiling, reaction inert solvent to produce a compound of the formula Equivalents such as malonate (decarboxylate to the acetate after hydrolysis) can be substituted for the alkyl acetate. Lithium in liquid ammonia reduction of the former yields the trans-form of the substituted acetic acid derivatives, while catalytic hydrogenation of the latter under conditions detailed above yields the cis-form of the acetic acid (with simultaneous debenzylation when $R_{15}$ is benzyl). Finally, cyclization, debenzylation or O-demethylation and alkylation when Z is a phenolic ether derivative, yields tricyclic ketones of the respective formulae

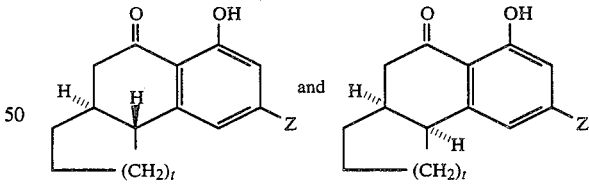

wherein n and Z are as hereinbefore defined.

Alternatively, suitable substituted aromatic aldehydes are condensed with nitromethane to yield trans-1-(disubstituted phenyl)-2-nitroethylenes of the formula

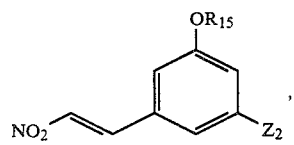

wherein $R_{15}$ is as defined above and $Z_2$ is methoxy, benzyloxy or Z is as defined above. Condensation of the latter with butadiene under Diehls-Alder conditions yields the corresponding 4-(substituted phenyl)-5-nitrocyclohexene. The Nef reaction converts the nitro compound to the unsaturated cyclohexanone derivative, viz, 6-(disubstituted phenyl)-3-cyclohexen-1-one which is hydrogenated according to methods detailed above (with simultaneous removal of benzyl, if present); demethylated if methyl ether is present (with simultaneous dealkylation if $Z_2$ is an alkoxy derivative); and alkylated if Z is an alkoxy derivative to yield a ketone of the formula

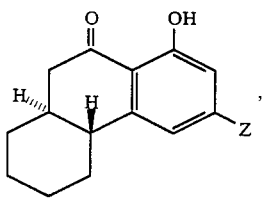

wherein Z is as defined above. It will be noted that inversion occurs in such alkylation reactions, e.g., 5-phenyl-2S-pentyl mesylate yields Z as 5-phenyl-2R-pentyloxy.

Corresponding tricyclic nitrogen analogs are conveniently prepared from 3,omega-dihalo acids and disubstituted anilines, e.g.,

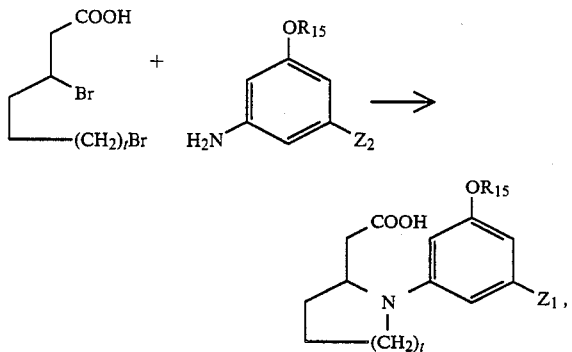

wherein t, $R_{15}$, $Z_1$ and $Z_2$ are as defined above, followed by cyclization, debenzylation or demethylation (accompanied by dealkylation when $Z_2$ is an alkoxy derivative) and alkylation when Z is an alkoxy derivative to yield pyrrolo/pyrido[1,2-a]quinolinones of the formula

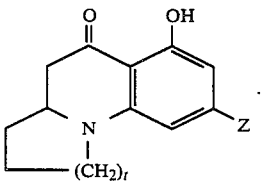

Many of the anilines, aromatic halides or aromatic aldehydes required as starting materials for the present syntheses are available commercially or their syntheses are reported in the literature. When not otherwise available, the anilines required for the present syntheses are prepared by methods previously set forth by Johnson, U.S. Pat. No. 4,260,764. The latter are converted to the corresponding aromatic bromides and chlorides according to procedures set forth by Bigelow, Organic Syntheses I, pp. 135-137 (1941) and then reacted with magnesium to provide the required Grignard reagents. While a variety of methods are available for the synthesis of the required aldehydes they are also broadly available from the anilines of Johnson. The anilines are converted to the corresponding nitriles by the method of Clarke and Read, Organic Syntheses I, pp. 514-516 (1941). The nitriles are subjected to the Stephen reduction to yield the aldehyde directly. Alternatively, the nitriles are hydrolyzed to acid, then converted to acid chloride and hydrogenated under Rosemund conditions. Acid chlorides can also be converted to the thiol ester and desulfurized to aldehydes according to Wolfram et al., J. Am. Chem. Soc. 68, pp. 1455-1546. Alternatively, aldehydes are obtained from the corresponding benzyl aldehydes by oxidation in dimethylsulfoxide according to Kornblum et al., J. Am. Chem. Soc. 81, pp. 4113-4114. The benzyl bromides are prepared according to methods set forth in Althuis et al., U.S. Pat. No. 4,188,495. Aldehydes are also available by reaction of aromatic Grignard reagents with ethyl orthoformate.

When Z is $(C_5-C_{13})$alkoxy, $(C_8-C_{13})$pyridylalkoxy, or $(C_9-C_{14})$phenylalkoxy (the phenyl group optionally substituted with a chloro or fluoro), the required halide or mesylate, if not available commercially, is readily obtained from the corresponding alcohol using conditions standard in the chemical art. The alcohols in turn are available commercially or by literature methods. For example primary alcohols are available by hydride reduction of aldehydes, acids or esters, while secondary alcohols are available by hydride reduction of ketones. All varieties of alcohols are available by the hydration of olefins, or by the reaction of epoxides with Grignard reagents. Furthermore, many halides suitable for the introduction of the sidechain are available by direct halogenation of olefins or addition of hydrogen halides to olefins.

When the optically active variant of one of the compounds of the present invention is desired, resolution is accomplished by formation and separation of diastereomeric salts derived from an optically active amine/acid with an acidic/basic intermediate or end product according to methods well known in the chemical art. Alternatively, alcohol intermediates are resolved by formation of diasteromeric esters, e.g. optically active amine salts of hemiphthalate esters or are formed directly by use of optically active reagents. It is preferred, however, to carry out the resolution at an early stage in the process in order to avoid unnecessary processing of material which is not desired.

The pharmaceutically acceptable acid addition salts of the present invention are readily prepared by contacting the free base with the appropriate mineral or organic acid in either aqueous solution or in a suitable organic solvent. The salt can then be obtained by precipitation or by evaporation of the solvent. The pharmaceutically acceptable acid addition salts of this invention include, but are not limited to, those formed with hydrochloric, hydrobromic, nitric, phosphoric, sulfuric, benzenesulfonic, citric, laurylsulfonic, fumaric, oxalic, maleic, methanesulfonic, tartaric, p-toluenesulfonic, and succinic acid. With polybasic acids, the salt can include more than one mole of base per mole of acid. However, the acid addition salts which are mole for mole are preferred. If desired, these salts are isolated directly from reaction mixtures by suitable modification of the isolation procedure, without isolation of the intermediate free acid.

The pharmaceutically acceptable cationic salts of the compounds of the present invention are readily prepared by reacting the acid forms with an appropriate base, usually one equivalent, in a co-solvent. By the expression "pharmaceutically acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as benzathine (N,N'-dibenzylethylenediamine), choline, diethanolamine, ethylenediamine, meglumine (N-methylglucamine), benethamine (N-benzylphenethylamine), diethylamine, piperazine, and tromethamine (2-amino-2-hydroxymethyl-1,3-propanediol). Typical bases employed in the preparation of these cationic salts are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (e.g., sodium ethylhexanoate, magnesium oleate), employing a solvent in which the desired cationic salt precipitates, or can be otherwise isolated by concentration and/or addition of a non-solvent. If desired, these salts are isolated directly from reaction mixtures by suitable isolation procedures, without isolation of the intermediate free acid.

Phenolic esters of compounds of formula (I) wherein $R_1$ is benzoyl, alkanoyl or $-CO-(CH_2)_p-NR_2R_3$ are readily prepared by reacting formula (I) compounds wherein $R_1$ is hydrogen with benzoic acid, the appropriate alkanoic acid or acid of formula $HOOC-(CH_2)_p-NR_2R_3$ in the presence of a condensing agent such as dicyclohexylcarbodiimide. Alternatively, they are prepared by reaction of the formula (I) ($R_1=H$) compound with the appropriate acid chloride or anhydride, e.g., benzoyl chloride, acetyl chloride or acetic anhydride, in the presence of a base such as pyridine.

The presence of a basic group in the ester moiety ($OR_1$) in the compounds of this invention permits formation of acid-addition salts involving said basic group. When the herein described basic esters are prepared via condensation of the appropriate amino acid hydrochloride (or other acid addition salt) with the appropriate compound of formula (I) in the presence of a condensing agent, the hydrochloride salt of the basic ester is produced. Careful neutralization affords the free base. The free base form can then be converted to other acid addition salts by known procedures.

The analgesic properties of the compounds of this invention are determined by tests using thermal nociceptive stimuli, such as the mouse tail flick procedure, or chemical nociceptive stimuli, such as measuring the ability of a compound to suppress phenylbenzoquinone irritant-induced writhing in mice. These tests and others are described below.

TESTS USING THERMAL NOCICEPTIVE STIMULI (a) Mouse Hot Plate Analgesic Testing The method used is modified after Woolfe and MacDonald, J. Pharmacol. Exp. Ther., 80, 300–307 (1944). A controlled heat stimulus is applied to the feet of mice on a 1/8" thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½" diameter) resting on the hot plate, and timing is begun when the animal's feet touch the plate. At 0.5 and 2 hours after treatment with the test compound the mouse is observed for the first "flicking" movements of one or both hind feet, or until 10 seconds elapse without such movements. Morphine has an $MPE_{50}=4$–5.6 mg./kg. (s.c.).

The physician will determine the dosage which will be most suitable for an individual patient and it will vary with the age, weight and response of the particular patient and the route of administration. Generally, however, the initial analgesic dosage in adults is from 0.01 to 500 mg. per day in single or divided doses. In many instances, it is not necessary to exceed 100 mg. daily. The favored oral dosage range is from 0.01 to about 300 mg./day; the preferred range is from 0.10 to about 50 mg./day. The favored parenteral dose is from 0.01 to 100 mg./day; the preferred range is from 0.01 to 20 mg./day.

The use of these compounds for the treatment of glacuoma is believed to be due to their ability to reduce intraocular pressure. Their effects on intraocular pressure are determined by tests on dogs. The test drug is instilled into the eye of a dog in the form of a solution or is administered systemically at various periods of time after which the eye is anesthetized by instillation of tetracaine hydrochloride, ½%, 2 drops. A few minutes after this local anesthesia, intraocular pressure readings are taken with a Schiotz mechanical tonometer and after fluorescein dye is administered, with a Holberg hand application tonometer. The test drug is conveniently used in a solution such as the following: test drug (1 mg.), ethanol (0.05 ml.), Tween 80 (polyoxyalkylene derivative of sorbitan monooleate, available from Atlas Powder Co., Wilmington, Del. 19899; 50 mg.) and saline (to make 1 ml.), or in a more concentrated solution wherein the ingredients are present in proportions of 10 mg., 0.10 ml., 100 mg. and 1 ml., respectively. Alternatively the compounds of the present invention are tested for their ability to reduce intraocular pressure in normal rabbits according to the method of Elsohly et al., J. Clin. Pharmacol. 21, pp. 472S–478S (1981). For human use, concentrations of drug from 0.01 mg./kg. to 10 mg./kg. are useful.

Their activity as diuretic agents is determined by the procedure of Lipschitz et al., J. Pharmacol., 79, 97 (1943) which utilizes rats as the test animals. The dosage range for this use is the same as that noted above with respect to their use as analgesic agents.

The antiemetic properties of the compounds of the present invention are determined in unanesthetized unrestrained cats according to the procedure described by McCarthy and Borison, J. Clin. Pharmacol., 21, 30S–37S (1981). The dosage ranges for this utility is also the same as that noted above with respect to their analgesic utility.

This invention also provides pharmaceutical compositions, including unit dosage forms, valuable for the use of the herein described compounds as analgesics and other utilities disclosed herein. The dosage form may be given in single or multiple doses, as previously noted, to achieve the daily dosage effective for a particular utility.

The compounds (drugs) described herein can be formulated for administration in solid or liquid form for oral or parenteral administration. Capsules containing drugs of this invention; i.e.; compounds of formulae (I), (V) or (VI), are prepared by mixing one part by weight of drug with nine parts of excipient such as starch or milk sugar and then loading the mixture into telescoping gelatin capsules such that each capsule contains 100 parts of the mixture. Tablets containing the same compounds are prepared by compounding suitable mixtures of drug and standard ingredients used in preparing tablets, such as starch, binders and lubricants, such that each tablet contains from 0.01 to 100 mg. of drug per tablet.

Suspensions and solutions of these drugs of formulae (I), (V) or (VI) are generally prepared just prior to use in order to avoid problems of stability of the drug (e.g. oxidation) or of suspensions or solution (e.g. precipitation) of the drug upon storage. Compositions suitable for such are generally dry solid compositions which are reconstituted for injectable administration.

The present invention is illustrated by the following examples. However, it should be understood that the invention is not limited to the specific details of these examples.

When compounds containing more than one asymmetric center contain a center of unspecified absolute or relative stereochemistry (e.g. 5-phenyl-2-pentyl) it will be understood by those skilled in the art that the product is a mixture of two diastereoisomers or two racemates, respectively, usually in a ratio of about 1:1.

EXAMPLE 1

$O^1$-Ethyl $O^7$-Methyl 3-Oxoheptandioate

A five liter round bottom flask was fitted with a mechanical stirrer, thermometer and a one liter addition funnel. The addition funnel was in turn fitted with a septum into which was introduced a nitrogen line, an equalizing line and a liquid reagent inlet line. The equalizing line was further connected with tubing to a straight vacuum adapter and this adapter was fitted between the addition funnel and the five liter flask. The flask was charged with nitrogen then with 976 ml. (2.05 moles=2.25 equiv.) n-butyllithium in 800 ml. anhydrous tetrahydrofuran (THF) and the mixture was cooled to $-78°$ C. in a dry ice/acetone bath. To this was added 408 ml. (2.05 moles) of dicyclohexylamine in 375 ml. THF dropwise over 45 minutes (temperature kept below $-67°$ C.). After equilibrating to $-78°$ C., 201 ml. (2.05 moles) of freshly distilled ethyl acetate in 100 ml. THF was added dropwise over 45 minutes (below $-67°$ C.). After addition, the mixture was allowed to stir at $-78°$ C. for 15 minutes. After 15 minutes 150 g. (0.91 moles) of methyl 4-(chloroformyl)butyrate dissolved in 200 ml. THF was added dropwise over 30 minutes (below $-70°$ C.). The mixture was then stirred one hour at $-78°$ C., after which 231 ml. (2.05 moles) of glacial acetic acid was added dropwise over 25 minutes. After addition was complete the dry ice/acetone bath was removed and the reaction mixture was allowed to warm to 0° C. After diluting with one liter of ethyl ether, the precipitated inorganic material was filtered and washed well with ether. The combined organic solvents were evaporated in vacuo. The residue was partitioned between $Et_2O/H_2O$ (1000 ml. of each) and separated. The ether layer was washed with 2×500 ml., 0.5N hydrochloric acid (some solids precipitated with the first wash and were filtered; no precipitate was observed with the second wash). The organic layer was washed with 500 ml. $H_2O$, 500 ml. saturated sodium bicarbonate solution, 500 ml. $H_2O$, 500 ml. brine, and finally dried over anhydrous magnesium sulfate.

The ether was filtered and the solvent evaporated in vacuo to yield 108.5 g. (55.1%) of 3-oxopimelic acid, ethyl, methyl diester as a gold colored mobile liquid; $^1$H-NMR (CDCl$_3$) ppm (delta): 1.25 (t, C$\underline{H}_3$CH$_2$O), 1.7-2.7 (m, —CH$_2$CH$_2$CH$_2$—), 3.4 (s, —C—CH$_2$C—), 3.6 (s, CH$_3$O—), 4.1 (q, CH$_3$C$\underline{H}_2$O—). Mass spectrum (m/e): 216 (M+).

EXAMPLE 2

$O^1$-Ethyl $O^6$-Methyl 3-Oxohexandioate

When the procedure of Example 1 was repeated, but using methyl 3-(chloroformyl)propionate in place of methyl 4-(chloroformyl)butyrate the crude title compound was obtained in quantitative yield as a light orange oil which was distilled to afford the pure diester, B.P. 125°–135° C. (1.5–2.5 mm.) in 48% yield. $^1$H-NMR (CDCl$_3$) ppm (delta): 1.28 (t, 3H, J=7 Hz), 2.06–3.13 (m, 4H), 3.47 (s, 2H), 3.70 (s, 3H), 4.16 (q, 2H, J=7 Hz).

EXAMPLE 3 dl-6,8-Dihydroxy-3a,4-dihydro-(2H,3H)-pyrrolo[1,2-a]quinolin-1,5-dione

In a pressure bottle were combined 48.5 g. (0.32 mole) 3,5-dimethoxyaniline, 1.4 g. platinum dioxide, 64.0 g. (0.32 mole) $O^1$-ethyl $O^6$-methyl 3-oxohexandioate and 140 ml. glacial acetic acid and shaken under hydrogen at 40–50 psi (2.8–3.5 kg./cm.$^2$) for 90 hours. The mixture was filtered through diatomaceous earth, washing with 3×40 ml. acetic acid. The combined filtrate and washings were evaporated in vacuo to obtain about 125 ml. of residue.

In a separate flask 490 ml. 48% hydrobromic acid and 270 ml. acetic acid were heated to reflux with stirring. To this was added dropwise the ~125 ml. residue from above. The addition required about 30 minutes, during which gas evolution was vigorous. The resulting mixture was refluxed for an additional 30 minutes. The flask was fitted with a distillation head and condenser and 700 ml. of distillate was collected over three hours. The residual mixture was poured onto a liter of crushed ice and the resulting red solids collected by filtration (62 g.). Extraction of the filtrate with ethyl acetate (2 liters), drying and evaporation of solvent gave an additional 7 g. of red solid. The combined red solids were dissolved in 3.5 liters of boiling methanol. Upon cooling and filtration of precipitate, 25.4 g. of light orange solids was obtained. Evaporation of the mother liquor to one liter and cooling affords an additional 10.2 g. orange solids. A third crop was collected after evaporation of the mother liquor to ~250 ml. (5.7 g.). Total yield, 41.3 g. (55.4%), M.P. 250° (decomp.). $^1$H-NMR [(CD$_3$)$_2$SO] ppm (delta): 1.5–2.3 (m, 2H), 2.4–3.8 (m, 4H), 4.0–4.7 (m, 1H), 6.0 (d, 1H, J=2.5 Hz), 7.6 (d, 1H, J=2.5 Hz), 9.3 (s, 1H), 10.4 (s, 1H). Infrared spectrum (KBr) microns: 2.9 (OH), 3.5 (OH), 5.95 (CO), 6.1 (CO).

Analysis Calculated for C$_{12}$H$_{11}$O$_4$N: C, 61.80; H, 4.75; N, 6.01. Found: C, 62.08; H, 4.95; N, 6.06.

EXAMPLE 4 dl-4a,5-Dihydro-7,9-dihydroxy-(2H,3H,4H)-pyrido[1,2-a]quinoline-1,6-dione

A. A mixture of 41.0 g. (0.19 mole) $O^1$-ethyl $O^7$-methyl 3-oxoheptandioate, 1.0 g. PtO$_2$ catalyst, 29.1 g. (0.19 mole) 3,5-dimethoxyaniline and 80 ml. glacial acetic acid was hydrogenated at 50 psi (3.5 kg./cm.$^2$) for 36 hours. The catalyst was removed by filtration, washing with acetic acid and the filtrate evaporated in vacuo to 100 ml.

This was added dropwise under nitrogen, to a refluxing mixture of 360 ml. 48% hydrobromic acid and 200 ml. glacial acetic acid. The resulting mixture was heated at reflux for 30 minutes after the addition was completed. The mixture was concentrated, under a nitrogen stream, by distillation, 500 ml. of distillate being collected over three hours. The residue was cooled to room temperature, poured onto 500 ml. ice and extracted with 4×500 ml. ethyl acetate. The extracts were dried (MgSO$_4$) and solvent evaporated in vacuo to yield 33 g. (65.5%) of 4-[2,3-dihydro-5,7-dihydroxy-(1H)-quinolin-4-one-2-yl]butyric acid as a light brown gum. $^1$H-NMR [(CD$_3$)$_2$SO] ppm (delta): 1.6–3.55 (m, 10H), 5.58 and 5.75 (2H, split doublets), 6.75 (1H, OH), 10.2 (1H, OH), 12.75 (1H, COOH). Mass spectrum (m/e): 265 M$^+$. Infrared (KBr) 5.89 microns (COOH).

Analysis Calculated for C$_{13}$H$_{15}$O$_5$N: C, 58.86; H, 5.70; N, 5.28. Found: C, 59.22; H, 5.70; N, 5.02.

B. A mixture of 26 g. (0.098 mole) 4-[2,3-dihydro-5,7-dihydroxy-(1H)-quinolin-4-one-2-yl]butyric acid and 260 ml. methanesulfonic acid was heated under a nitrogen atmosphere at 140° C. for two hours. The reaction mixture was cooled to room temperature and poured onto 1000 ml. ice. To this was added 4 liters ethyl acetate, 1 liter water, 250 g. sodium chloride and the resulting mixture stirred at room temperature overnight. The layers were separated, the aqueous phase extracted with 4×500 ml. ethyl acetate and the combined organic layers washed with saturated sodium bicarbonate solution until the pH was 7 and no effervescence was observed. The extract was then washed with water (1000 ml.), brine (1000 ml.) and dried (MgSO$_4$). The solvent was evaporated in vacuo, the residue redissolved in a small amount of hot ethyl acetate, diluted with ethyl ether and cooled to 0° C. The precipitated solid was collected by filtration and dried in vacuo to afford 9.4 g. (38.8%) of the title compound, M.P. 259°–268° C. (decomp.). $^1$H-NMR [(CD$_3$)$_2$SO] ppm (delta): 1.75–3.25 (m, 11H), 6.1 and 6.95 (2H, split doublets, meta aryl). Mass spectrum (m/e): 247 M$^+$.

Analysis Calculated for C$_{13}$H$_{13}$O$_4$N: C, 63.15; H, 5.30; N, 5.67. Found: C, 63.22; H, 5.44; N, 5.35.

EXAMPLE 5

Diastereomers of
6-Hydroxy-8-(5-phenyl-2-pentyloxy)-3a,4-dihydro(2H,3H)-pyrrolo[1,2-a]quinolin-1,5-dione Under anhydrous conditions and in a nitrogen atmosphere, 70 g. (0.30 mole) 6,8-dihydroxy-3a,4-dihydro-(2H,3H)-pyrrolo[1,2-a]quinolin-1,5-dione was dissolved in 750 ml. dimethylformamide by warming to 60° C. To the resulting deep red solution was added 51.6 g. (0.675 mole) potassium carbonate. The mixture was heated to 70° C., a solution of 2-methylsulfonyloxy-5-phenylpentane in 250 ml. dimethylformamide was added in a fast stream, and heated at 75°–80° C. for 12 hours. Additional portions of 2-methylsulfonyloxy-5-phenylpentane (5.3 g.) and potassium carbonate (3.8 g.) and heating continued at 75°–80° C. for two hours. The mixture was poured over a mixture (one liter each) ethyl acetate and ice and, after shaking in a separtory funnel, the layers were separated. The aqueous phase was extracted with 5×1000 ml. ethyl acetate. The combined organic layers were washed with 3×4 liters water, 3×2 liters of 0.5N hydrochloric acid, dried (MgSO$_4$) and concentrated to a volume of about 2.5 liters. Upon cooling, the precipitated product which formed was collected: 9.0 g., M.P. 151°–153° C. The mother liquor was concentrated to half volume, cooled, and a second crop, 34.2 g., M.P. 148°–151° C., was collected. Total yield by crystallization: 52.2 g. This material was shown to be primarily a single diastereomer, designated as "Diastereomer B." Upon recrystallization from ethyl acetate, colorless crystals were obtained, M.P. 159°–161° C. This was found to be about 90% diastereomer B. $^1$H-NMR (CDCl$_3$) ppm (delta): 1.33 (d, 3H, J=6 Hz).

The mother liquor was then evaporated to dryness in vacuo to afford 68 g. of residual oil. The oil was chromatographed on a column of silica gel (1 kg., 48–63 microns) eluting first with eight liters of 9:1 toluene-/ethyl ether then with four liters of 85:15 toluene/ethyl ether. Fractions were monitored by TLC using a 1:1 toluene/ethyl ether solvent and developing with phosphomolybdic acid. Like fractions were combined and evaporated in vacuo to afford 48.6 g. of oil which was predominantly "Diastereomer A." The total yield was 52.2 g. (B) plus 48.6 g. (A)=88.6%.

The Diastereomer A obtained above, 18 g., was triturated with ethyl acetate leaving 6.8 g. of solid material, M.P. 116°–132° C. which was found to be 3:2. Diastereomer A/Diastereomer B by NMR assay. The mother liquor from the trituration was evaporated to dryness in vacuo to obtain 11 g. of purified Diastereomer A.

EXAMPLE 6

Mixture of Diastereomers of
4a,5-Dihydro-7-hydroxy-9-(5-phenyl-2-pentyloxy)-(2H,3H,4H)-pyrido[1,2-a]quinoline-1,6-dione Under a nitrogen atmosphere and employing anhydrous conditions and reagents, a mixture of 19.5 g. (0.079 mole) dl-4a,5-dihydro-7,9-dihydroxy-(2H,3H,4H)-pyrido-[1,2-a]quinoline-1,6-dione, 24.0 g. (0.174 mole) potassium carbonate and 110 ml. dimethylformamide (DMF) is heated at 90° C. for 10 minutes, then cooled to room temperature. To this mixture was added over 5 minutes 21.0 g. (0.087 mole) 2-methylsulfonyloxy-5-phenylpentane dissolved in 20 ml. DMF. The reaction mixture was heated at 90° C. for one hour, poured into water (800 ml.) and extracted with ethyl acetate (4×500 ml.). The organic layers were combined with sodium bicarbonate solution (3×300 ml.), water (300 ml.), brine (300 ml.) and dried (MgSO$_4$). Evaporation of solvent in vacuo gave a residual yellow oil which was separated by chromatography on 1.5 kg. silica gel (0.063–0.20 mm.), eluting with 2:1 by volume toluene/ethyl ether. Fractions were monitored by TLC employing 98% ethyl ether/2% methanol:the starting material (dihydroxydione) R$_f$0.25; product, R$_f$0.40.

Similar fractions were combined and solvent evaporated in vacuo to afford 13.6 g. (43.7%) of the title compound as a viscous yellow-orange oil. $^1$H-NMR (CDCl$_3$) ppm (delta): 1.05–4.25 (m, 19H), 6.05 and 6.9 (split doublets, meta aryl), 7.02 (s, 5H), 10.9 (s, 1H). Mass spectrum (m/e): 393 M$^+$.

EXAMPLE 7 dl-6-Benzyloxy-8-(5-phenyl-2-pentyloxy)-3aS*,4-dihydro-(2H,3H)-pyrrolo[1,2-a]-quinolin-1,5-dione (Diastereomer A)

To a flask under a nitrogen atmosphere, is added 1.27 g. (26.54 mmole) sodium hydride (50% suspension in oil). The oil was removed by washing with hexane (4×250 ml.), then 125 ml. dimethylformamide (DMF) was added and the slurry cooled to 5° C. A solution of 8.76 g. (23.08 mmole) of Diastereomer A, obtained in Example 5, in 125 ml. DMF was added dropwise over 3–5 minutes while maintaining the reaction temperature at or below 8° C. The mixture was then allowed to warm to room temperature and stirred for 4 hours. The mixture was then cooled to 10° C., a solution of 4.54 g. (3.16 ml., 26.54 mmole) benzyl bromide in 30 ml. DMF added over one minute and stirred at room temperature for 17 hours. It was then poured into a mixture of 500 ml. each of water and ethyl acetate, stirred and the layers separated. The aqueous phase was extracted three times with 500 ml. portions of ethyl acetate, the combined extracts washed in turn with 500 ml. portions each of water, 0.5N hydrochloric acid, 5% aqueous sodium bicarbonate, brine, then dried (MgSO$_4$). Evaporation in vacuo gave a residual oil which was taken up in boiling ethyl ether and hot hexane carefully added (~50 ml.) to the cloud point. The mixture was cooled in ice and filtered to obtain 3.99 g. light yellow solid, collected in two crops.

The mother liquor was concentrated to dryness in vacuo and the residue, 6.5 g. separated by chromatography on a column containing 420 g. silica gel, eluting with toluene/ethyl ether. Evaporation of the product-containing fractions gave 1.2 g. of the title compound. Total yield: 5.19 g. (48%). Several crystallizations from methanol afforded pure Diastereomer A benzyl ether, M.P. 123°–124° C. $^1$H-NMR (CDCl$_3$) ppm (delta): 1.32 (d, 3H, J=6 Hz, 8-OCHC$\underline{H}_3$), 1.45–1.93 (m, 5H), 2.02–2.93 (m, 7H), 3.90–4.73 (m, 2H, 8-OC$\underline{H}$CH$_3$ and 3a-H), 5.10 (s, broad, 2H, OC$\underline{H}_2$C$_6$H$_5$), 6.23 (d, 1H, J=2 Hz, 7-$\underline{H}$), 6.88–7.77 (m, 10$\underline{H}$, phenyls), 7.97 (d, 1H, J=2 Hz, 9-$\underline{H}$). Infrared (KBr) cm$^{-1}$: 2900 (CH), 1709, 1680 (C=O).

Analysis Calculated for C$_{30}$H$_{31}$O$_4$N: C, 76.73; H, 6.65; N, 2.98. Found: C, 76.53; H, 6.68; N, 2.96.

EXAMPLE 8 dl-6-Benzyloxy-8-(5-phenyl-2-pentyloxy)-3aR*,4-dihydro-(2H,3H)-pyrrolo[1,2-a]quinoline-1,5-dione (Diastereomer B)

Employing 17.0 g. (44.81 mmole) of Diastereomer B of 6-hydroxy-8-(5-phenyl-2-pentyloxy)-3a,4-dihydro-(2H,3H)-pyrrolo[1,2-a]-pyrrolo[1,2-a]-quinolin-1,5-dione obtained in Example 5 (recrystallized solids, M.P. 158°–161° C.) in place of Diastereomer A in the procedure of the previous Example, and 2.47 g. (51.53 mmole) sodium hydride, 6.13 ml. (51.53 mmole) benzyl bromide and 1000 ml. DMF, provided 15.43 g. (73.4%) of the title compound. A purified product, M.P. 103.5°–105° C. was obtained after several recrystallizations from ethyl ether. $^1$H-NMR (CDCl$_3$) ppm (delta): 1.31 (d, 3H, J=6 Hz, 8-OCHC$\underline{H}_3$), 1.53–2.02 (m, 5H), 2.09–2.92 (m, 7H), 4.03–4.80 (m, 2H, 8-OC$\underline{H}$CH$_3$ and 3a-H), 5.11 (s, broad, 2H, OC$\underline{H}_2$C$_6$H$_5$), 6.24 (d, 1H, J=2 Hz, 7-$\underline{H}$), 6.72–7.68 (m, 10$\underline{H}$, phenyls), 7.98 (d, 1H, J=2 Hz, 9-$\underline{H}$). Infrared (KBr) cm$^{-1}$: 2900 (CH), 1690, 1650 (C=O). High resonance mass spectrum molecular ion:

Calculated for C$_{30}$H$_{31}$O$_4$N: 469.2253. Found: 469.2226.

Base peak (m/e) 91.

Analysis Calculated for C$_{30}$H$_{31}$O$_4$N: C, 76.73; H, 6.65; N, 2.98. Found: C, 76.25; H, 6.62; N, 2.88.

EXAMPLE 9 dl-6-Benzyloxy-5-hydroxy-5-ethoxycarbonylmethyl-8-(5-phenyl-2-pentyloxy)-3aS*,4-dihydro-(2H,3H)-pyrrolo[1,2-a]quinolin-1-one (Diastereomer A)

Under a nitrogen atmosphere employing anhydrous reagents and conditions, to a round bottomed flask was charged 8.24 ml. n-butyllithium (2.4M in hexane, 19.8 mmole) and tetrahydrofuran (THF), 10 ml. The mixture was cooled to −78° C., a solution of 2.78 ml. (19.8 mmole) diisopropylamine in 10 ml. THF was added dropwise over two minutes while maintaining the internal temperature below −65° C. Then a solution of 1.93 ml. (19.8 mmole) ethyl acetate in 5 ml. THF was added dropwise over 2 minutes at the same temperature (<−65° C.). When the addition was complete, the reaction mixture was stirred at −78° C. for 0.25 hour. To this was added 7.14 g. (15.2 mmole) dl-6-benzyloxy-8-(5-phenyl-2-pentyloxy)-3aS*,4-dihydro(2H,3H)-pyrrolo[1,2-a]quinoline-1,5-dione, Diastereomer A, M.P. 122°–125° C. provided in Example 7, dissolved in 80 ml. THF. This addition was also carried out below −65° C. The reaction mixture was stirred for 0.3 hour, then 1.13 ml. (19.8 mmole) acetic acid was added, followed by 75 ml. water. The organic solvents were evaporated in vacuo at room temperature, the aqueous residue diluted with 500 ml. ethyl ether and 100 ml. water, the mixture shaken and the layers separated. The ether layer was washed (150 ml. each) with 0.5N hydrochloric acid, sodium bicarbonate solution, brine, dried (MgSO$_4$) and the ether evaporated in vacuo to afford 8.37 g. of product as a colorless solid. $^1$H-NMR (CDCl$_3$) ppm (delta): 0.79–1.43 (m, 6H, methyls), 1.47–2.33 (m, 7H), 2.37–2.97 (m 6H), 6.5 (d, 1H, J=14 Hz), 3.77–4.63 (m, 4H), 4.70 (s, broad, O$\underline{H}$), 5.13 (s, broad, 2H), 6.4 (d, 1H, J=2 Hz), 7.00–7.67 (m, 10H, phenyls), 8.27 (d, 1H, J=2 Hz).

EXAMPLE 10 dl-5,6-Dihydroxy-5-Ethoxycarbonylmethyl-8-(5-phenyl-2-pentyloxy)-3aS*,4-dihydro-(2H,3H)pyrrolo[1,2-a]quinolin-1-one (Diastereomer A)

The benzyl ether obtained in the previous Example, (8.27 g., 14.85 mmole) was dissolved in 500 ml. ethanol, 6 g. palladium/carbon (5%) was added and the mixture was hydrogenated at 40–50 psi (2.8–3.5 kg./cm.$^2$) for 0.66 hour. The catalyst was removed by filtration, and the filtrate was evaporated in vacuo. The residue was taken up in methylene chloride, filtered, and evaporated in vacuo to afford 6.59 g. colorless foam (95%).

$^1$N-NMR (CDCl$_3$) ppm (delta): 1.10–1.45 (m, 6H, methyls), 1.48–2.25 (m, 7H), 2.26–2.97 (m, 6H), 3.22 (d, 1H, J=14 Hz), 3.75–4.63 (m, 4H), 5.4 (s, broad, O$\underline{H}$), 6.25 (d, 1H, J=2 Hz), 7.0–7.42 (m, 5H), 7.93 (d, 1H, J=2 Hz), 8.83 (s, broad, O$\underline{H}$).

EXAMPLE 11 dl-6-Acetoxy-5-Ethoxycarbonylmethylene-8-(5-phenyl-2-pentyloxy)-3aS*,4-dihydro-(2H,3H)-pyrrolo[1,2-a]quinolin-1-one (Diastereomer A)

The product obtained in the previous Example, 6.49 g. (13.90 mmole) was dissolved in 350 ml. methylene chloride, 30 ml. (21.5 mmole) triethylamine and 4.3 ml. (45 mmole) acetic anhydride were added and the mixture stirred at room temperature for 0.75 hours. Aqueous sodium bicarbonate solution, 50 ml., was added and the organic solvent was evaporated in vacuo. The aqueous residue was shaken with 700 ml. ethyl ether, the extract washed with 400 ml. water, 200 ml. 0.5N hydrochloric acid, 400 ml. brine and dried over anhydrous magnesium sulfate. Evaporation of the ether, in vacuo at room temperature, gave an opaque oil. This was taken up in hot methanol (~65 ml.), upon cooling a colorless solid precipitated, 5.59 g., M.P. 98°–102° C.

$^1$H-NMR (CDCl$_3$) ppm (delta): 1.03–1.47 (m, 6H), 1.49–2.12 (m, 6H), 2.17–2.32 (m, 4H), 2.33–2.87 (m, 6H), 3.63–4.70 (m, 4H), 6.27–6.50 (m, 2H), 6.97–7.53 (m, 5H), 8.40 (d, 1H, J=2 Hz).

EXAMPLE 12 dl-6-Acetoxy-5-Ethoxycarbonylmethyl-8-(5-phenyl-2-pentyloxy)-3,3aS*,4,5-tetrahydro-(2H)pyrrolo[1,2-a]quinolin-1-one (Diastereomer A)

The olefin obtained in the previous Example, 3.50 g. (7.13 mmole), was dissolved in 250 ml. ethyl acetate, 3.50 g. 5% Pd/C catalyst was added and the mixture was hydrogenated at 40–50 psi (2.8–3.5 kg./cm$^2$) for four hours. The catalyst was removed by filtration, washing with 3×80 ml. ethyl acetate. The combined filtrate and washings were evaporated in vacuo, the residual oil dissolved in 135 ml. boiling methanol and the resulting solution allowed to cool. Upon filtration, 2.32 g. of product, M.P. 94°–96° C. was obtained. The mother liquor was concentrated in vacuo to an oil, and the oil triturated with ethyl ether to provide a second crop, 0.28 g., M.P. 94°–96° C.

$^1$H-NMR (CDCl$_3$) ppm (delta): 1.025–1.308 (m, 6H), 1.325–1.858 (m, 6H), 2.075–2.342 (m, 4H), 2.350–2.733 (m, 5H), 3.062 (q, 2H, J=3, 14 Hz), 3.250–3.375 (m, 1H), 3.533–3.850 (m, 1H), 4.235 (q, 2H, J=6, 6 Hz), 4.267–4.442 (m, 1H), 6.39 (d, 1H, J=2 Hz), 7.067–7.500 (m, 5H), 8.008 (d, 1H, J=2 Hz). Infrared (KBr) cm$^{-1}$: 2900, 1830, 1760, 1690. High resonance mass spectrum: Calculated for C$_{29}$H$_{35}$O$_6$N: 493.2464. Found: 493.2445.

Analysis Calculated for C$_{29}$H$_{35}$O$_6$N: C, 70.56; H, 7.15; N, 2.84. Found: C, 70.30; N, 6.94; N, 2.68.

EXAMPLE 13 dl-6-Acetoxy-5-Ethoxycarbonylmethyl-8-(5-phenyl-2-pentyloxy)-3,3aR*,4,5-tetrahydro-(2H)-pyrrolo[1,2-a]quinolin-1-one (Diastereomer B)

When the procedure of Example 9 is carried out, but starting with Diastereomer B of dl-6-benzyloxy-8-(5-phenyl-2-pentyloxy)-3a,4-dihydro-(2H,3H)-pyrrolo[1,2-a]quinolin-1,5-dione, provided in Example 8, in place of the Diastereomer A, the corresponding product is obtained in like manner. This product is carried, in turn, through the procedures of Example 10, 11 and 12, but with the following modifications, to provide the title compound:

In the procedure of Example 10, the debenzylation was carried out with 250 ml. ethyl acetate instead of 500 ml. ethanol. The product obtained was a solid, M.P. 123°–125° C.

In the procedure of Example 11, the product obtained was a solid, M.P. 80.5°–83.5° C.

In the procedure of Example 12, the product obtained was a milky oil.

The overall yield was 78%.

EXAMPLE 14 dl-6-Acetoxy-5-(2-Acetoxyethyl)-8-(5-phenyl-2-pentyloxy)-1,2,3,3aS*,4,5-hexahydropyrrolo[1,2-a]quinoline Hydrochloride (Diastereomer A)

Under anhydrous conditions and a nitrogen atomosphere, 2.235 g. (4.53 mmole) dl-6-acetoxy-5-ethoxycarbonylmethyl-8-(5-phenyl-2-pentyloxy)-3,3aS*,4,5-tetrahydro-(2H)-pyrrolo[1,2-a]quinolin-1-one (Diastereomer A), provided in Example 12, was dissolved in 100 ml. anhydrous tetrahydrofuran, 0.688 g. (18.13 mmole) lithium aluminum hydride was added and the mixture refluxed for two hours. The mixture was cooled to −6° C. and 20 ml. 10% by weight aqueous sodium hydroxide was added dropwise over 10 minutes at such a rate that the temperature did not exceed 0° C. The resulting mixture was filtered, washing with 5×200 ml. ethyl acetate. The filtrate and washings were combined and washed with 500 ml. brine, dried (MgSO$_4$) and the solvent evaporated in vacuo to afford 1.87 g. of off-white foam. The foam was dissolved in 20 ml. methylene chloride, 2 ml. (21.1 mmole) acetic anhydride and 4 ml. (28.6 mmole) triethylamine were added and the mixture stirred overnight at ambient temperature. After addition of 600 ml. ethyl ether, the layers were separated, the ether phase was washed with 250 ml. brine, dried (MgSO$_4$) and the ether evaporated in vacuo to yield 2 g. of light green oil. Column chromatography on 110 g. silica gel (48–63 microns), eluting with two liters of 95:5 toluene/ethyl ether afforded 1.65 g. of product as the free base (oil). The free base was dissolved in 250 ml. ethyl ether and 20 ml. of hydrogen chloride saturated ethyl ether was added. The precipitated solid was collected by decantation of ether, washing with 2×25 ml. of the same solvent. Residual solvent was removed in vacuo to afford a clear glassy solid.

$^1$H-NMR (free base) (CDCl$_3$) ppm (delta): 1.27 (d, 3H), 1.38–3.54 (m, 18H), 2.03 (s, 3H), 2.29 (s, 3H), 3.88–4.40 (m, 3H), 5.92 (s, 2H), 6.92–7.64 (m, 5H). Infrared (CHCl$_3$) microns: 3.45, 5.65, 5.75. High resonance mass spectrum (M+):

Calculated for C$_{29}$H$_{37}$O$_5$N: 479.2738. Found: 479.2705.

Analysis Calculated for C$_{29}$H$_{37}$O$_5$N.HCl: C, 67.57; H, 7.38; N, 2.72. Found: C, 67.84; H, 7.42; N, 2.80.

Diastereomer B of the title compound was obtained by the same procedure and in the same yield as above, but employing as starting material the product obtained in Example 13.

EXAMPLE 15

Mixed Diastereomers of dl-7-Acetoxy-(2-Acetoxyethyl)-9-(5-phenyl-2-pentyloxy)-2,3,4,4a,5,6-hexahydro-(1H)-pyrido[1,2-a]quinoline Hydrochloride When the procedures of Examples 8 through 12 are repeated in turn, but starting with the mixture of diastereomers of 4a,5-dihydro-7-hydroxy-9-(5-phenyl-2-pentyloxy)-(2H,3H,4H)-pyrido[1,2-a]quinoline-1,6-dione in the procedure of Example 8, the title compound is obtained in like manner as a mixture of diastereomers.

EXAMPLE 16

Methyl dl-2-[1-(3,5-Dimethoxyphenyl)pyrrolidin-2-yl]Acetate

A. 2-Tetrahydrofurfuryl bromide

To 2-tetrahydrofurfuryl alcohol (20.4 g.) and triphenylphosphine (58 g.) was added over 1.5 hours 32.5 g. N-bromosuccinimide. The reaction mixture was distilled at reduced pressure to afford 20 g. of product. Redistillation gave 15 g. pure bromide, B.P. 38°–40° C. (2 mm.).

B. 2-Cyanomethyltetrahydrofuran

To a solution of 1.3 g. (5 mmole) 18-crown-6 and 9.05 g. (0.05 mole) 2-tetrahydrofurfuryl bromide in 80 ml. acetonitrile was added 16.25 g. (0.25 mole) potassium cyanide. The mixture was heated at 90° C. for 48 hours, cooled, filtered, washing with ethyl ether and the filtrate and washings evaporated in vacuo without heating. The residue was distilled to afford 4.25 g. (77%) of product, B.P. 50° C. (2 mm.). $^1$H-NMR (CDCl$_3$) ppm (delta): 2.60 (d, 2H, C$\underline{H}_2$CN).

C. 2-(Tetrahydrofuran-2-yl)acetic acid

A solution of 90 g. (0.81 mole) 2-cyanomethyltetrahydrofuran, 130 g. (3.2 mole) sodium hydroxide, 250 ml. methanol and 300 ml. water was heated at reflux for 20 hours. The reaction mixture was evaporated in vacuo, the residue taken up in chloroform and acidified to pH 5 with 6N hydrochloric acid. The organic layer was separated, the aqueous phase extracted with chloroform, the combined extracts dried (MgSO$_4$) and the solvent evaporated to give 62 g. of crude acid. Distillation afforded 52.6 g. of product, B.P. 110° C. (2 mm.). $^1$H-NMR (CDCl$_3$) ppm (delta): 2.50 (d, 2H, C$\underline{H}_2$COOH), 11.10 (s, 1H, COO$\underline{H}$).

D. Methyl 3,6-dibromocaproate

To 800 ml. glacial acetic acid saturated with anhydrous hydrogen bromide was added 56 g. 2-(tetrahydrofuran-2-yl)acetic acid in one portion and the mixture heated at 100° C. for 60 hours. The volatiles were evaporated, the residue taken up in ethyl ether and washed with water. The ether layer was dried (MgSO$_4$) and solvent evaporated to afford 120 g. of crude 3,6-dibromocaproic acid. Distillation gave 115 g. of product, B.P. 116°–124° C. (2 mm.). $^1$H-NMR (CDCl$_3$) ppm (delta): 3.00 (d, 2H, C$\underline{H}_2$COOH), 3.40 (m, 2H), 4.30 (m, 1H).

Esterification in refluxing methanolic hydrogen chloride gave 118 g. of methyl ester. $^1$H-HMR (CDCl$_3$) ppm (delta): 2.90 (d, 2H), 3.45 (m, 2H), 3.70 (s, 3H), 4.30 (m, 1H).

E. Under a nitrogen atmosphere, a mixture of 52 g. (0.340 mole) 3,5-dimethoxyaniline, 108.8 g. (0.378 mole) methyl-dl-3,6-dibromocaproate, 60 ml. pyridine and 160 ml. tetrahydrofuran were stirred at room temperature overnight. The tetrahydrofuran was distilled off at atmospheric pressure and the remaining mixture heated at 100° C. for 2.5 hours. Additional methyl dl-3,6-dibromocaproate (5.7 g.) and pyridine (3.16 ml.) was added and heating at 100° C. resumed for an additional 2.5 hours. The pyridine was evaporated in vacuo, the residue partitioned between water and methylene chloride, the aqueous phase extracted with 4×150 ml. methylene chloride and the combined organic layers washed with 75 ml. 1N hydrochloric acid, 75 ml. water and 75 ml. brine. The washed extracts were dried (MgSO$_4$) and solvent evaporated to afford 57.5 g. of orange solid.

The aqueous phase was adjusted to pH 9 with 6N sodium hydroxide, extracted with 4×100 ml. methylene chloride, the extracts washed with water, brine, dried (MgSO$_4$) and evaporated in vacuo to afford 16.7 g. of residual oil. The orange solid was placed on a silica gel column and eluted with methylene chloride/ethyl acetate.

The product fractions were combined and evaporated in vacuo to afford 53.6 g. (56%) of product. $^1$H-NMR (CDCl$_3$) ppm (delta): 3.70 (s, 3H, —COOC$\underline{H}_3$), 3.78 (s, 6H, OC$\underline{H}_3$), 5.80 (s, 3H, aromatic).

EXAMPLE 17 dl-2-[1-(3,5-Dimethoxyphenyl)pyrrolidin-2-yl]acetic Acid

A mixture of 53.6 g. (0.192 mole) methyl dl-2-[1-(3,5-dimethoxyphenyl)pyrrolidin-2-yl]acetate, 250 ml. methanol and 22.8 g. (0.57 mole) sodium hydroxide in 200 ml. water was stirred at room temperature for 2.5 hours. The methanol was evaporated and the aqueous residue cooled in ice. To this was added dropwise 48 ml. concentrated hydrochloric acid, the mixture extracted with 4×150 ml. methylene chloride, the extract washed with water, dried (MgSO$_4$) and the solvent evaporated to afford 48.9 g. (96%) of product. $^1$H-NMR (CDCl$_3$) ppm (delta): 3.80 (s, 6H, OC$\underline{H}_3$), 4.10 (m, 1H, N-C$\underline{H}$), 5.82 (s, 3H, aromatic), 11.0 (s, 1H, COO$\underline{H}$). Mass spectrum (m/e): 206 (base peak), 265 (M+).

EXAMPLE 18

Resolution via alpha-Methylbenzylamine Salt

A. Dextrorotatory salt

A mixture of 52.3 g. (0.197 mole) dl-2-[1-(3,5-dimethoxyphenyl)pyrrolidin-2-yl]acetic acid and 370 ml. ethyl acetate was heated to affect solution, 24.4 g. (0.201 moles) d-(+)-alpha-methylbenzylamine was added. The mixture was stirred for 10 minutes, then allowed to stand at room temperature for three hours to initiate crystallization. Then 370 ml. ethyl ether was added and the resulting mixture refrigerated overnight. Filtration and washing with cold ether gave 72.2 g. of solids. Evaporation of the mother liquors afforded an additional 4.7 g. of brown solid.

To the first crop (72.2 g.) was added 1440 ml. ethyl acetate and the mixture heated until a solution was obtained. The solution was allowed to stand overnight at room temperature, filtered, the crystals washeed with cold ether and dried in vacuo to afford 40.9 g., M.P. 129°–130° C., [alpha]$_D$+13.5°. After two recrystallizations from ethyl acetate, 9.7 g. of pure salt was obtained, M.P. 141°–142° C., [alpha]$_D$+32°.

B. Levorotatory salt

The mother liquors from above were acidified with 167 ml. 1N hydrochloric acid, extracted with 5×125 ml. ethyl acetate, the extracts combined, washed with brine, dried (MgSO$_4$) and the solvent evaporated to obtain 49 g. of residue. This was dissolved in 350 ml. warm ethyl acetate, 22.4 g. l-(−)-alpha-methylbenzylamine added and the solution cooled to room temperature. Ethyl ether, 350 ml. was added and the mixture refrigerated overnight. The precipitated solid was collected by filtration, washed with cold ether and dried in vacuo to obtain 44.0 g. of salt. This was dissolved in 880 ml. ethyl acetate and set aside at room temperature for six hours. Filtration gave 12.4 g., M.P. 139°–140° C.

After standing overnight, the mother liquor afforded a second crop, 11.66 g., M.P. 139°–140° C. The optical rotation (in chloroform) for the first crop was [alpha]$_D$−30.9°, and [alpha]$_D$−26.6° for the second crop.

The two crops were combined and recrystallized from 480 ml. ethyl acetate to afford 18.0 g. of salt, M.P. 141°–142° C., [alpha]$_D$−34.4°.

EXAMPLE 19

A. d-(+)-2-[1-(3,5-dimethoxyphenyl)pyrrolidin-2-yl]acetic acid

The dextrorotatory salt, obtained in the previous Example, 22.0 g., was recrystallized from ethyl acetate (440 ml.) to obtain 17.5 g. of salt, M.P. 142°–143° C., [alpha]$_D$+33.8°. This was treated with 47 ml. 1N hydrochloric acid, extracted with 4×100 ml. ethyl acetate, and the extracts washed with brine and dried over magnesium sulfate. Evaporation of solvent in vacuo gave 12.9 g. of d-(+)-acid as a green oil. A portion was decolorized by passing it through a short column of silica gel, [alpha]$_D$+31.4°.

B. l-(−)-2-[1-(3,5-dimethoxyphenyl)pyrrolidin-2-yl]acetic acid

To 18.0 g. of the levorotatory salt obtained in the previous Example, was added 46.5 ml. 1N hydrochloric acid and the resulting mixture worked up as in Part A, above, to obtain 13.2 g. of product [alpha]$_D$−36.4°.

EXAMPLE 20 dl-, d-(+)- and l-(−)-6,8-Dimethoxy-2,3,3a,4-tetrahydro-1H-pyrrolo[1,2-a]quinolin-5-one A. Dextrorotatory isomers A mixture of 13.2 g. (46.5 mmole) l-(−)-2-[1-(3,5-dimethoxyphenyl)pyrrolidin-2-yl]acetic acid, 6.5 g. sodium acetate, 100 ml. acetic acid and 100 ml. acetic anhydride was heated on the steam bath for 35 minutes. The volatiles were evaporated in vacuo, the residue mixed with methylene chloride, and the organic layer separated. After washing the organic phase with sodium bicarbonate solution (3×50 ml.), drying (MgSO$_4$) and evaporation of solvent, 11.2 g. (91%) of crude product was obtained. A 300 mg. portion was crystallized from methylene chloride/hexane, m.p. 126°–127° C., [alpha]$_D$+141° (c=1, CHCl$_3$). Mass spectrum (m/e): 247M+.

B. Levorotatory isomers

A mixture of 12.9 g. (48.6 mole) d-(+)-2-[1-(3,5-dimethoxyphenyl)pyrrolidin-2-yl]acetic acid, 6.4 g. sodium acetate and 50 ml. each of acetic acid and acetic anhydride gave 11.2 g. of crude product by the above procedure. Recrystallization of a portion from methylene chloride gave purified isomer, m.p. 129°–130° C., [alpha]$_D$−146.2° (c=1, CHCl$_3$).

Racemate

By the same procedure, dl-2-[1-(3,5-dimethoxyphenyl)pyrrolidin-2-yl]acetic acid is converted to dl-6,8-dimethoxy-2,3,3a,4-tetrahydro-1H-pyrrolo[1,2-a]quinolin-5-one.

EXAMPLE 21 dl-, d-(+)- and l-(−)-6,8-Dihydroxy-2,3,3a,4-tetrahydro-1H-pyrrolo[1,2-a]quinolin-5-one A. Dextrorotatory isomer A mixture of 11.2 g. (45.3 mmole) d-(+)-6,8-dimethoxy-2,3,3a,4-tetrahydro-1H-pyrrolo[1,2-a]quinolin-5-one and 100 ml. each of acetic acid and 48% hydrobromic acid was heated under a nitrogen atmosphere at 67° C. for 2.5 hours. The reaction mixture was concentrated by vacuo, the residue mixed with water and adjusted to pH 7.0 with sodium bicarbonate solution. The neutral mixture was extracted with 6×100 ml. ethyl acetate, the combined extracts washed with brine, dried (MgSO$_4$) and the solvent evaporated in vacuo to afford 9.0 g. (91%) of product as a yellow solid. A 100 mg. sample was crystallized from chloroform, m.p. 202°–203° C., [alpha]$_D$+109° (c=1, CHCl$_3$). Mass spectrum (m/e): 218 (base peak), 219 (M+).

B. Levorotatory isomer

By the same procedure 10.2 g. l-(−)-6,8-dimethoxy-2,3,3a,4-tetrahydro-1H-pyrrolo[1,2-a]quinolin-5-one and 50 ml. each of acetic acid and 48% hydrobromic acid afforded 9.2 g. of product, m.p. 190°–192° C., [alpha]$_D$−91.4° (c=1, CHCl$_3$).

Racemate

By the same procedure dl-6,8-dimethoxy-2,3,3a,4-tetrahydro-1H-pyrrolo[1,2-a]quinolin-5-one is converted to dl-6,8-dihydroxy-2,3,3a,4-tetrahydro-1H-pyrrolo[1,2-a]quinolin-5-one.

EXAMPLE 21C

6-Hydroxy-8-(5-phenyl-2R-pentyloxy)-2,3,3aS,4-tetrahydro-1H-pyrrolo[1,2-a]quinolin-5-one A mixture of 7.4 g. (33.8 mmole) d-(+)-6,8-dihydroxy-2,3,3a,4-tetrahydro-1H-pyrrolo[1,2-a]quinolin-5-one, 9.55 g. (69.2 mmole) powdered potassium carbonate and 37 ml. dimethylformamide was heated to 80° C. under a nitrogen atmosphere, 8.391 g. (34.6 mmole) 5-phenyl-2S-pentyl mesylate is added and heating at 80° C. continued for 90 minutes. The dimethylformamide was evaporated in vacuo, the residue extracted with 5×50 ml. methylene chloride and the combined extracts washed with water, brine, and dried (MgSO$_4$). Evaporation of solvent in vacuo afforded 13.7 g. of crude product which was purified on a column of silica gel, eluting with a mixture of equal volumes of methylene chloride and hexane and methylene chloride/ethyl acetate. The product fractions were combined and evaporated to provide 8.52 g. of the desired product. $^1$H-NMR (CDCl$_3$) ppm (delta): 1.30 (d, 3H), 5.35 (m, 1H), 5.65 (m, 1H), 7.1 (s, 5H), 12.7 (s, 1H, OH).

By the above method the appropriate racemic or optically active dihydroxy compound of the preceding Example is reacted with the appropriate racemic or optically active 5-phenyl-2-pentyl mesylate to produce:

2,3,3a,4-tetrahydro-6-hydroxy-8-(5-phenyl-2-pentyloxy)-1H-pyrrolo[1,2-a]quinolin-5-one, as a mixture of two racemates;

2,3,3aR,4-tetrahydro-6-hydroxy-8-(5-phenyl-2R-pentyloxy)-1H-pyrrolo[1,2-a]quinolin-5-one;

2,3,3aR,4-tetrahydro-6-hydroxy-8-(5-phenyl-2S-pentyloxy)-1H-pyrrolo[1,2-a]quinolin-5-one; and 2,3,3aS,4-tetrahydro-6-hydroxy-8-(5-phenyl-2S-pentyloxy)-1H-pyrrolo[1,2-a]quinolin-5-one.

EXAMPLE 21D

6-Acetoxy-8-(5-phenyl-2R-pentyloxy)-2,3,3aS,4-tetrahydro-1H-pyrrolo[1,2-a]quinolin-5-one A mixture of 3.138 g. (8.6 mmole) of the 6-hydroxy compound obtained in the preceding Example, 30 ml. pyridine and 9 ml. acetic anhydride was heated, under nitrogen, at 80° C. overnight. The pyridine was removed by evaporation in vacuo, the residue taken up in methylene chloride, washed with water and dried (MgSO₄). Evaporation of solvent afforded a residual oil which was purified by chromatography on a silica gel column, eluting with methylene chloride. The product-containing fractions were combined and the solvent evaporated in vacuo to provide 2.193 g. of the desired product. Reaction of the combined less polar fractions (1.11 g.) with fresh acetic anhydride by the above procedure and work-up as above gave an additional 1.105 g. of product. $^1$H-NMR (CDCl₃) ppm (delta): 1.30 (d, 3H), 2.30 (s, 3H), 5.80 (s, 2H, aromatic), 7.20 (s, 5H, phenyl).

EXAMPLE 21E

6-Hydroxy-5-Carboxymethylene-8-(5-phenyl-2R-pentyloxy)-2,3,3aS,4-tetrahydro-1H-pyrrolo[1,2-a]quinoline Lactone Under a nitrogen atmosphere and anhydrous conditions 70 ml. dry tetrahydrofuran was cooled to −5° C. and 1.490 g. (14.76 mmole) diisopropylamine was added followed by dropwise addition of 9.22 ml. (14.76 mmole) n-butyllithium in hexane while keeping the mixture below 0° C. After the addition was completed, the mixture was stirred at −5° C. for 30 minutes and cooled to −67° C. Ethyl acetate (648 mg., 7.36 mmole) was added dropwise while keeping the reaction mixture below −67° C. After the addition, the resulting mixture was stirred for −67° C. for one hour. To this was added 1.989 g. (4.9 mmole) of the 6-acetoxy compound, obtained in the preceding Example, dissolved in 10 ml. tetrahydrofuran and the resulting mixture stirred at −74° C. for 3.5 hours. Acetic acid was added to adjust the mixture to pH 5.5. After allowing to warm to room temperature, the mixture was extracted with methylene chloride, the combined extracts washed with water, dried (MgSO₄) and the solvent evaporated at reduced pressure. The residual oil was chromatographed on silica gel, eluting with methylene chloride/hexane and finally with ethyl acetate. Product fractions were combined and evaporated to dryness to yield 1.13 g. of the title lactone. $^1$H-NMR (CDCl₃) ppm (delta): 1.30 (d, 3H), 5.70 (m, 2H, aromatic), 6.05 (m, 1H, olefin), 7.10 (s, 5H, phenyl).

Acetylation of one of the remaining 6-hydroxy compounds provided in Example 21C by the procedure of Example 21D and reaction of the 6-acetoxy compound by the above method likewise produces compounds of the formula below

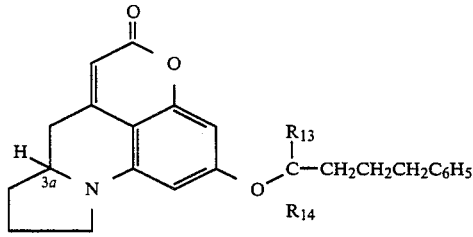

where the absolute or relative stereochemistry at position 3a and at the carbon bearing R₁₃ and R₁₄ is

| 3a | CR₁₃R₁₄ |
|----|---------|
| R  | R       |
| R  | S       |

-continued

| 3a | CR₁₃R₁₄ |
|----|---------|
| S  | S       | and as a mixture of two racemates.

EXAMPLE 21F

2-[6-Hydroxy-8-(5-phenyl-2R-pentyloxy)-1,2,3,3aS,4,5R-hexahydropyrrolo[1,2-a]quinolin-5-yl]acetic Acid Lactone A solution of 1.157 g. (2.98 mmole) of the unsaturated lactone obtained in the previous Example in 100 ml. methanol was heated to 50° C., and 15 ml. 5N sodium hydroxide and 1.41 g. of Raney alloy was added, the latter being added in portions over about five minutes. The mixture was then stirred at 55° C. for 3.5 hours, filtered to remove the Raney alloy, the cake washed with methanol and the solvent evaporated in vacuo. To the residue, 75 ml. 1N hydrochloric acid was added, the precipitated solid was extracted with ethyl acetate, the extracts dried (MgSO₄) and evaporated to obtain 622 mg. of crude product as an oil. The oil was purified by chromatography on silica gel, eluting with methylene chloride (15 fractions), ethyl acetate (3 fractions) and stripping the column with methanol, the product containing fraction combined (fractions 2-10) and evaporated in vacuo to provide 322 mg. of the desired lactone. $^1$H-NMR (CDCl₃) ppm (delta): 1.30 (d, 3H), 4.15 (m, 1H), 5.57–5.93 (m, 2H), 7.08 (s, 5H).

By reduction of the appropriate racemic or optically active unsaturated lactone provided in the previous Example by the above procedure, the following saturated lactones are obtained:

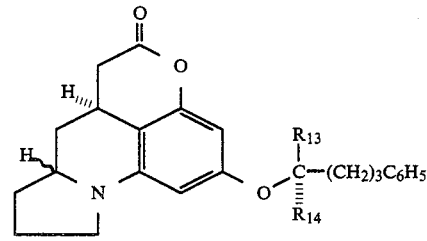

where the absolute or relative stereochemistry at position 3a and at the carbon atom bearing R₁₃ and R₁₄ is as a mixture of two racemates or as shown below.

| 3a | CR₁₃R₁₄ |
|----|---------|
| R  | R       |
| R  | S       |
| S  | S       |

EXAMPLE 21G

6-Hydroxy-5-(2-Hydroxyethyl)-8-(5-phenyl-2R-pentyloxy)-1,2,3,3aS*,4,5R*-hexahydropyrrolo[1,2-a]quinoline A mixture of 10 ml. dry tetrahydrofuran and 340 mg. (0.87 mmole) of the saturated lactone obtained in the preceding Example was stirred to affect solution, 33 mg. (0.87 mmole) lithium aluminum hydride added and the mixture stirred at room temperature for two hours. The reaction was quenched by addition of a few drops of water, the pH adjusted to 6.0 with 1N hydrochloric acid and the mixture extracted with ethyl acetate. The combined extracts were washed with brine, dried (MgSO4) and the solvent evaporated in vacuo to afford 344 mg. residual oil. The oil was placed on a silica gel column and eluted with methylene chloride/ethyl acetate and stripped with methanol. Product fractions were combined and evaporated to dryness in vacuo to yield 323 mg. of an oil, [alpha]$_D$+46.5 (c=1, CHCl3). $^1$H-NMR (CDCl3) ppm (delta): 1.20 (d, 3H), 3.60 (t, 2H, CH2OH), 4.10 (m, 1H), 5.65 (m, 2H), 7.10 (s, 5H).

Lithium aluminum hydride reduction of the remaining 5-phenyl-2-pentyloxy-saturated lactones provided in the preceding Example similarly provides:

6-hydroxy-5-(2-hydroxyethyl)-8-(5-phenyl-2-pentyloxy)-1,2,3,3a,4,5R-hexahydropyrrolo[1,2-a]quinoline as a mixture of two racemates;

6-hydroxy-5-(2-hydroxyethyl)-8-(5-phenyl-2R-pentyloxy)-1,2,3,3aR*,4,5R*-hexahydropyrrolo[1,2-a]quinoline;

6-hydroxy-5-(2-hydroxyethyl)-8-(5-phenyl-2S-pentyloxy)-1,2,3,3aR*,4,5R*-hexahydropyrrolo[1,2-a]quinoline; and 6-hydroxy-5-(2-hydroxyethyl)-8-(5-phenyl-2S-pentyloxy)-1,2,3,3aS*,4,5R*-hexahydropyrrolo[1,2-a]quinoline.

EXAMPLE 22

Methyl dl-2-[1-(3,5-dimethoxyphenyl)piperidin-2-yl]acetate

A. 2-Cyanomethyltetrahydropyran

Repeating the procedure of Example 16, Part B, but employing 2-chloromethyltetrahydropyran in place of 2-tetrahydrofurfuryl bromide and heating for 6 days gave a 52% yield of product, B.P. 65°-74° C. (3 mm.). $^1$H-NMR (CDCl3) ppm (delta): 2.50 (d, 2H, CH2CN).

B. 2-(Tetrahydropyran-2-yl)acetic acid

Alkaline hydrolysis of the above nitrile by the procedure of Example 16, Part C, gave the desired product, M.P. 46°-50° C. in 77% yield.

C. Methyl 3,5-dibromoheptanoate

Treatment of the above acid with HBr/acetic acid by the procedure of Example 16, Part D gave a 94% yield of 3,7-dibromoheptanoic acid. $^1$H-NMR (CDCl3) ppm (delta): 2.90 (d, 2H), 4.30 (m, 1H), 11.30 (s, 1H).

The dibromo acid was esterified in methanol saturated with dry hydrogen chloride to give the desired methyl ester in 95% yield. $^1$H-NMR (CDCl3) ppm (delta): 3.95 (d, 2H, CH2COOCH3), 4.35 (m, 1H, 3-position), 4.75 (s, 3H, COOCH3).

D. By the procedure of Example 16, 23.7 g. (0.155 mole) 3,5-dimethoxyaniline and 52.3 g. (0.173 mole) of methyl 3,7-dibromoheptanoate, 26.9 g. pyridine and 80 ml. tetrahydrofuran (THF) were combined and stirred overnight at room temperature. The THF was removed by distillation at atmospheric pressure and an additional 5.8 g. 3,7-dibromoheptanoate and 3.3 g. of pyridine were added. The mixture was heated at 100° C. for five hours, then concentrated in vacuo. The residue was dissolved in methylene chloride and worked up as described in Example 16 to afford 38 g. of crude product. The crude material was taken up in toluene and placed on a column of 400 g. of silica gel and eluted with ethyl acetate/methanol. Product fractions were combined and evaporated to dryness to give 14.6 g. of material: $^1$H-NMR (CDCl3) ppm (delta): 2.58 (d, 2H, CH2CO2CH3), 3.64 (s, 3H, CO2CH3), 3.78 (s, 6H, OCH3), 4.30 (m, 1H, —NCH—CH2CO2CH3), 6.2-5.8 (m, 3H, aromatic).

EXAMPLE 23 d-, l- and dl-2-[1-(3,5-Dimethoxyphenyl)piperidin-2-yl]acetic Acid

A mixture of 14.5 g. (0.049 mole) methyl dl-2-[1-3,5-dimethoxyphenyl)piperidin-2-yl]acetate, 49 ml. 5N sodium hydroxide and 100 ml. methanol was stirred at room temperature overnight. Water, 250 ml. was added, the mixture acidified with 1N hydrochloric acid to pH 5 and extracted with ethyl acetate. The extracts were combined, washed with brine, dried (MgSO4) and evaporated in vacuo to yield 12.2 g. (90%) of dl product as an oil. $^1$H-NMR (CDCl3) ppm (delta): 2.55 (d, 2H, CH2COOH), 3.80 (s, 6H), 6.30-5.80 (m, 3H), 11.0 (s, 1H, COOH).

By the methods of Examples 18 and 19, the above acid is resolved into its enantiomeric forms:

d-2-[1-(3,5-dimethoxyphenyl)piperidin-2-yl]acetic acid; and l-2-[1-(3,5-dimethoxyphenyl)piperidin-2-yl]acetic acid.

EXAMPLE 24 d-, l- and dl-3,4,4a,5-tetrahydro-7,9-dimethoxy-1H,2H-pyrido[1,2-a]quinolin-6-one Under a nitrogen atmosphere, a mixture of 12.1 g. (0.043 mole) dl-2-[1-(3,5-dimethoxyphenyl)piperidin-2-yl]acetic acid, 100 ml. glacial acetic acid, 6.0 g. sodium acetate and 100 ml. acetic anhydride was stirred at room temperature overnight. The acetic acid and acetic anhydride were removed by evaporation in vacuo, the residue partitioned between methylene chloride and saturated aqueous sodium bicarbonate solution, and the organic phase washed with sodium bicarbonate, water, brine and dried (MgSO4). The extracts were evaporated to dryness to give 13 g. of a green oil. The oil was purified by chromatography on a column containing 300 g. of silica gel, eluting with ethyl acetate. Product fractions were combined and evaporated to afford 5.5 g. of the desired dl product, M.P. 91°-94° C. $^1$H-NMR (CDCl3) ppm (delta): 2.50 (m, 2H, CH2CO), 3.79 (s, 3H), 3.81 (s, 3H), 5.90 (m, 2H). After recrystallization from isopropyl ether, 2.6 g. of crystals were obtained, M.P. 92°-93° C.

By the same method, the optically active acids of the preceding Example are converted to the corresponding d- and l-forms of the title product.

EXAMPLE 25 dl-6-Ethoxycarbonylmethyl-6-hydroxy-7,9-dimethoxy-1,2,3,4,4a,5-hexahydropyrido[1,2-a]quinoline To a solution of 5.05 g. (0.05 mole) diisopropylamine in 100 ml. tetrahydrofuran (THF) under a nitrogen atmosphere and anhydrous conditions at 0° C. was added dropwise 31.25 ml. (0.05 mole) 1.6M n-butyllithium in hexane, the mixture stirred at 0° C. for 20 minutes, then cooled to −78° C. A solution of 4.4 g. (0.05 mole) ethyl acetate in 20 ml. THF was added dropwise, the resulting mixture stirred at −78° C. for one hour, then a solution of 3.0 g. (0.0115 mole) dl-7,9-dimethoxy-6-oxo-1,2,3,4,4a,5-hexahydropyrido[1,2-a]quinoline in 20 ml. THF was added dropwise over 30 minutes. The mixture was stirred for 15 minutes after the addition was completed, quenched by addition of 3.6 g. acetic acid at −78° C. and poured into water. Extraction with ethyl ether and evaporation of solvent from the extracts gave 4.0 g. of crude product. This was purified by chromatography on 200 g. silica gel, eluting with ethyl ether afforded 3.0 g. of purified product. $^1$H-NMR (CDCl$_3$) ppm (delta): 1.35 (t, 3H), 4.20 (q, 2H), 4.70 (s, 1H, OH), 5.90 (m, 2H, aromatic).

The less polar chromatography fractions were combined and evaporated to dryness to give 600 mg. of olefinic material.

EXAMPLE 26

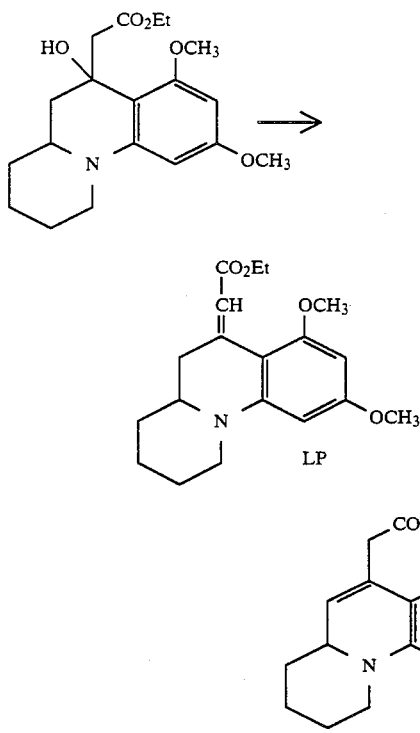

To a suspension of 6 g. of florisil in 30 ml. benzene was added 3.0 g. of dl-6-ethoxycarbonylmethyl-6-hydroxy-7,9-dimethoxy-1,2,3,4,4a,5-hexahydropyrido[1,2-a]quinoline and the mixture was heated at reflux for two hours. Thin-layer chromatography of a sample on a silica gel plate, eluting with ethyl ether showed two spots, $R_f$ 0.7 and 0.5, identical to the less polar fraction (600 mg.) obtained in the previous Example.

The above reaction mixture was filtered to remove florisil and the benzene evaporated to give 2.6 g. of crude material which was combined with the less polar mixture (600 mg.) from the previous Example. The crude mixture (3.2 g.) was placed on a silica gel column and eluted with hexane/ethyl ether to afford 1.5 g. of LP product ($R_f$ 0.7) with infrared carbonyl band at 1715 cm$^{-1}$ and 1.5 g. of MP material ($R_f$ 0.5) with infrared carbonyl band at 1750 cm$^{-1}$.

The LP product was identified by its $^1$H-NMR spectrum as dl-6-ethoxycarbonylmethylene-7,9-dimethoxy-1,2,3,4,4a,5-hexahydropyrido[1,2-a]quinoline.

The MP product was likewise identified as dl-6-ethoxycarbonylmethyl-7,9-dimethoxy-2,3,4,4a-tetrahydro-(1H)-pyrido[1,2-a]quinoline.

EXAMPLE 27 dl-6-Carboxymethyl-7,9-dimethoxy-2,3,4,4a,5,6-hexahydro-1H-pyrido[1,2-a]quinoline In a flask equipped with magnetic stirrer, condenser and nitrogen inlet was placed 986 mg. (2.97 mole) dl-6-ethoxycarbonylmethylene-7,9-dimethoxy-1,2,3,4,4a,5-hexahydropyrido[1,2-a]quinoline and 130 ml. absolute methanol. The mixture was warmed to 40° C., then 74 ml. 1N sodium hydroxide was added dropwise, the temperature was increased to 45°–50° C. and 1.39 g. Raney alloy was added in portions. The resulting mixture was stirred 70 minutes, allowed to cool, filtered and the filtrate evaporated. The liquid residue was partitioned between water and chloroform, acidified to pH 5 with 1N hydrochloric acid, shaken and the layers separated. The aqueous layer was reextracted with chloroform and the combined organic phase washed with brine and dried (MgSO$_4$). The solvent was evaporated to obtain 826 mg. of crude product. Mass spectrum (m/e): 305 (M+), 246 (M—CH$_2$COOH).

Employing the corresponding d- and l-forms of 3,4,4a,5-tetrahydro-7,9-dimethoxy-1H,2H-pyrido[1,2-a]quinolin-6-one provided in Example 24, as starting material in the procedure of Example 25 and carrying the product, thus obtained, through to procedures of Examples 26 and 27 the following compounds are similarly obtained:

6-carboxymethyl-7,9-dimethoxy-2,3,4,4aR*,5,6S*-hexahydro-1H-pyrido[1,2-a]quinoline and
6-carboxymethyl-7,9-dimethoxy-2,3,4,4aS*,5,6S*-hexahydro-1H-pyrido[1,2-a]quinoline.

EXAMPLE 28

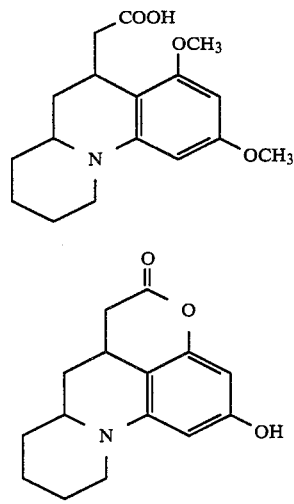

In a flask fitted with magnetic stirrer and dry ice condenser was placed 826 mg. dl-6-carboxymethyl-7,9-dimethoxy-2,3,4,4a,5,6-hexahydro-(1H)-pyrido[1,2-a]quinoline, 50 ml. glacial acetic acid and 50 ml. 48% hydrobromic acid. The flask was heated at 100° C. for 24 hours and the reaction mixture evaporated. The residue was diluted with water, adjusted to pH 6–7 with 6N sodium hydroxide, the mixture saturated with sodium chloride and extracted with ethyl acetate. The extracts were dried (Na$_2$SO$_4$) and solvent evaporated in vacuo to provide the crude title compound as an oily foam, 702 mg. This was purified by chromatography on a column of silica gel, eluting with chloroform/ethyl ether. The product-containing fractions were combined and evaporated to yield 390 mg. Mass spectrum (m/e): 259 (M+), $^1$H-NMR (CDCl$_3$) ppm (delta): 1–4 (m, 15H, aliphatic and OH), 6.0 (m, 2H, aromatic).

EXAMPLE 29

Lactone of dl-6-Carboxymethyl-7-hydroxy-9-(5-phenyl-2-pentyloxy)-2,3,4,4a,5,6-hexahydro[1H]pyrido[1,2-a]quinoline

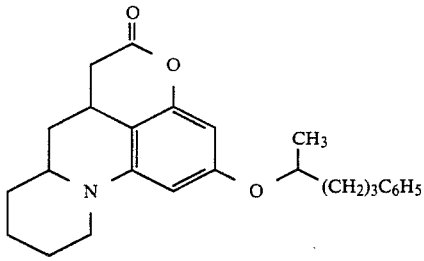

In a flame dried flask equipped with magnetic stirrer, condenser and nitrogen inlet capillary was placed a solution of 390 mg. (1.5 mmole) dl-6-carboxymethyl-7,9-dihydroxy-2,3,4,4a,5,6-hexahydro(1H)pyrido[1,2-a]quinoline lactone in 3 ml. dimethylformamide followed by 500 mg. (3.62 mmole) powdered potassium carbonate. The resulting mixture was heated at 70° C. for 30 minutes, a solution of 452 mg. (1.95 mmole) dl-5-phenyl-2-methylsulfonyloxypentane in 2 ml. dimethylformamide was added and the mixture was heated at 80° C. for 3.5 hours. An additional 135 mg. of dl-5-phenyl-2-methylsulfonyloxypentane in one ml. DMF was added and heating at 80° C. continued for a further 1.8 hours. The reaction mixture was allowed to cool and stirred at room temperature overnight. The mixture was again heated to 80° C., 250 mg. of potassium carbonate (powder) was added, and the mixture held at 80° C. for 4 hours. Another increment (135 mg.) of dl-5-phenyl-2-methylsulfonyloxypentane in 1 ml. DMF was added, heating continued for one hour and the mixture again stirred overnight at room temperature. The mixture was combined with water, extracted with ethyl acetate and the combined extracts washed with water, brine and dried (MgSO$_4$). Evaporation of solvent in vacuo afforded a brown oil which was purified by chromatography on a silica gel column (50 g., 70–230 mesh) packed with chloroform and eluted with the same solvent. The product-containing fractions were combined and rechromatographed, eluting with isopropyl ether/hexane, 2:1 to provide 263 mg. of the desired product. The $^1$H-NMR spectrum was consistent with the structure of the title compound: 1.30 (d, 3H), 4.15 (m, 1H), 5.95–6.25 (m, 2H, aromatic), 7.20 (s, 2H, phenyl), peaks, ppm (delta).

EXAMPLE 30 dl-6-(2-Hydroxyethyl)-7-hydroxy-9-(5-phenyl-2-pentyloxy)-2,3,4,4a,5,6-hexahydro(1H)pyrido[1,2-a]quinoline and Diacetate A. Under a nitrogen atmosphere and anhydrous conditions, to a solution of 263 mg. (0.65 mmole) the lactone of dl-6-carboxymethyl-7-hydroxy-9-(5-phenyl-2-pentyloxy)-2,3,4,4a,5,6-hexahydro(1H)pyrido[1,2-a]quinoline in 20 ml. tetrahydrofuran (THF) was added in portions over three minutes, 25 mg. (0.66 mmole) lithium aluminum hydride. The resulting mixture was stirred at ambient temperature overnight. The reaction was quenched by addition of water, the pH adjusted to 6.0 with 1N hydrochloric acid and the mixture partitioned between water and ethyl acetate. The combined organic layers were washed with brine, dried (MgSO$_4$) and evaporated to dryness to provide 275 mg. of the desired dihydroxy compound as an oil.

B. The product of Part A, 266 mg. (0.65 mmole) was dissolved in 10 ml. methylene chloride and 1.8 ml. pyridine. To this was added 0.6 ml. acetic anhydride and the mixture was stirred under nitrogen at room temperature for 48 hours. The reaction mixture was concentrated in vacuo, the residue dissolved in ethyl acetate, washed with water, brine and dried (MgSO$_4$). Evaporation of solvent gave 317 mg. of crude product. This was purified by chromatography on 50 g. silica gel (70–230 mesh), eluting with chloroform. Fractions 3–8 were combined and evaporated to dryness to yield 215 mg. of the purified diacetate. $^1$H-NMR (CDCl$_3$) ppm (delta): 1.30 (d, 3H), 2.05 (s, 3H, acetate), 2.30 (s, 3H, phenolic acetate), 6.05 (d, 1H), 6.20 (broad singlet, 1H), 7.20 (s, 5H); mass spectrum (m/e): 493 (M+), 406 (M—CH$_2$C-H$_2$OCOCH$_3$).

C. To 10 ml. methanol was added 0.79 ml. 1N sodium hydroxide solution and 187 mg. (0.38 mmole) of the diacetate obtained in Part B, above. The reaction mixture was stirred under nitrogen, in the dark for two hours. The mixture was neutralized with 1N hydrochloric acid, evaporated to dryness, the residue taken up in ethyl ether, washed with water and dried (MgSO$_4$). Evaporation of ether gave 148 mg. of dihydroxy compound. Mass spectrum (m/e): 409 (M+), 364 (M—CH$_2$CH$_2$OH). $^1$H-NMR (CDCl$_3$) ppm (delta): 1.30 (d, 3H), 5.90 (s, 2H, aromatic), 7.20 (s, 5H, phenyl).

EXAMPLE 31

3,5-Dimethoxy-beta-Nitrostyrene

A solution of 34.5 g. (0.208 mole) 3,5-dimethoxybenzaldehyde and 12.68 g. (0.208 mole) nitromethane in 40 ml. methanol was cooled to 0° C. under a nitrogen atmosphere. To this was added dropwise a cold solution of 8.43 g. (0.211 mole) sodium hydroxide in 30 ml. water and stirring continued at 0° C. for 15 minutes after the addition was completed. The mixture was diluted with ice-water and added slowly to a solution of 40 ml. concentrated hydrochloric acid in 60 ml. water. The precipitated product (44 g.) was collected by filtration and recrystallized from methanol to give 28.6 g., M.P. 132° C. J. Org. Chem., 27, 376 (1976) reported M.P. 133.5°–134.5° C.

EXAMPLE 32

4-(3,5-Dimethoxyphenyl)-5-Nitrocyclohexene

A stainless steel pressure vessel was charged with 28.6 g. (0.137 mole) 3,5-dimethoxy-beta-nitrostyrene, 20 g. (0.378 mole) butadiene, 40 ml. toluene and a few crystals of hydroquinone. The vessel was cooled to −78° C. under a nitrogen atmosphere and sealed. The sealed vessel was heated at 100° C. for 48 hours, cooled and the reaction mixture concentrated under nitrogen. The residual solid was crystallized from methanol to afford 29.8 g. of title compound, M.P. 80.5°–82° C. J. Org. Chem., 27, 376 (1962) reported M.P. 73°–75° C. $^1$H-NMR (CDCl$_3$) ppm (delta): 3.75 (s, 6H, OCH$_3$), 4.95

(m, 1H, C$\underline{H}$NO$_2$), 5.75 (s, 2H, olefin), 6.40 (s, 3H, aromatic).

EXAMPLE 33

2-(3,5-Dimethoxyphenyl)-4-Cyclohexen-1-one

This product was obtained from 28.7 g. (0.109 mole) 4-(3,5-dimethoxyphenyl)-5-nitrocyclohexene in the Nef reaction using the procedure of Wildman, *J. Org. Chem.*, 17, 588 (1952) for preparing 6-phenyl-3-cyclohexen-1-ones. After recrystallization of the crude product from isopropanol/ethyl ether, 23.6 g. of the title compound was obtained, M.P. 60°–62° C., lit. [*J. Org. Chem.* 27, 376 (1962)], M.P. 65.5°–66.6° C.

EXAMPLE 34

2-(3,5-Dimethoxyphenyl)Cyclohexanone

A mixture of 23.6 g. 2-(3,5-dimethoxyphenyl)-4-cyclohexen-1-one, 300 ml. ethanol and 3 g. 10% Pd/C catalyst was hydrogenated at 40 psi (2.8 kg./cm.$^2$). After hydrogen uptake ceased, the mixture was filtered, the filtrate evaporated in vacuo and the residue recrystallized from isopropyl ether to obtain 17 g. of product, M.P. 61°–62° C., lit. [*J. Org. Chem.*, 27, 376 (1962)], M.P. 62.5°–63° C.

EXAMPLE 35

2-(3,5-Dimethoxyphenyl)-1-(Methoxycarbonylmethylene)Cyclohexane

To a suspension of 3.9 g. (0.081 mole) 50% sodium hydride in 500 ml. anhydrous tetrahydrofuran (THF) was added dropwise at room temperature a solution of 16.2 g. (0.089 mole) trimethylphosphonoacetate in 50 ml. THF and the mixture stirred for 15 minutes. A solution of 17.4 g. (0.074 mole) 2-(3,5-dimethoxyphenyl)cyclohexanone in 100 ml. THF was added in portions after which the mixture was heated at 70° C. for three hours and cooled to 0° C. Glacial acetic acid, 5.4 g., was added and the resulting mixture diluted with water and extracted with ethyl acetate. The extracts were dried (Na$_2$SO$_4$) and evaporated to give 22 g. of crude product which was crystallized from isopropyl ether; 20.4 g., M.P. 80°–81° C. $^1$H-NMR (CDCl$_3$) ppm (delta): 3.60 (s, 3H, COOC$\underline{H}_3$), 3.80 (s, 6H, OC$\underline{H}_3$), 5.20 (s, 1H, olefin), 6.34 (s, 3H, aromatic). Mass spectrum, exact mass for C$_{17}$H$_{24}$O$_4$: 292.3783. Found: 292.1658.

EXAMPLE 36

2-(3,5-Dimethoxyphenyl)-1-(Carboxymethylene)Cyclohexane

To a solution of 20 g. of the above methyl ester in 100 ml. methanol, 50 ml. water and 50 ml. tetrahydrofuran was added 42 ml. 5N sodium hydroxide and the mixture heated on the steam-bath for three hours. After dilution with ice-water, 220 ml. 1N hydrochloric acid was added, the mixture extracted with ethyl acetate, the extracts dried (Na$_2$SO$_4$) and evaporated in vacuo to give 20 g. of crude acid. Recrystallization from methylene chloride/ethyl ether yielded 16.7 g. of product, M.P. 154°–156° C. Mass spectrum, exact mass for C$_{16}$H$_{22}$O$_4$: 278.3515. Found: 278.1526.

$^1$H-NMR (CDCl$_3$) ppm (delta): 3.70 (s, 6H), 5.15 (s, 1H), 6.30 (s, 3H), 10.90 (s, 1H, COO$\underline{H}$).

EXAMPLE 37 dl-trans-2-[2-(3,5-Dimethoxyphenyl)cyclohexyl)]Acetic Acid

To a solution of 15 g. (0.054 mole) 2-(3,5-dimethoxyphenyl-1-carboxymethylene-1-(carboxymethylene)cyclohexane in 200 ml. tetrahydrofuran and one liter of liquid ammonia at −33° C. was added 832 mg. (0.119 mole) lithium metal. After a blue color formed and persisted for two minutes, the reaction was quenched by addition of 15 g. ammonium chloride. The ammonia was evaporated under a stream of nitrogen. Water (200 ml.) was added and the solution acidified to pH 3.5 with 6N hydrochloric acid. The aqueous layer was extracted with methylene chloride, the extracts dried (Na$_2$SO$_4$) and evaporated to give 15 g. of crude product. This was triturated with hexane and filtered to afford 14.8 g. of product, M.P. 110°–111.5° C. $^1$H-NMR (CDCl$_3$) ppm (delta) 270 MHz: 1.90 (d, 1H, J=14.6 Hz), 2.16 (dd, 2H, J=14.7, 2.3), 2.17 (td, 1H, J=11.3).

From the above NMR data the relative stereochemical structure below, was assigned.

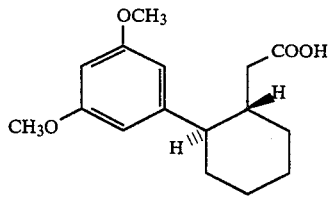

EXAMPLE 38 dl-4a,10b-trans-7,9-Dimethoxy-2,3,4,4a,5,10b-Hexahydro-1H-Phenanthren-6-one

To a solution of 14.7 g. (0.052 mole) trans-2-[2-(3,5-dimethoxyphenyl)cyclohexyl]acetic acid, obtained above, in 28 ml. trifluoroacetic acid at 0° C. was added 20 ml. trifluoroacetic anhydride and the mixture stirred at 0° C. for 15 minutes. The volatiles were evaporated, the residue taken up in methylene chloride, washed in turn with water, sodium bicarbonate solution, brine and dried over anhydrous sodium sulfate. Evaporation of solvent gave 15.7 g. of crude product which was recrystallized from ethyl ether to afford 12.5 g. of title compound, M.P. 110°–111° C. Mass spectrum, exact mass calculated for C$_{16}$H$_{20}$O$_3$: 260.3358. Found: 260.1404.

EXAMPLE 39 dl-4a,10b-trans-7,9-Dihydroxy-2,3,4,4a,5,10b-hexahydro-1H-phenanthren-6-one

A solution of 12.3 g. (0.047 mole) dl-4a,10b-trans-7,9-dimethoxy-2,3,4,4a,5,10b-hexahydro-1H-phenanthrene-6-one in 220 ml. glacial acetic acid and 220 ml. 48% hydrobromic acid was heated under a nitrogen atmosphere for 36 hours at 100° C. The volatiles were evaporated under reduced pressure and the residue purified by chromatography on silica gel, eluting with ethyl acetate to give 12 g. of product, M.P. 189°–200° C. Recrystallization from ethyl acetate/chloroform gave 10 g. of pure product, M.P. 200°–201° C. $^1$H-NMR (CD$_3$COCD$_3$) ppm (delta): 6.50–6.10 (m, 2H, aromatic), 13.0 (s, 1H, O$\underline{H}$). Mass spectrum, exact mass calculated for C$_{14}$H$_{16}$O$_3$: 232.2816. Found: 232.1097.

EXAMPLE 40

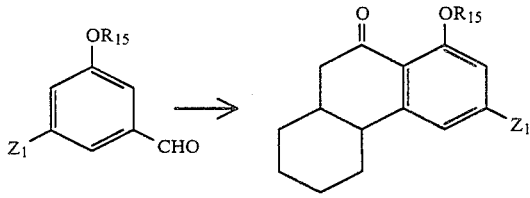

Employing one of the above 3-$OR_{15}$-5-$Z_1$-substituted benzaldehydes in place of 3,5-dimethoxybenzaldehyde in the procedure of Example 31 and carrying the product in turn, through the procedures of Examples 32–39 provides products of the above formula where $R_{15}$ is hydrogen, methyl, ethyl, isopropyl or n-butyl and $Z_1$ is as shown below.

| $Z_1$ |
| --- |
| $OCH_3$ |
| $OC_2H_5$ |
| $O(CH_2)_3CH_3$ |
| $O(CH_2)_5CH_3$ |
| $O(CH_2)_6CH_3$ |
| $O(CH_2)_8CH_3$ |
| $O(CH_2)_{11}CH_3$ |
| $O(CH_2)_{12}CH_3$ |
| $OCH(CH_3)(CH_2)_2CH_3$ |
| $OCH(CH_3)(CH_2)_4CH_3$ |
| $OCH_2C_6H_5$ |
| $CH(CH_3)(CH_2)_2CH_3$ |
| $CH_2(CH_2)_3CH_3$ |
| $C(CH_3)_2(CH_2)_3CH_3$ |
| $C(CH_3)_2(CH_2)_4CH_3$ |
| $C(CH_3)_2(CH_2)_8CH_3$ |
| $CH(CH_3)(CH_2)_8CH_3$ |
| $CH(CH_3)(CH_2)_9CH_3$ |
| $C(CH_3)_2(CH_2)_9CH_3$ |
| $CH_2(CH_2)_{11}CH_3$ |
| $CH(CH_3)(CH_2)_5CH(CH_3)CH_3$ |
| $CH(C_2H_5)(CH_2)_5CH(CH_3)CH_3$ |
| $CH(C_2H_5)(CH_2)_6CH(C_2H_5)CH_3$ |
| $(CH_2)_3OCH_2CH_3$ |
| $(CH_2)_3O(CH_2)_2CH_3$ |
| $(CH_2)_2O(CH_2)_3CH_3$ |
| $CH_2O(CH_2)_5CH_3$ |
| $(CH_2)_3OCH(CH_3)(CH_2)_2CH_3$ |
| $CH(CH_3)(CH_2)_2OCH_2CH_3$ |
| $CH(CH_3)(CH_2)_2O(CH_2)_4CH_3$ |
| $CH(CH_3)(CH_2)_2OCH_2CH(C_2H_5)CH_3$ |
| $(CH_2)_4O(CH_2)_3CH_3$ |
| $(CH_2)_3O(CH_2)_9CH_3$ |
| $CH(CH_3)(CH_2)_2O(CH_2)_8CH_3$ |
| 2-pyridyl-$(CH_2)_3$ |
| 4-pyridyl-$(CH_2)_3$ |
| 4-pyridyl-$(CH_2)_4$ |
| 3-pyridyl-$(CH_2)_4$ |
| 4-pyridyl-$(CH_2)_5$ |
| 2-pyridyl-$(CH_2)_6$ |
| 3-pyridyl-$(CH_2)_8$ |
| 4-pyridyl-$CH(CH_3)(CH_2)_2$ |
| 4-pyridyl-$CH(CH_3)CH(C_2H_5)CH_2$ |
| 4-pyridyl-$CH(CH_3)(CH_2)_3CH(CH_3)$ |
| 4-pyridyl-$CH(CH_3)O(CH_2)_3$ |
| 2-pyridyl-$CH_2O(CH_2)_2$ |
| 2-pyridyl-$CH_2CH_2OCH_2$ |
| 3-pyridyl-$CH(CH_3)O(CH_2)_4$ |
| 3-pyridyl-$CH(CH_3)(CH_2)_2O(CH_2)_4$ |
| 4-pyridyl-$CH(CH_3)O(CH_2)_3$ |
| 2-pyridyl-$(CH_2)_4O(CH_2)_4$ |
| 3-pyridyl-$(CH_2)_2O(CH_2)_2$ |
| 2-pyridyl-$(CH_2)_3CH(CH_3)O$ |
| 4-pyridyl-$(CH_2)_3O$ |
| 4-pyridyl-$CH_2CH(CH_3)O$ |
| 3-pyridyl-$(CH_2)_4O$ |
| 3-pyridyl-$(CH_2)_6O$ |
| 2-pyridyl-$(CH_2)_8O$ |

| $Z_1$ |
| --- |
| 4-pyridyl-$(CH_2)_4CH(CH_3)O$ |
| 4-pyridyl-$CH(CH_3)(CH_2)_2CH(CH_3)O$ |
| 2-pyridyl-$(CH_2)_4CH(CH_3)(CH_2)_2O$ |
| $C_6H_5(CH_2)_3$ |
| $C_6H_5CH_2CH(CH_3)$ |
| $C_6H_5CH(CH_3)CH_2$ |
| 4-$ClC_6H_4(CH_2)_4$ |
| 4-$ClC_6H_4(CH_2)_2CH(CH_3)$ |
| 4-$FC_6H_4(CH_2)_3CH(CH_3)$ |
| 4-$FC_6H_4(CH_2)_7$ |
| 4-$FC_6H_4(CH_2)_5CH(CH_3)$ |
| 2-$ClC_6H_4(CH_2)_3CH(C_2H_5)$ |
| $C_6H_5(CH_2)_3CH(CH_3)(CH_2)_2$ |
| $C_6H_5(CH_2)_2CH(CH_3)$ |
| $C_6H_5O(CH_2)_3$ |
| $C_6H_5OCH_2CH(CH_3)$ |
| $C_6H_5O(CH_2)_3CH(CH_3)$ |
| $C_6H_5O(CH_2)_8$ |
| 4-$ClC_6H_4O(CH_2)_4$ |
| 4-$ClC_6H_4OCH(CH_3)CH_2$ |
| 4-$FC_6H_4OCH_2CH(CH_3)$ |
| 4-$FC_6H_4OCH(CH_3)(CH_2)_4CH(CH_3)$ |
| 4-$FC_6H_4O(CH_2)_3CH(CH_3)$ |
| $C_6H_5(CH_2)_3O$ |
| $C_6H_5CH_2CH(CH_3)O$ |
| 4-$ClC_6H_4(CH_2)_3CH(CH_3)O$ |
| 4-$FC_6H_4(CH_2)_3CH(CH_3)O$ |
| $C_6H_5(CH_2)_4CH(CH_3)O$ |
| $C_6H_5(CH_2)_6CH(CH_3)O$ |
| $C_6H_5(CH_2)_6O$ |
| $C_6H_5(CH_2)_7O$ |
| 4-$ClC_6H_4(CH_2)_8O$ |
| 4-$FC_6H_4(CH_2)_6CH(CH_3)O$ |
| 4-$FC_6H_4CH(CH_3)(CH_2)_3CH(CH_3)O$ |
| 2-$ClC_6H_4(CH_2)_3O$ |
| $C_6H_5(CH_2)_2O(CH_2)_2$ |
| $C_6H_5CH_2O(CH_2)_2$ |
| $C_6H_5(CH_2)_2OCH_2$ |
| $C_6H_5(CH_2)_4O(CH_2)_4$ |
| $C_6H_5(CH_2)_3O(CH_2)_3$ |
| $C_6H_5(CH_2)_3OCH(CH_3)$ |
| $C_6H_5(CH_2)_6O(CH_2)_2$ |
| 4-$ClC_6H_4(CH_2)_6OCH(CH_3)$ |
| 4-$FC_6H_4(CH_2)_2O(CH_2)_2$ |
| 4-$FC_6H_4(CH_2)_3O(CH_2)_2CH(CH_3)$ |
| 4-$FC_6H_4(CH_2)_2O(CH_2)_3CH(CH_3)$ |

EXAMPLE 41 dl-4a,10b-trans-7-Hydroxy-9-(5-phenyl-2-pentyloxy)-2,3,4,4a,5,10b-hexahydro-1H-phenanthren-6-one A mixture of 9.9 g. (0.043 mole) dl-trans-7,9-dihydroxy-2,3,4,4a,5,10b-hexahydro-1H-phenanthren-6-one, 7.1 g. (0.103 mole) potassium carbonate and 120 ml. dimethylformamide (DMF) was heated at 70° C. for thirty minutes. A solution of 13.55 g. (0.056 mole) 2-methylsulfonyloxy-5-phenylpentane in 10 ml. DMF was added in one portion and the mixture heated under nitrogen at 80° C. overnight. The reaction mixture was diluted with ice-water, extracted with ethyl acetate, the extracts dried ($Na_2SO_4$) and evaporated in vacuo to give 21 g. of crude product. Column chromatography on 750 g. silica gel, eluting first with chloroform/hexane, then chloroform alone and finally with chloroform/ethyl ether, gave 14 g. of product as an oil. $^1$H-NMR ($CDCl_3$) ppm (delta): 1.40 (d, 3H), 4.45 (m, 1H), 6.20–6.50 (m, 2H), 7.30 (s, 5H), 13.10 (s, 1H).

EXAMPLE 42 dl-4a,10b-trans-7-Benzyloxy-9-(5-phenyl-2-pentyloxy)-2,3,4,4a,5,10b-hexahydro-1H-phenanthren-6-one To a suspension of 720 mg. (0.015 mole) of a 50% oil dispersion of sodium hydride in 25 ml. dimethylformamide (DMF) at 0° C. was added dropwise a solution of 5.0 g. (0.013 mole) dl-trans-7-hydroxy-9-(5-phenyl-2-pentyloxy)-2,3,4,4a,5,10b-hexahydro-1H-phenanthrene-6-one in 15 ml. DMF and the mixture allowed to warm to room temperature. To this was added in one portion 2.56 g. (0.015 mole) benzyl bromide and the mixture stirred under nitrogen for 18 hours at room temperature. Water was added to dilute the mixture, which was then extracted with ethyl acetate. The extracts were dried (Na$_2$SO$_4$) and solvent evaporated to give 7 g. of crude product which was purified by chromatography on silica gel, eluting with ethyl ether/hexane. Evaporation of the product-containing fractions gave 5.8 g. $^1$H-NMR (CDCl$_3$) ppm (delta): 1.10 (d, 3H), 5.10 (s, 2H), 6.23–6.54 (m, 2H), 6.95–7.70 (m, 10H).

EXAMPLE 43 dl-4a,10b-trans-7-Benzyloxy-6-hydroxy-6-ethoxycarbonylmethyl-9-(5-phenyl-2-pentyloxy)-2,3,4,4a,5,10b-hexahydro-1H-phenanthrene To a solution of 4.07 g. (0.0403 mole) diisopropylamine in 100 ml. tetrahydrofuran (THF) at 0° C. was added dropwise a solution of 16.8 ml. (0.0403 mole) 2.4M n-butyllithium in hexane and the mixture stirred under a nitrogen atmosphere for one hour, then cooled to −78° C. A mixture of 3.55 g. (0.0403 mole) ethyl acetate in 10 ml. THF was added dropwise, stirring continued for 30 minutes at −78° C., then 5.8 g. (0.0124 mole) dl-trans-7-benzyloxy-9-(5-phenyl-2-pentyloxy)-2,3,4,4a,5,10b-hexahydro-1H-phenanthrene-6-one dissolved in 20 ml. THF was added dropwise and the resulting mixture stirred for 10 minutes. Glacial acetic acid (2.5 g.) was added to quench the reaction, the mixture diluted with water and extracted with ethyl acetate. The extracts were dried (Na$_2$SO$_4$) and the solvent evaporated in vacuo to give 6.9 g. of product which was used without further purification. $^1$H-NMR (CDCl$_3$) ppm (delta): 4.105 (q, 2H), 4.605 (s, 1H, O$\underline{H}$), 5.055 (s, 2H, C$\underline{H}_2$C$_6$H$_5$).

EXAMPLE 44 dl-4a,10b-trans-7-Acetoxy-6-Ethoxycarbonylmethylene-9-(5-phenyl-2-pentyloxy)-2,3,4,4a,5,10b-hexahydro-1H-phenanthrene A mixture of 6.9 g. dl-trans-7-benzyloxy-6-hydroxy-6-ethoxycarbonylmethyl-9-(5-phenyl-2-pentyloxy)-2,3,4,4a,5,10b-hexahydro-1H-phenanthrene, 250 ml. ethanol and 3 g. 5% Pd/C catalyst was hydrogenated at 40 psi (2.8 kg./cm.$^2$). Removal of catalyst by filtration and evaporation of the filtrate gave 5.7 g. of residue. This was taken up in 100 ml. methylene chloride, 4.5 g. acetic anhydride and 8.0 g. triethylamine added and the mixture allowed to stand overnight. The volatiles were evaporated in vacuo, the residue dissolved in ethyl acetate, washed with water, dried (Na$_2$SO$_4$) and the solvent evaporated to give 5.6 g. of product which was used without purification.

EXAMPLE 45 dl-4a,10b-trans-7-Hydroxy-6-Carboxymethylene-9-(5-phenyl-2-pentyloxy)-2,3,4,4a,5,10b-hexahydro-1H-phenanthrene lactone,

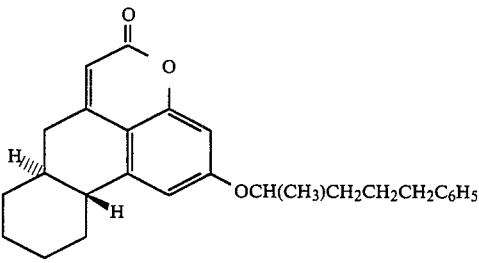

A. To a solution of 5.6 g. (0.011 mole) dl-trans-7-acetoxy-6-ethoxycarbonylmethylene-9-(5-phenyl-2-pentyloxy)-2,3,4,4a,5,10b-hexahydro-1H-phenanthrene in 75 ml. tetrahydrofuran and 25 ml. methanol was added 56 ml. 1N sodium hydroxide and the mixture stirred at room temperature for one hour. Then 56 ml. 1N hydrochloric acid was added, the mixture extracted with ethyl acetate and the extracts dried over anhydrous sodium sulfate. Evaporation of solvent gave 5 g. of crude product which was purified by chromatography on 400 g. silica gel eluting with ethyl ether/hexane. Fractions containing like product were combined and evaporated to dryness to obtain 1.44 g. of a less polar product and 2.2 g. of the more polar title compound. Infrared spectrum (CHCl$_3$): 1710 cm$^{-1}$. Mass spectrum, exact mass, calculated for C$_{27}$H$_{30}$O$_3$: 402.538. Found: 402.218.

B. The less polar product was identified as the corresponding saturated lactone. Infrared spectrum (CHCl$_3$): 1725 cm$^{-1}$. Mass spectrum, exact mass, calculated for C$_{27}$H$_{32}$O$_3$: 404.554. Found: 404.239.

Alternatively, the saturated lactone is prepared from the 6,8-dimethoxy-9-one compound provided in Example 38 by sequential operation of the procedures of Examples 25 through 29.

EXAMPLE 46 dl-4a,10b-trans-7-Hydroxy-6-beta-(2-Hydroxyethyl)-9-(5-phenyl-2-pentyloxy)-1,2,3,4,4a,5,6,10b-octahydrophenanthrene A solution of dl-4a,10b-trans-7-hydroxy-6-carboxymethylene-9-(5-phenyl-2-pentyloxy)-2,3,4,4a,5,10b-hexahydro-1H-phenanthrene lactone (2.1 g., 5.2 mmole) in 100 ml. ethyl ether was added to 400 ml. liquid ammonia. Lithium metal (84 mg., 12 mmole) was added in portions and the blue color allowed to persist for two minutes. The reaction was quenched with 2.1 g. ammonium chloride, the ammonia evaporated under a stream of nitrogen, the residue taken up in water, acidified to pH 3 with 1N hydrochloric acid and extracted with ethyl acetate. The extracts were dried (Na$_2$SO$_4$) and evaporated in vacuo to give 2.1 g. of crude product which was purified by chromatography on silica gel, eluting with isopropyl ether/hexane mixtures to afford 440 mg. of title compound. $^1$H-NMR (CDCl$_3$) ppm (delta): 1.15 (d, 3H, C$\underline{H}_3$), 3.80 (t, 2H, C$\underline{H}_2$OH), 4.25 (m, 1H, OC$\underline{H}$), 6.25–6.50 (m, 2H, aromatic), 7.20 (s, 5H, phenyl).

EXAMPLE 47

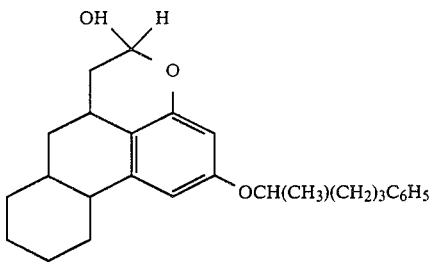

A solution of 630 mg. (1.60 mmole) of the saturated lactone obtained in Example 45, Part B, in 20 ml. toluene was cooled to −78° C. and 1.6 ml. of 1N diisobutylaluminum hydride (DIBAL-H) in hexane was added. The resulting mixture was stirred at −78° C. for 15 minutes, methanol added to quench the reaction, the mixture poured into ethyl ether and washed with 50% aqueous sodium potassium tartrate. The ether layer was dried (MgSO$_4$) and the solvent evaporated to give 640 mg. of crude lactol which was used without further purification.

EXAMPLE 48

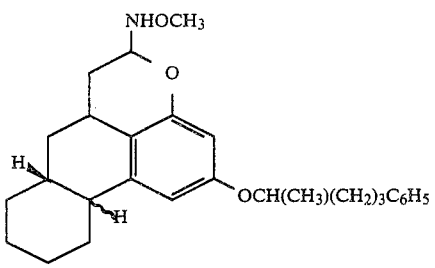

To a solution of 640 mg. (1.6 mmole) of the lactol provided in the preceding Example in 5 ml. each of pyridine and ethanol was added 135 mg. (1.6 mmole) O-methylhydroxylamine hydrochloride and the mixture stirred at room temperature for ten minutes. The volatiles were evaporated in vacuo, the residue taken up in ethyl ether, washed with water and the extracts dried (MgSO$_4$). Evaporation of ether afforded 650 mg. of crude product which was purified by chromatography on 60 g. of silica gel, eluting with ethyl ether. The product-containing fractions were combined and evaporated to dryness to give 590 mg. of the desired methoxyamine.

EXAMPLE 49 dl-trans-4a,10b-6-(2-Aminoethyl)-7-Hydroxy-9-(5-Phenyl-2-pentyloxy)-1,2,3,4,4a,5,6,10b-octahydrophenanthrene and N-Formyl Derivative A. To a stirred suspension of 605 mg. (16 mmole) sodium borohydride in 50 ml. tetrahydrofuran was added dropwise 1.82 g. (16 mmole) trifluoroacetic acid and the mixture stirred at room temperature for five minutes. To this was added 590 mg. (16 mmole) of the methoxyamine obtained in the preceding Example. The mixture was heated at reflux for three hours. The reaction was quenched by addition of ice and extracted with methylene chloride. After drying the extracts over anhydrous magnesium sulfate and evaporation of solvent, 600 mg. of the title amino compound was obtained. B. The amino compound obtained above, 600 mg., was mixed with 560 mg. of formic acetic anhydride in 20 ml. ethyl ether and the mixture stirred at room temperature for one hour. The solvent was evaporated and the residue purified by column chromatography on 60 g. silica gel eluting with ethyl ether and ethyl acetate to give 260 mg. crude product. This was dissolved in methanol, 1 ml. 1N sodium hydroxide added and the mixture stirred for one hour at 0° C.; 1 ml. 1N hydrochloric acid added and the mixture evaporated to dryness and partitioned between ethyl ether and water. Evaporation of the ether gave 260 mg. of the N-formyl compound. $^1$H-NMR (CDCl$_3$) ppm (delta): 6.40 (m, 3H, aromatics and N$\underline{\text{H}}$), 7.10 (s, 5H, phenyl), 8.00 (broad singlet, 2H, CO$\underline{\text{H}}$ and phenol); mass spectrum (m/e): 435 (M$^+$), 363 (M—(CH$_2$)$_2$NHCHO), 217 (base peak).

EXAMPLE 50

Employing the products of Example 40 wherein R$_{15}$ is hydrogen as starting material in the procedure of Example 42 and carrying the benzyloxy derivative thus obtained through the procedures of Examples 43, 44 and 45, provides a mixture of saturated and unsaturated lactones of the formula below wherein the broken line is an optional double bond and Z$_1$ is as defined in Example 40. The mixture is separated by column chromatography on silica gel as described in Example 45.

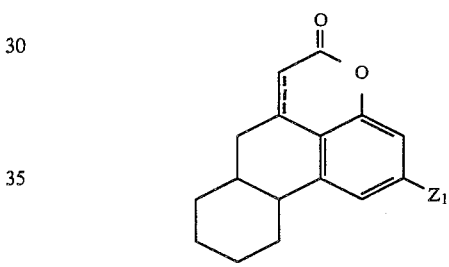

EXAMPLE 51

2-(3,5-Dimethoxyphenyl)cyclopentanone

The method is a modification of that employed by Arnold et al., *J. Amer. Chem. Soc.*, 72, 3154 (1950), for preparation of 2-phenylcyclopentanone.

To an ice-cold stirred solution of 3,5-dimethoxyphenylmagnesium bromide, prepared from 25.5 g. of magnesium and 226 g. (1.04 mole) of 3,5-dimethoxybromobenzene in 800 ml. dry ethyl ether, is added a solution of 118.5 g. 2-chlorocyclopentanone in 400 ml. dry ethyl ether. The ether is removed by distillation and is replaced by 200 ml. dry xylene. The resulting mixture is heated at 150°-170° C. for two hours, cooled, poured onto ice and diluted with 6N hydrochloric acid. The acidified mixture is extracted with benzene. The organic phase was washed with water and dilute sodium hydroxide solution, then dried over anhydrous sodium sulfate. The solvents were evaporated in vacuo and the product purified by distillation in vacuo.

EXAMPLE 52

Repeating the procedure of Example 35, but starting with 2-(3,5-dimethoxyphenyl)cyclopentanone in place of the cyclohexanone derivative used therein provides 2-(3,5-dimethoxyphenyl)-1-methoxycarbonylmethylene)-cyclopentane. When this is carried in turn through the procedures of Examples 36-39, dl-3a,9b- trans-6,8-dihydroxy-2,3,3a,4,5,9b-hexahydro-1H-benz[e]inden-5-one is obtained.

EXAMPLE 53

Starting with dl-3a,9b-trans-6,8-dihydroxy-2,3,3a,-4,5,9b-hexahydro-1H-benz[e]inden-5-one provided in Example 52 in the procedure of Example 41 and carrying the product thereof in turn through the procedures of Examples 42–45 and separation of the saturated and unsaturated lactones as described in the latter Example, provides the corresponding benz[e]indenes of the formula

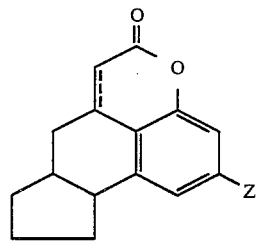

where the broken line is an optional double bond and Z is $OCH(CH_3)(CH_2)_3C_6H_5$.

When the above is repeated, but the procedure of Example 41 is carried out with the appropriate Z—SO$_2$CH$_3$ in place of the 2-methylsulfonyloxy-5-phenylpentane used therein, compounds of the above formula are provided wherein Z is as defined below.

| Z | Z |
|---|---|
| O(CH$_2$)$_2$CH(CH$_3$)$_2$ | 2-pyridyl-(CH$_2$)$_3$CH(CH$_3$)O |
| O(CH$_2$)$_8$CH(CH$_3$)$_2$ | 3-pyridyl-(CH$_2$)$_5$CH(C$_2$H$_5$)O |
| O(CH$_2$)$_{12}$CH$_3$ | 4-pyridyl-(CH$_2$)$_6$O | or one of the values given in Example 40 for $Z_1$ where $Z_1$ is alkoxy, pyridylalkoxy or phenylalkoxy.

EXAMPLE 54

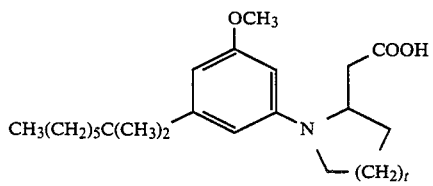

A. dl-2-[1-[3-Methoxy-5-(1,1-dimethylheptyl)-phenyl]-pyrrolidin-2-yl]acetic acid A mixture of 24.9 g. (0.10 mole) 3-methoxy-5-(1,1-dimethylheptyl)aniline, 34.5 g. (0.12 mole) methyl dl-3,6-dibromocaproate, 15 g. triethylamine and 100 ml. ethyl ether is stirred under nitrogen at room temperature for 20 hours. The ether is evaporated and the residue heated at 90°–120° C. for three hours. Additional methyl dl-3,6-dibromocaproate (5 g.) and triethylamine (5 g.) is added and heating continued at 90° C. for 2 hours and finally at 120° C. for one hour. The reaction mixture is worked up as described in Example 16 to provide the methyl ester of the desired product which is hydrolyzed in methanolic sodium hydroxide by the method of Example 17 to provide the title acid.

B. dl-2-[1-[3-Methoxy-5-(1,1-dimethylheptyl)phenyl]-piperidin-2-yl]acetic acid (t=2)

Employing methyl dl-3,7-dibromoheptanoate in the above procedure in place of methyl dl-3,6-dibromocaproate and hydrolysis of the methyl ester by the method of Example 23 affords the title compound.

C. In like manner the following compounds are obtained from the appropriate 3-methoxy-5-$Z_1$-substituted anilines by the above procedures. The latter starting anilines are provided in U.S. Pat. No. 4,260,764.

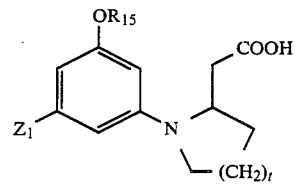

In the above formula t is 1 or 2, $R_{15}$ is (C$_1$–C$_4$) alkyl or benzyl and $Z_1$ is as defined below.

| $Z_1$ |
|---|
| OCH$_2$C$_6$H$_5$ |
| OCH(CH$_3$)$_2$ |
| O(CH$_2$)$_4$CH$_3$ |
| O(CH$_2$)$_4$CH(CH$_3$)$_2$ |
| OCH(CH$_3$)(CH$_2$)$_3$CH$_3$ |
| OCH(CH$_3$)(CH$_2$)$_4$CH$_3$ |
| O(CH$_2$)$_8$CH$_3$ |
| O(CH$_2$)$_{12}$CH$_3$ |
| OCH(CH$_3$)(CH$_2$)$_5$CH$_3$ |
| OC(CH$_3$)$_2$(CH$_2$)$_5$CH$_3$ |
| OCH(CH$_3$)(CH$_2$)$_8$CH(CH$_3$)$_2$ |
| (CH$_2$)$_4$CH$_3$ |
| CH(CH$_3$)(CH$_2$)$_3$CH$_3$ |
| C(CH$_3$)$_2$(CH$_2$)$_3$CH$_3$ |
| C(CH$_3$)$_2$(CH$_2$)$_4$CH$_3$ |
| C(C$_2$H$_5$)$_2$(CH$_2$)$_3$CH$_3$ |
| C(C$_2$H$_5$)$_2$(CH$_2$)$_5$CH$_3$ |
| CH$_3$C(C$_2$H$_5$)(CH$_2$)$_5$CH$_3$ |
| CH(CH$_3$)(CH$_2$)$_2$CH$_3$ |
| CH(C$_2$H$_5$)(CH$_2$)$_6$CH$_3$ |
| CH(CH$_3$)(CH$_2$)$_7$CH$_3$ |
| CH(CH$_3$)(CH$_2$)$_8$CH$_3$ |
| CH(CH$_3$)(CH$_2$)$_{10}$CH$_3$ |
| CH(C$_2$H$_5$)(CH$_2$)$_9$CH$_3$ |
| CH(CH$_3$)(CH$_2$)$_9$CH$_3$ |
| C(CH$_3$)$_2$(CH$_2$)$_9$CH$_3$ |
| C(CH$_3$)$_2$(CH$_2$)$_7$CH$_3$ |
| (CH$_2$)$_{12}$CH$_3$ |
| (CH$_2$)$_{11}$CH$_3$ |
| (CH$_2$)$_8$CH$_3$ |
| (CH$_2$)$_5$CH$_3$ |
| CH(CH$_3$)(CH$_2$)$_2$CH$_3$ |
| (CH$_2$)$_3$OCH$_2$CH$_3$ |
| CH$_2$O(CH$_2$)$_4$CH$_3$ |
| CH$_2$O(CH$_2$)$_5$CH$_3$ |
| (CH$_2$)$_2$O(CH$_2$)$_2$CH$_3$ |
| (CH$_2$)$_2$O(CH$_2$)$_4$CH$_3$ |
| (CH$_2$)$_2$O(CH$_2$)$_{10}$CH$_3$ |
| (CH$_2$)$_3$OCH$_2$CH$_3$ |
| (CH$_2$)$_3$O(CH$_2$)$_2$CH$_3$ |
| (CH$_2$)$_3$O(CH$_2$)$_2$CH(CH$_3$)$_2$ |
| CH(CH$_3$)CH$_2$O(CH$_2$)$_5$CH$_3$ |
| CH(CH$_3$)CH$_2$O(CH$_2$)$_7$CH$_3$ |
| CH(CH$_3$)CH$_2$O(CH$_2$)$_9$CH$_3$ |
| (CH$_2$)$_4$OCH$_3$ |
| (CH$_2$)$_4$O(CH$_2$)$_3$CH$_3$ |
| CH(CH$_3$)(CH$_2$)$_2$OCH$_3$ |
| CH(CH$_3$)(CH$_2$)$_2$O(CH$_2$)$_3$CH$_3$ |
| CH(CH$_3$)(CH$_2$)$_2$O(CH$_2$)$_2$CH(CH$_3$)$_2$ |
| CH(CH$_3$)(CH$_2$)$_2$OCH(CH$_3$)$_2$ |
| (CH$_2$)$_7$OCH$_3$ |
| (CH$_2$)$_7$OCH(CH$_3$)$_2$ |
| (CH$_2$)$_7$O(CH$_2$)$_5$CH$_3$ |
| (CH$_2$)$_7$O(CH$_2$)$_3$CH(CH$_3$)$_2$ |
| (CH$_2$)$_6$O(CH$_2$)$_3$CH(CH$_3$)$_2$ |
| (CH$_2$)$_{10}$OCH$_3$ |
| (CH$_2$)$_{10}$OCH(CH$_3$)$_2$ |
| CH(CH$_3$)(CH$_2$)$_8$OCH(CH$_3$)$_2$ |

| $Z_1$ |
|---|
| $C(CH_3)_2CH_2OCH_3$ |
| $C(CH_3)_2CH_2OCH_2CH(CH_3)_2$ |
| $(CH_2)_{12}OCH_3$ |
| $CH_2O(CH_2)_{11}CH_3$ |
| 2-pyridyl-$(CH_2)_3$ |
| 3-pyridyl-$(CH_2)_3$ |
| 4-pyridyl-$(CH_2)_4$ |
| 4-pyridyl-$(CH_2)_6$ |
| 4-pyridyl-$(CH_2)_7$ |
| 2-pyridyl-$(CH_2)_8$ |
| 2-pyridyl-$CH(CH_3)CH_2$ |
| 3-pyridyl-$CH(CH_3)(CH_2)_4$ |
| 4-pyridyl-$CH(CH_3)(CH_2)_3CH(CH_3)$ |
| 2-pyridyl-$CH(CH_3)(CH_2)_4CH(CH_3)$ |
| 2-pyridyl-$(CH_2)_3O$ |
| 3-pyridyl-$(CH_2)_4O$ |
| 4-pyridyl-$(CH_2)_5O$ |
| 2-pyridyl-$(CH_2)_6O$ |
| 3-pyridyl-$(CH_2)_7O$ |
| 4-pyridyl-$(CH_2)_8O$ |
| 4-pyridyl-$(CH_2)_6CH(CH_3)O$ |
| 2-pyridyl-$(CH_2)_5CH(C_2H_5)O$ |
| 2-pyridyl-$CH(CH_3)(CH_2)_2CH(CH_3)O$ |
| 4-pyridyl-$CH(CH_3)CH_2CH(CH_3)O$ |
| 4-pyridyl-$CH(CH_3)(CH_2)_2O$ |
| 4-pyridyl-$(CH_2)_2CH(CH_3)O$ |
| 2-pyridyl-$(CH_2)_2OCH_2$ |
| 2-pyridyl-$CH_2O(CH_2)_2$ |
| 3-pyridyl-$CH_2O(CH_2)_3$ |
| 2-pyridyl-$CH_2O(CH_2)_5$ |
| 2-pyridyl-$CH_2O(CH_2)_7$ |
| 2-pyridyl-$(CH_2)_2O(CH_2)_2$ |
| 4-pyridyl-$(CH_2)_2O(CH_2)_3$ |
| 4-pyridyl-$(CH_2)_2OCH(CH_3)$ |
| 2-pyridyl-$(CH_2)_3OCH(CH_3)$ |
| 2-pyridyl-$(CH_2)_3OCH_2CH(CH_3)$ |
| 3-pyridyl-$(CH_2)_4O(CH_2)_4$ |
| 4-pyridyl-$(CH_2)_3CH(CH_3)$—O—$CH_2$ |
| 2-pyridyl-$CH(CH_3)OCH_2$ |
| 2-pyridyl-$CH(CH_3)CH_2OCH(CH_3)$ |
| 4-pyridyl-$CH(C_2H_5)CH_2OCH(CH_3)$ |
| 4-pyridyl-$CH(CH_3)CH_2O(CH_2)_5$ |
| 4-pyridyl-$CH(CH_3)CH_2O(CH_2)_2CH(CH_3)$ |
| $C_6H_5(CH_2)_3$ |
| $C_6H_5CH(CH_3)CH_2$ |
| $C_6H_5C(CH_3)_2$ |
| $C_6H_5(CH_2)_4$ |
| $C_6H_5CH(CH_3)(CH_2)_4$ |
| $C_6H_5CH(CH_3)(CH_2)_4CH(CH_3)$ |
| $C_6H_5CH(CH_3)CH_2CH(CH_3)CH_2CH(CH)_3$ |
| $C_6H_5(CH_2)_4$ |
| $C_6H_5(CH_2)_4CHCH_3$ |
| $C_6H_5(CH_2)_5$ |
| $C_6H_5(CH_2)_6$ |
| $C_6H_5(CH_2)_6CHCH_3$ |
| $C_6H_5CH_2C(CH_3)_2$ |
| $C_6H_5CH_2C(C_2H_5)_2$ |
| $C_6H_5(CH_2)_3C(C_2H_5)$ |
| 4-$FC_6H_4(CH_2)_3$ |
| 2-$ClC_6H_4CH(CH_3)CH_2$ |
| 3-$ClC_6H_4(CH_2)_5$ |
| 4-$ClC_6H_4(CH_2)_3CH(CH_3)$ |
| 2-$FC_6H_4(CH_2)_3CH(CH_3)$ |
| 4-$FC_6H_4(CH_2)_3CH(CH_3)$ |
| 4-$FC_6H_4(CH_2)_5C(CH_3)_2$ |
| 4-$ClC_6H_4(CH_2)_8$ |
| 4-$ClC_6H_4(CH_2)_7$ |
| 3-$FC_6H_4(CH_2)_6$ |
| 3-$FC_6H_4(CH_2)_6CH(CH_3)$ |
| 4-$FC_6H_4(CH_2)_5CH(CH_3)$ |
| 2-$FC_6H_4(CH_2)_4CH(CH_3)$ |
| 2-$FC_6H_4(CH_2)_4CH(C_2H_5)$ |
| $C_6H_5O(CH_2)_3$ |
| $C_6H_5OCH_2CH(CH_3)$ |
| $C_6H_5OCH(C_2H_5)$ |
| $C_6H_5O(CH_2)_2CH((CH_3)$ |
| $C_6H_5O(CH_2)_3CH(CH_3)$ |
| $C_6H_5O(CH_2)_3CH(C_2H_5)$ |
| 4-$FC_6H(CH_2)_4CH(CH_3)$ |
| 2-$ClC_6H_4(CH_2)_4CH(CH_3)$ |
| 2-$FC_6H_4(CH_2)_5CH(CH_3)$ |
| 4-$ClC_6H_4(CH_2)_5CH(C_2H_5)$ |
| 3-$FC_6H_4(CH_2)_6CH(CH_3)$ |
| 4-$FC_6H_4CH(CH_3)(CH_2)_4CH(CH_3)$ |
| 4-$FC_6H_4(CH_2)_3CH(CH_3)CH(CH_3)$ |
| 4-$ClC_6H_4(CH_2)_2CH(CH_3)(CH_2)_2CH(CH_3)$ |
| $C_6H_5(CH_2)_3O$ |
| $C_6H_5CH_2CH(CH_3)O$ |
| $C_6H_5(CH_2)_4O$ |
| $C_6H_5(CH_2)_6O$ |
| $C_6H_5(CH_2)_8O$ |
| 4-$FC_6H_4(CH_2)_6O$ |
| 2-$FC_6H_4(CH_2)_3CH(CH_3)O$ |
| $C_6H_5(CH_2)_5CH(CH_3)O$ |
| 3-$ClC_6H_4(CH_2)_3O$ |
| 4-$ClC_6H_4(CH_2)_3CH(CH_3)O$ |
| 2-$ClC_6H_4CH_2CH(CH_3)(CH_2)_2CH(CH_3)O$ |
| 4-$FC_6H_4CH(CH_3)CH_2CH(CH_3)O$ |
| 4-$FC_6H_4(CH_2)_3CH(CH_3)O$ |
| $C_6H_5(CH_2)_4CH(CH_3)O$ |
| $C_6H_5(CH_2)_6CH(CH_3)O$ |
| $C_6H_5(CH_2)_2OCH_2$ |
| $C_6H_5CH_2O(CH_2)_2$ |
| 4-$ClC_6H_4CH_2O(CH_2)_3$ |
| 4-$FC_6H_4CH_2O(CH_2)_6$ |
| 2-$FC_6H_4(CH_2)_2O(CH_2)_6$ |
| 3-$ClC_6H_4(CH_2)_3O(CH_2)_3$ |
| $C_6H_5(CH_2)_3O(CH_2)_3CH(CH_3)$ |
| 4-$FC_6H_4(CH_2)_3O(CH_2)_3CH(CH_3)$ |
| $C_6H_5(CH_2)_7OCH_2$ |
| $C_6H_5(CH_2)_3CH(CH_3)OCH_2$ |
| $C_6H_5(CH_2)_3CH(CH_3)O(CH_2)_2$ |
| $C_6H_5(CH_2)_3O(CH_2)_3CH(CH_3)$ |

EXAMPLE 55 d- and
l-6-Hydroxy-8-(1,1-Dimethylheptyl)-2,3,3a,4-tetrahydro-1H-pyrrolo[1,2-a]quinolin-5-one The dl-2-[1-[3-methoxy-5-(1,1-dimethylheptyl)-phenyl]pyrrolidin-2-yl]acetic acid provided in Example 54, Part A is resolved into dextrorotatory and levorotatory isomers via the alpha-methylbenzylamine salt by the methods of Examples 18 and 19. The resolved isomeric acids are then cyclized to provide the d- and l-isomers of 6-methoxy-8-(1,1-dimethylheptyl)-2,3,3a,4-tetrahydro-1H-pyrrolo[1,2-a]quinolin-5-one. Cleavage of the methyl ether with hydrobromic acid/acetic acid by the procedure of Example 21 affords the title compounds.

EXAMPLE 56

The remaining N-phenylpyrrolidineacetic and N-phenylpiperidineacetic acid derivatives provided in Example 54 are resolved, if desired, by the procedures of Examples 18 and 19, cyclized by the procedures of Examples 20 and 24 and the hydroxyl protecting group, $R_{15}$, removed by the procedure of Example 21, or by catalytic hydrogenation (when $R_{15}$ is benzyl) to provide the corresponding compounds of the formula below where $Z_1$ and t are as defined in Example 54.

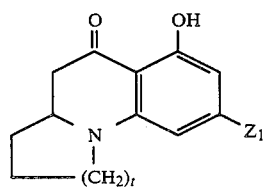

EXAMPLE 57 dl-6-Benzyloxy-5-cyanomethyl-5-hydroxy-8-(1,1-dimethylheptyl)-2,3,3a,4-tetrahydro-1H-pyrrolo[1,2-a]quinoline n-Butyl lithium, 0.68 ml. of 2.2M in hexane (1.48 mmole) is mixed with 0.68 ml. tetrahydrofuran (THF) which had been distilled from sodium metal. The resulting solution is cooled to −78° C. with stirring and 0.077 ml. (1.48 mmole) of acetonitrile added. The resulting slurry is stirred for one hour at −78° C., then a solution of 616 mg. (1.48 mmole) of 6-benzyloxy-8-(1,1-dimethylheptyl)-2,3,3a,4-tetrahydro-1H-pyrrolo[1,2-a]quinolin-5-one in 4 ml. of the same THF is added dropwise to the stirred suspension by a syringe. When the addition is completed, the resulting mixture is stirred for 5 minutes, allowed to warm to room temperature, stirred 10 minutes and the reaction quenched by addition of 0.1 ml. of acetic acid. The mixture is diluted with ethyl ether, washed with saturated sodium bicarbonate solution, water, dried (MgSO₄) and the solvent removed in vacuo to provide the desired product.

EXAMPLE 58 dl-6-Hydroxy-5-cyanomethyl-8-(1,1-Dimethylheptyl)-1,2,3,3a,4,5-hexahydropyrrolo[1,2-a]quinoline A. dl-6-Benzyloxy-5-cyanomethylene-8-(1,1-dimethylheptyl)-1,2,3,3a-tetrahydro-4H-pyrrolo[1,2-a]quinoline To a solution of 10.9 g. (23.7 mmole) dl-6-benzyloxy-5-cyanomethyl-5-hydroxy-8-(1,2-dimethylheptyl)-2,3,3a,4-tetrahydro-1H-pyrrolo[1,2-a]quinoline in 250 ml. dry tetrahydrofuran is added a few grams of molecular sieves and 2.30 g. (23.9 mmole) methanesulfonic acid. The mixture is stirred for 16 hours at room temperature, made alkaline with sodium hydroxide solution, washed with water, the organic layer dried (MgSO₄) and the solvent evaporated in vacuo to afford the crude product which was used in the next step.

B. dl-6-Benzyloxy-5-cyanomethyl-8-(1,1-dimethylheptyl)-1,2,3,3a,4,5-hexahydropyrrolo[1,2-a]quinoline In a flask equipped with magnetic stirrer, thermometer and nitrogen inlet capillary, 1.0 g. of the product of Part A, above, 20 ml. anhydrous methanol and 2.08 g. magnesium turnings are combined. Three crystals of iodine was added at ambient temperature and the mixture stirred until the temperature reached 30° C. It is then cooled to 4° C., stirred at this temperature for 1.5 hours, then overnight at room temperature. An additional 2.0 g. of magnesium turnings and 20 ml. methanol are added. After adding an iodine crystal, the reaction mixture is stirred until the temperature reached 20° C. and gas evolution is well underway. After cooling to −10° C., stirring is continued at −10° to −4° C. for one hour. The cooling bath is removed, the temperature allowed to reach 40° C., then cooled to 20° C. and stirred for four hours. The reaction mixture was cooled to −4° C., 40 ml. of 6N hydrochloric acid and 20 ml. methanol were added over 20 minutes while maintaining the temperature below 10° C. When the bulk of the magnesium was consumed, the mixture is made alkaline with sodium hydroxide solution and extracted with ethyl ether. The extracts are dried (MgSO₄) and evaporated to dryness to afford the crude product which is used in the next step.

C. The product of Part B, above, is dissolved in 150 ml. anhydrous ethanol, 1.1 g. 5% Pd/C is added and the mixture is hydrogenated at 45 psi (3.1 kg./cm.²) for 16 hours. The mixture is filtered and the filtrate evaporated in vacuo. The residue is taken up in 100 ml. methylene chloride, 5 g. of silica gel was added and the slurry evaporated. The residual solid was placed on a column of silica gel and eluted with hexane/ethyl ether. Like fractions are combined and evaporated to dryness to afford the title compound.

D. Repeating the procedures of Example 57 with a benzyl-protected derivative of one of the hydroxy ketones provided in Examples 40, 42 and 56 affords the corresponding 5- (or 6-)hydroxy-5 (or 6-(cyanomethyl compound which is reacted, in turn, by the method of Example 58 to provide compounds of the following formula

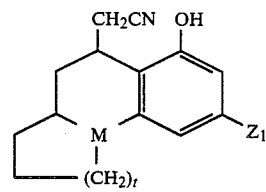

where M, Z and t are as defined in Examples 40, 42 and 54.

EXAMPLE 59 d- and 1-6-Hydroxy-5-Carboxymethylene-8-(1,1-dimethylheptyl)-2,3,3a,4-tetrahydro-1H-pyrrolo[1,2-a]quinoline Lactone and Corresponding Saturated Lactone A. Employing one of the isomers of 6-hydroxy-8-(1,1-dimethylheptyl)-2,3,3a,4-tetrahydro-1H-pyrrolo[1,2-a]quinolin-5-one provided in Example 55 in the procedure of Example 42 provides the corresponding 6-benzyloxy derivative. This is reacted with lithioethyl acetate by the procedure of Example 43 to provide the corresponding 6-benzyloxy-5-ethoxycarbonylmethyl-5-hydroxy-8-(1,1-dimethylheptyl)-2,3,3a,4-tetrahydro-1H-pyrrolo-[1,2-a]quinoline isomer.

B. Hydrogenation of the product obtained in Part A, above, with palladium/carbon catalyst in ethanol at 3 atmospheres pressure and acetylation by the procedure of Example 44 provides a mixture of 6-acetoxy-5-ethoxycarbonylmethylene-8-(1,1-dimethylheptyl)-2,3,3a,4-tetrahydro-1H-pyrrolo[1,2-a]quinoline and the corresponding saturated ester, 6-acetoxy-5-ethoxycarbonylmethyl-8-(1,1-dimethylheptyl)-1,2,3,3a,4,5-hexahydropyrrolo[1,2-a]quinoline.

C. Hydrolysis of the above mixture with sodium hydroxide, potassium hydroxide or potassium carbonate by the method of Example 45 provides the title compounds as mixtures from which the saturated and unsaturated lactones are separated by chromatography.

D. Employing the appropriate starting material selected from the compounds provided in Example 56, the corresponding mixture of saturated and unsaturated lactones is obtained by the above procedure as shown by the reaction sequence below.

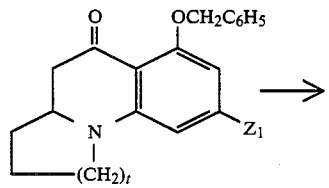

-continued

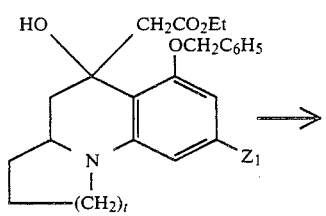

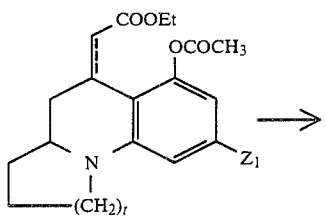

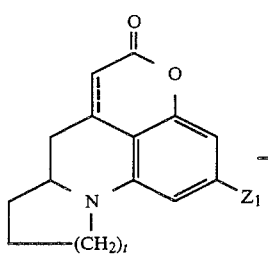

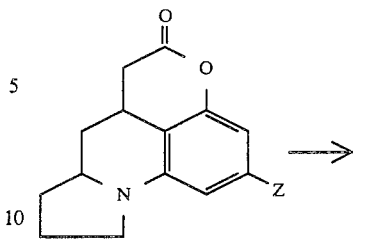

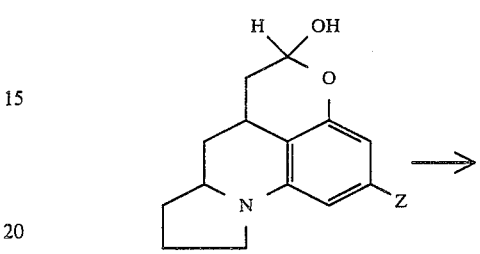

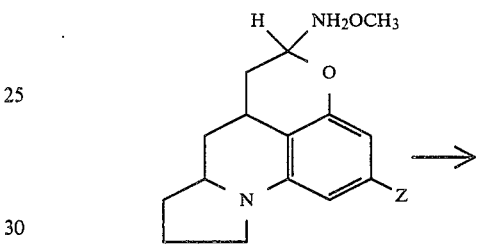

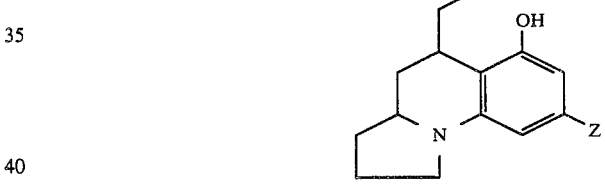

In the above formula $Z_1$ and t are as defined in Example 54 and the broken line is an optional bond.

EXAMPLE 60

Reduction of the unsaturated d- or l-lactone obtained above, with lithium in ammonia by the method of Example 46 affords the corresponding 6-hydroxy-5-beta-(2-hydroxyethyl)-8-(1,1-dimethylheptyl)-1,2,3,3a,4,5-hexahydropyrrolo[1,2-a]quinoline.

The following compounds are obtained in like manner from the appropriate starting material provided above

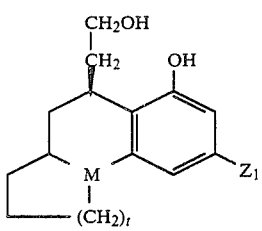

where M, $Z_1$ and t are as defined in Examples 40 and 50.

EXAMPLE 61

Employing the saturated lactones provided in Examples 50 and 59 in the procedures of Examples 47 through 49 similarly provides 6-hydroxy-5-(2-aminoethyl)-8-(1,1-dimethylheptyl)-1,2,3,3a,4,5-hexahydropyrrolo[1,2-a]quinoline as outlined below, where Z is —C(CH$_3$)$_2$(CH$_2$)$_5$CH$_3$.

EXAMPLE 62 dl-7-Hydroxy-6-(2-Cyanoethyl)-9-(5-phenyl-2-pentyloxy)-2,3,4,4a,5,6-hexahydro-1H-pyrido[1,2-a]quinoline A. dl-7-Acetoxy-6-(2-hydroxyethyl)-9-(5-phenyl-2-pentyloxy)-2,3,4,4a,5,6-hexahydro-1H-pyrido[1,2-a]-quinoline A solution of 4.09 g. (0.01 mole) dl-6-(2-hydroxyethyl)-7-hydroxy-9-(5-phenyl-2-pentyloxy)-2,3,4,4a,5,6-hexahydro-1H-pyrido[1,2-a]quinoline in 60 ml. methylene chloride containing 1.01 g. (0.01 mole) triethylamine is cooled to 0° C. while stirring in a nitrogen atmosphere. To this is added a solution of 1.22 g. (0.01 mole) 4-dimethylaminopyridine in 5 ml. of methylene chloride followed by 1.02 g. (0.01 mole) acetic anhydride. After stirring at 0°-5° C. for one hour, the mixture is allowed to warm to room temperature, extracted with methylene chloride and the extracts washed with sodium bicarbonate. After drying over anhydrous magnesium sulfate and evaporation of solvent, the desired product is obtained. It can be purified by column chromatography on silica gel if desired.

The dihydroxy compounds provided in Examples 14, 46, 60 and 64 are converted to the corresponding 6- (or 7-)acetoxy derivatives of the following formula in like manner.

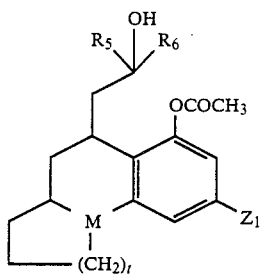

where M is N or CH, t is 1 or 2, $R_5$ and $R_6$ are each hydrogen, methyl, ethyl, n-butyl, benzyl or phenyl and $Z_1$ is as defined in Example 54.

Substitution of acetic anhydride by benzoic anhydride, propionic anhydride, butyric anhydride or valeryl anhydride in this procedure affords the corresponding 5-benzoyloxy, 5-propionyloxy, 5-butyryloxy and 5-valeryloxy derivatives.

B. dl-7-Acetoxy-6-(2-methanesulfonyloxyethyl)-9-(5-phenyl-2-pentyloxy)-2,3,4,4a5,6-hexahydro-1H-pyrido-[1,2-a]quinoline To 4.51 g. (0.01 mole) dl-7-acetoxy-6-(2-hydroxyethyl)-9-(5-phenyl-2-pentyloxy)-2,3,4,4a,5,6-hexahydro-1H-pyrido[1,2-a]quinoline dissolved in 45 ml. pyridine under a nitrogen atmosphere at 0°–5° C. is added with stirring 1.25 g. (0.011 mole) methanesulfonyl chloride. The resulting mixture is stirred at 5° C. for 30 minutes, warmed to room temperature and stirred for an additional hour. The reaction mixture is concentrated in vacuo, the residue taken up in ethyl acetate, washed with water, brine and dried over anhydrous magnesium sulfate. Evaporation of solvent gives the desired mesylate of sufficient purity for use in the next step.

C. A mixture of 4.97 g. (0.01 mole) of the mesylate obtained in Part B, above, 6.5 g. (0.01 mole) potassium cyanide, 800 mg. potassium iodide, 90 g. dimethylformamide and 10 ml. water is heated at 85°–95° C. for two hours. The solvent is evaporated in vacuo, the residue extracted with chloroform, the extracts washed with water, brine and dried (MgSO4). Evaporation of solvent affords the desired nitrile which is purified by chromatography on a silica gel column.

In like manner the remaining dihydroxy compounds provided in Examples 14, 46 and 60 are converted to the 6- (or 7-)-acetoxy derivatives by the procedure of Part A, above, and the acetoxy derivative, in turn, converted to a nitrile of the formula shown below

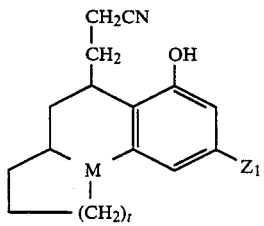

where M, $Z_1$ and t are as defined above for the starting material.

EXAMPLE 63 dl-3-[7-Hydroxy-9-(5-phenyl-2-pentyloxy)-2,3,4,4a,5,6-hexahydro-1H-pyrido[1,2-a]quinolin-6-yl]propionic Acid and Esters To a mixture of 125 ml. methanol and 75 ml. 1N sodium hydroxide is added 4.18 g. (0.01 mole) dl-7-hydroxy-6-(2-cyanoethyl)-9-(5-phenyl-2-pentyloxy)-2,3,4,4a,5,6-hexahydro-1H-pyrido[1,2-a]quinoline and the resulting mixture is heated at reflux overnight. The methanol is evaporated and the residue is extracted between chloroform, backwashing with dilute sodium hydroxide solution. The aqueous alkaline layers are combined, acidified with hydrochloric acid and extracted with chloroform. The extracts are dried over anhydrous magnesium sulfate and the solvent evaporated to provide the desired carboxylic acid.

Heating the above acid, dissolved in a molar excess of alkanol, $R_4OH$, at 50°–110° C. for 4–24 hours in the presence of a catalytic amount of hydrogen chloride or concentrated sulfuric acid provides the corresponding esters of the formula below wherein $R_4$ is methyl, ethyl, n-propyl, isobutyl, n-butyl or benzyl.

Similarly, the remaining nitriles provided above are hydrolyzed to carboxylic acids of the formula below where $R_4$ is hydrogen and esterified as described above:

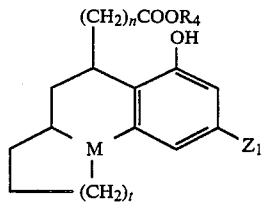

In the formula n is 1 or 2 and M, $Z_1$ and t are as defined for the starting nitrile.

Acetylation of the above 6- (7)-hydroxycarboxylic acid or 6- (7)-hydroxynitriles by the method of Example 62, Part A affords the corresponding 6- (7)-acetoxy derivative.

EXAMPLE 64 dl-7-Hydroxy-6-(3-hydroxypropyl)-9-(5-phenyl-2-pentyloxy)-2,3,4,4a,5,6-hexahydro-1H-pyrido[1,2-a]quinoline A 125 ml., round bottomed flask equipped with a magnetic stirrer and nitrogen inlet is thoroughly flushed with dry nitrogen. Lithium aluminum hydride, 158 mg. (4.2 mmole) and 50 ml. of dry ethyl ether were added and the suspension stirred and cooled in an ice bath. To the cooled mixture is added slowly 1.89 g. (4.2 mmole) methyl dl-3-[7-hydroxy-9-(5-phenyl-2-pentyloxy)-2,3,4,4a,5,6-hexahydro-1H-pyrido[1,2-a]-quinolin-6-yl]propionate dissolved in 20 ml. of ether. The cooling bath is removed and the reaction mixture is stirred at room temperature for 12 hours. Ethyl acetate, 50 ml., is cautiously added to quench the reaction. The resulting mixture is washed with 50 ml. each of saturated sodium bicarbonate solution, brine and water. The organic layer is dried over anhydrous magnesium sulfate, solvent evaporated in vacuo. The residue is purified by chromatography on silica gel.

The corresponding 3-hydroxypropyl derivatives of the formula below are obtained in like manner from the appropriate starting material by the above procedure

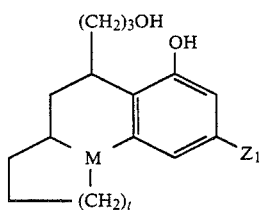

where M, $Z_1$ and t are as defined for the starting ester.

EXAMPLE 65 dl-7-Hydroxy-6-(2-hydroxy-2-methylpropyl)-9-(5-phenyl-2-pentyloxy)-2,3,4,4a,5,6-hexahydro-1H-pyrido[1,2-a]quinoline A. A solution of 405 mg. (1 mmole) of the lactone of dl-6-carboxymethyl-7-hydroxy-9-(5-phenyl-2-pentyloxy)-2,3,4,4a,5,6-hexahydro-1H-pyrido[1,2-a]quinoline, provided in Example 29, in 10 ml. ethyl ether is cooled in an ice bath for 15 minutes. To the cold solution is added slowly by injection 0.80 ml. of 2.9 molar methylmagnesium iodide in ethyl ether. The resulting mixture is allowed to warm to room temperature and stirred for 14 hours. Crystalline ammonium chloride (ca. 100 mg.) is added, the mixture stirred for 20 minutes, water (5 ml.) added and the layers separated. The aqueous layer is extracted with 10 ml. of ether and the combined ether layers are washed with 30 ml. of saturated sodium bicarbonate solution, 30 ml. of brine and 30 ml. of water. The washed organic layer is dried (MgSO4) and solvent evaporated in vacuo to afford the title compound which is purified, if desired, by chromatography.

B. By employing the above procedure, but starting with one of the saturated carbocyclic lactones provided in Examples 45, 50 and 53 or one of the saturated pyrido- (or pyrrolo)-quinoline lactones provided in Examples 59 and 62, and use of the appropriate Grignard reagent of formula $R_5MgHal$ where Hal is Cl, Br or I, in place of methylmagnesium iodide, the following compounds are obtained in like manner.

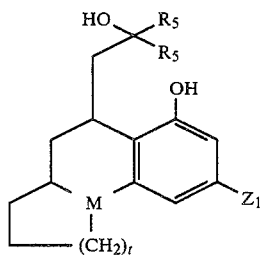

where $Z_1$ and t are as previously defined and $R_5$ is methyl, ethyl, propyl, isopropyl, n-butyl, isobutyl, benzyl or phenyl.

EXAMPLE 66 dl-7-Hydroxy-6-(3-hydroxy-3-methylbutyl)-9-(5-phenyl-2-pentyloxy)-2,3,4,4a,5,6-hexahydro-1H-pyrido[1,2-a]quinoline A solution of 434 mg. (1 mmole) of methyl dl-3-[7-hydroxy-9-(5-phenyl-2-pentyloxy)-2,3,4,4a,5,6-hexahydro-1H-pyrido[1,2-a]quinolin-6-yl]propionate in 20 ml. ethyl ether is cooled to 5° C. and 2.35 ml. of 1M methylmagnesium iodide in ethyl ether is added. The mixture is allowed to warm to room temperature, stirred for 4 hours, then heated at reflux for 4 hours. The reaction mixture is worked up as described in Example 65, Part A to provide the title compound.

Employing the appropriate ester, selected from those provided in Example 63, as starting material and the appropriate Grignard reagent the following compounds are obtained in like manner

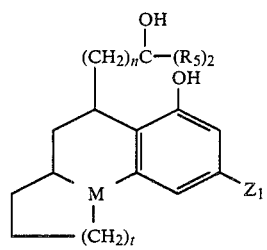

where n, t, M and $Z_1$ are as defined in Example 63 and $R_5$ is methyl, ethyl, isopropyl, n-butyl, benzyl or phenyl.

EXAMPLE 67 dl-7-Hydroxy-6-(3-aminopropyl)-9-(5-phenyl-2-pentyloxy)-2,3,4,4a,5,6-hexahydro-1H-pyrido[1,2-a]quinoline Under anhydrous conditions and a nitrogen atmosphere, to a solution of 190 mg. (5 mmole) lithium aluminum hydride in 50 ml. tetrahydrofuran at 10° C. is added dropwise a solution of 2.09 g. (5 mmole) dl-7-hydroxy-6-(2-cyanoethyl)-9-(5-phenyl-2-pentyloxy)-2,3,4,4a,5,6-hexahydro-1H-pyrido[1,2-a]quinoline in 25 ml. tetrahydrofuran. The mixture is stirred at room temperature for 6 hours after the addition. Ethyl acetate is added to quench the reaction, the solvent is evaporated in vacuo and the residue partitioned between water and methylene chloride. The organic extracts are dried (MgSO4) and the solvent evaporated to provide the title compound as the free base.

The hydrochloride salt of the title compound is obtained by adding ethereal hydrogen chloride to a solution of the free base in anhydrous ethanol. The precipitated salt is collected by filtration, washed with ethyl ether and air dried.

In like manner the remaining nitriles provided above are converted to primary amines of the formula below

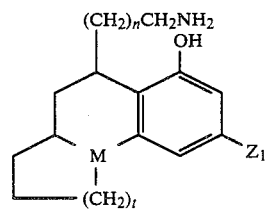

where n is 1 or 2 and t, M and $Z_1$ are as defined in Examples 58 and 62.

EXAMPLE 68 dl-6-(3-Acetylaminopropyl)-7-hydroxy-9-(5-phenyl-2-pentyloxy)-2,3,4,4a,5,6-hexahydro-1H-pyrido[1,2-a]quinoline A. To a solution of 4.22 g. (0.01 mole) dl-7-hydroxy-6-(3-aminopropyl)-9-(5-phenyl-2-pentyloxy)-2,3,4,4a,5,6-hexahydro-1H-pyrido[1,2-a]quinoline in 25 ml. chloroform and 18 ml. dry pyridine at 10° C. is added 2.36 ml. (0.032 mole) acetyl chloride which is dissolved in 10 ml. chloroform. The resulting solution is stirred overnight at room temperature, poured onto ice/water, the organic layer separated and the aqueous phase extracted with chloroform. The combined organic layers are washed with saturated sodium bicarbonate, water, brine and dried over anhydrous magnesium sulfate. Evaporation of solvent affords the diacetate, 7-acetoxy-6-(3-acetylaminopropyl)-9-(5-phenyl-2-pentyloxy)-2,3,4,4a,5,6-hexahydro-1H-pyrido[1,2-a]quinoline, which is purified, if desired, by column chromatography on silica gel.

B. A solution of 506 mg. (1.0 mmole) of the above diacetate and 138 mg. (1 mmole) potassium carbonate in methanol (125 ml.) is stirred at room temperature for two hours. After neutralization with acetic acid the mixture is evaporated in vacuo and the residue taken up in ethyl ether. The ether solution is washed successively with water, saturated sodium bicarbonate, brine and dried over magnesium sulfate. Evaporation of ether affords the title amide.

When acetyl chloride is replaced by an equimolar amount of benzoyl chloride, propionyl chloride, isobutyryl chloride, valeryl chloride, 2-phenylacetyl bromide, trifluoroacetic anhydride or 2-furoyl chloride, the corresponding amido ester compounds are obtained by the procedure of Part A, above. Hydrolysis of the ester by the procedure of Part B, above, affords the corresponding hydroxyamides.

C. In like manner the following compounds are obtained from the primary amines provided above.

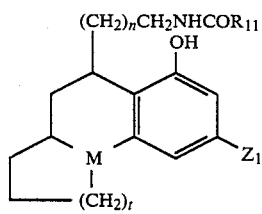

where n, t, M and $Z_1$ are as defined for the starting primary amine and $R_{11}$ is methyl, ethyl, n-propyl, isopropyl, n-butyl, sec-butyl, n-amyl, isoamyl, phenyl, p-tolyl, benzyl, trifluoromethyl, 2-furyl, 2-thienyl, 3-thienyl, 2-pyridyl or 4-pyridyl.

D. When p-toluenesulfonyl chloride is used in place of acetyl chloride in the above procedures the corresponding p-toluenesulfonamide is obtained. Similarly, the following sulfonamido compounds are obtained by the above procedures

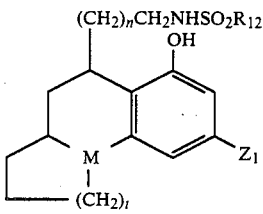

where n, t, M and $Z_1$ are as defined for the starting primary amine and $R_{12}$ is methyl, ethyl, n-propyl, isobutyl, n-butyl, n-amyl, isoamyl, n-hexyl, phenyl, tolyl or benzyl.

EXAMPLE 69

7-Hydroxy-6-carboxamidomethyl-9-(5-phenyl-2-pentyloxy)-2,3,4,4a,5,6-hexahydro-1H-pyrido[1,2-a]quinoline A. A solution of 4.37 g. (0.01 mole) dl-7-hydroxy-6-methoxycarbonylmethyl-9-(5-phenyl-2-pentyloxy)-2,3,4,4a,5,6-hexahydro-1H-pyrido[1,2-a]quinoline in 100 ml. toluene is saturated with anhydrous ammonia at 10° C. The resulting mixture is placed in a sealed tube and heated at 95°-100° C. for six hours. The tube is cooled in ice, then opened and the reaction mixture is evaporated to dryness in vacuo. The residual product is purified by chromatography on silica gel.

B. To a solution of 2.33 g. (5 mmole) dl-2-[7-acetoxy-9-(5-phenyl-2-pentyloxy)-2,3,4,4a,5,6-hexahydro-1H-pyrido[1,2-a]quinoline-6-yl]acetic acid in 50 ml. of chloroform is added dropwise with stirring 0.83 g. (7 mmole) thionyl chloride in 10 ml. of the same solvent. The resulting mixture is stirred at room temperature for one hour, evaporated to dryness at reduced pressure and the residue taken up in 35 ml. ethyl ether. The ethereal solution of acid chloride is added dropwise to a cold solution of 1 g. of ammonia in 50 ml. of ethyl ether. The resulting mixture is stirred for 30 minutes at 10° C., then filtered with suction. The filtrate is washed successively with water, sodium bicarbonate, water, brine and dried over magnesium sulfate. Evaporation of solvent affords the crude 7-acetoxy amide which is taken up in methanol and hydrolyzed with potassium carbonate by the procedure of Example 68, Part B to provide the title compound.

C. By employing the appropriate carboxylic acid ester in the procedure of Part A or the corresponding acetoxy carboxylic acid in the procedure of Part B, and the appropriate amine of formula $R_9R_{10}NH$ in place of ammonia, the following amides are obtained in like manner

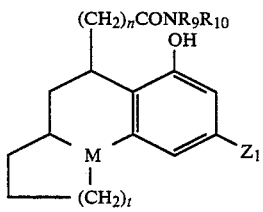

where n, t, M and $Z_1$ are as defined for the starting carboxylic ester or acetoxy acid and $R_9$ and $R_{10}$ are as defined below.

| $R_9$ | $R_{10}$ |
|---|---|
| $CH_3$ | H |
| $CH_3$ | $CH_3$ |
| $C_2H_5$ | H |
| $C_2H_5$ | $C_2H_5$ |
| $(C_2H_5)CHCH_2$ | $C_6H_5$ |
| i-$C_3H_7$ | H |
| n-$C_3H_7$ | $CH_3$ |
| n-$C_6H_{13}$ | n-$C_4H_9$ |
| n-$C_6H_{13}$ | n-$CH_6H_{13}$ |
| $C_6H_5$ | H |
| $C_6H_5$ | $C_6H_5$ |
| $C_6H_5CH_2$ | $C_6H_5$ |
| $C_6H_5CH_2$ | $C_6H_5CH_2$ |
| $C_6H_5CH_2$ | $CH_3$ |
| $C_6H_5$ | n-$CH_4H_9$ | or when taken together, $NR_9R_{10}$ is: morpholinyl, piperidinyl, pyrrolidinyl, N-methylpiperazinyl, N-ethylpiperazinyl, N-isopropylpiperazinyl or N-n-butylpiperazinyl.

EXAMPLE 70 dl-7-Hydroxy-6-(3-N,N-dimethylaminopropyl)-9-(5-phenyl-2-pentyloxy)-2,3,4,4a,5,6-hexahydro-1H-pyrido[1,2-a]quinoline Under nitrogen and anhydrous conditions 2.32 g. (5 mmole) dl-N,N-dimethyl 3-[7-hydroxy-9-(5-phenyl-2-pentyloxy)-2,3,4,4a,5,6-hexahydro-1H-pyrido[1,2-a]-quinolin-6-yl]propionamide is reduced with lithium aluminum hydride in tetrahydrofuran by the procedure of Example 67 to afford the title compound as the free base. The dihydrochloride salt is obtained by adding two equivalents of ethereal hydrogen chloride to a solution of the free base in ethanol, filtration, and washing the precipitate with ethyl ether.

In like manner the remaining amides provided in the preceding Example are converted to amines of the formula below

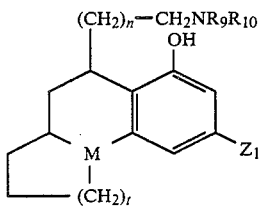

wherein n, t, M, $Z_1$, $R_9$ and $R_{10}$ are defined in Example 69.

EXAMPLE 71 dl-6-(2-Formylethyl)-7-hydroxy-9-(5-phenyl-2-pentyloxy)-2,3,4,4a,5,6-hexahydro-1H-pyrido[1,2-a]quinoline To a solution of 80 ml. 0.5M disiamylborane (40 mmole) in tetrahydrofuran under dry nitrogen is added dropwise a solution of 9.28 g. (0.02 mole) dl-N,N-dimethyl-3-[7-hydroxy-9-(5-phenyl-2-pentyloxy)-2,3,4,4a,5,6-hexahydro-1H-pyrido[1,2-a]quinolin-6-yl]propionamide in 50 ml. tetrahydrofuran and the resulting mixture stirred at ambient temperature for six hours. A mixture of 50 ml. each of glycerin and water is added and stirring continued until gas evolution is complete. The tetrahydrofuran is evaporated in vacuo, the residue extracted with ethyl ether, the extracts washed with water, dried (MgSO$_4$) and evaporated to provide the title compound. The product is purified by chromatography on silica gel.

In like manner compounds of the following formula are obtained from the corresponding N,N-dimethylamide obtained as directed in Example 69:

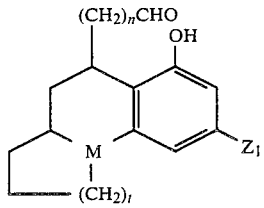

where n, t, M and $Z_1$ are as defined for the starting N,N-dimethylamide.

EXAMPLE 72 dl-7-Hydroxy-6-(3-hydroxypentyl)-9-(5-phenyl-2-pentyloxy)-2,3,4,4a,5,6-hexahydro-1H-pyrido[1,2-a]quinoline A solution of 598 mg. (1.42 mmole) dl-6-(2-formylethyl)-7-hydroxy-9-(5-phenyl-2-pentyloxy)-2,3,4,4,a,5,6-hexahydro-1H-pyrido[1,2-a]quinoline in 10 ml. ethyl ether is cooled in ice for 15 minutes. From a syringe, 1.58 ml. of 2.9M ethyl magnesium iodide is added slowly with stirring. The reaction mixture was allowed to warm to room temperature and stirred for three hours. Ammonium chloride crystals (ca. 100 mg.) was added to consume the unreacted Grignard reagent and the mixture stirred for 20 minutes. Ethyl acetate, 75 ml., and water, 50 ml., were added, the mixture stirred for a few minutes, and the layers separated. The aqueous layer was extracted with 50 ml. of ethyl acetate and the combined organic layers washed with 50 ml. each of water, brine and water again. The organic layer was dried over anhydrous magnesium sulfate and solvent evaporated in vacuo to obtain the crude product which is purified, if desired, by chromatography.

The compounds of the formula below are obtained in like manner from the aldehydes provided in the previous Example and the appropriate Grignard reagent, $R_5MgHal$.

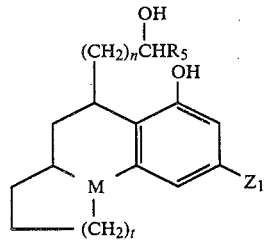

where Hal is Cl, Br or I; n, t, M, $Z_1$ and $R_5$ are as defined in Examples 65 and 66.

EXAMPLE 73 dl-7-Hydroxy-6-(3oxopentyl)-9-(5-phenyl-2-pentyloxy)-2,3,4,4a,5,6-hexahydro-1H-pyrido[1,2-a]quinoline A solution of 5.0 g. (0.02 mole) chromic anhydride in 5.0 ml. water is added with stirring and ice cooling to 50 ml. pyridine. To this is added at 10° C., 4.93 g. (0.01 mole) dl-7acetoxy-6-(3-hydroxypentyl)-9-(5-phenyl-2-pentyloxy)-2,3,4,4a,5,6-hexahydro-1H-pyrido[1,2- a]quinoline (prepared from dl-7-hydroxy-6-(3-hydroxypentyl-9-(5-phenyl-2-pentyloxy)-2,3,4,4a,5,6-hexahydro-1H-pyrido[1,2-a]quinoline by the procedure of Example 62, Part A) and the resulting mixture is stirred at ambient temperature for three hours. The mixture is then poured into water, made alkaline with sodium hydroxide and extracted with methylene chloride. The combined extracts are washed with water, brine, dried (MgSO$_4$) and the solvent evaporated in vacuo. The residue is purified by silica gel chromatography.

In like manner, the remaining secondary alcohols provided in Example 72 are oxidized to the corresponding ketones of the formula below.

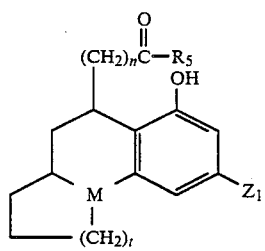

EXAMPLE 74

The 6- or 7-hydroxy ketones provided in the preceding Example are converted to the corresponding 6- or 7-acetyl ketones by the procedure of Example 62, Part A, the products thus obtained are reacted with 3–4 moles of Grignard reagent, R$_6$MgCl or R$_6$MgBr, by the procedure of Example 72 to provide 6- or 7-hydroxytertiary alcohols of the formula

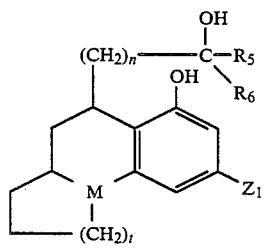

where t, M and Z$_1$ are as defined in Example 72 and M, R$_5$ and R$_6$ are as defined below.

| n | R$_5$ | R$_6$ |
|---|---|---|
| 0 | CH$_3$ | C$_2$H$_5$ |
| 0 | C$_2$H$_5$ | C$_6$H$_5$CH$_2$ |
| 0 | n-CH$_4$H$_9$ | CH$_3$ |
| 0 | CH$_2$CH(CH$_3$)$_2$ | C$_6$H$_5$ |
| 0 | n-CH$_4$H$_9$ | n-CH$_4$H$_9$ |
| 1 | CH$_3$ | C$_6$H$_5$ |
| 1 | n-CH$_3$H$_7$ | i-C$_4$H$_9$ |
| 1 | C$_2$H$_5$ | C$_6$H$_5$ |
| 1 | n-CH$_4$H$_9$ | C$_6$H$_5$CH$_2$ |
| 1 | C$_6$H$_5$CH$_2$ | C$_6$H$_5$ |

EXAMPLE 75

Acetylation of the primary and secondary alcohols provided in the above Examples with acetic anhydride in pyridine by the procedure of Example 29, Part B provides the corresponding diacetates of the formula below where R$_1$ and R$_7$ are both acetyl.

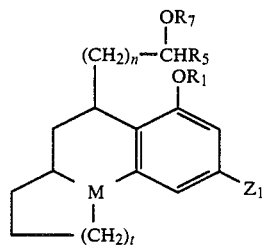

Room temperature hydrolysis of the diacetate with potassium carbonate/methanol by the procedure of Example 68, Part B affords the corresponding compound where R$_1$ is H and R$_7$ is acetyl.

In like manner when the acetic anhydride in the above procedure is replaced by an acid anhydride [(R$_7$'CO)$_2$O] or acid chloride (R$_7$'COCl) where R$_7$' is ethyl, n-propyl, or isopropyl the corresponding diacyl compounds of the formula above are obtained. Similarly, hydrolysis with potassium carbonate in methanol at room temperature affords the corresponding monoacyl compounds where R$_1$ is H and R$_7$ is said acyl.

EXAMPLE 76

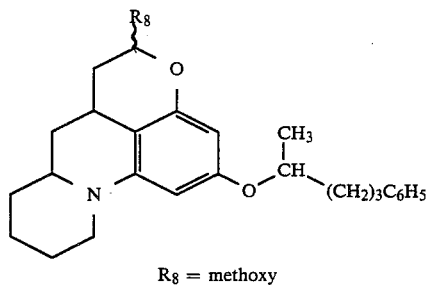

R$_8$ = methoxy

The starting lactol of the above formula where R$_8$ is hydroxy is obtained from the corresponding saturated lactone by the method of Example 47.

A mixture of 419 mg. (1.0 mmol) of the lactol, 700 mg. ammonium chloride and 250 ml. methanol is stirred at room temperature for 14 hours. The mixture is filtered through a bed of anhydrous magnesium sulfate, the solvent evaporated in vacuo, and the residue is partitioned between water and ethyl ether. The organic layers are dried (MgSO$_4$) and solvent evaporated in vacuo to afford the desired methyl ether (formula above, R$_8$=OCH$_3$) as a mixture of diastereomers which can be separated by chromatography on silica gel to afford the dl-alpha-methoxy and dl-beta-methoxy isomers.

When the methanol used in the above procedure is replaced by ethanol, n-propanol, isopropanol, n-butanol or isobutanol the analogous compounds of the above formula are obtained in like manner.

Use of the appropriate lactol and alcohol as starting materials in the above procedures provides the compounds of the formula below

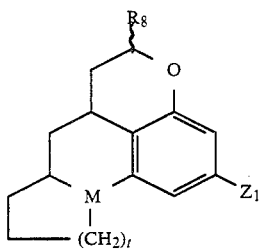

where $R_8$ is methoxy, ethoxy, n-propoxy, isopropoxy, n-butoxy or isobutoxy and t, M and $Z_1$ are as defined for the starting lactol.

EXAMPLE 77 dl-7-Hydroxy-6-[2-(5-tetrazolyl)ethyl]-9-(5-phenyl-2-pentyloxy)-2,3,4,4a,5,6-hexahydro-1H-pyrido[1,2-a]quinoline Finely ground sodium azide (325 mg., 5 mmole) is added to a solution of 7-acetoxy-6-(2-cyanoethyl)-9-(5-phenyl-2-pentyloxy)-2,3,4,4a,5,6-hexahydro-1H-pyrido[1,2-a]quinoline (506 mg., 1 mmole) in 5 ml. of ethanol-free chloroform containing 271 mg. (2 mmole) N-methylpiperidine hydrochloride and 5 drops of N-methylpiperidine. The mixture is heated at reflux for one hour, another 2 mmole of N-methylpiperidine hydrochloride is added, refluxing continued for another hour and allowed to stand overnight at room temperature. The mixture is partitioned between chloroform and aqueous sodium carbonate solution. The aqueous layer is adjusted to pH 5, extracted again with chloroform and the combined organic layers washed with water and the chloroform is dried ($MgSO_4$). Evaporation of solvent under reduced pressure affords the title compound.

In similar manner the nitriles provided above are converted to 5-tetrazolyl derivatives of the formula below

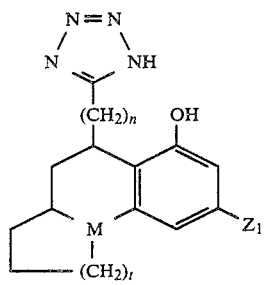

where n, t, M and $Z_1$ are as defined for the starting nitrile.

EXAMPLE 78 dl-6-(2-Acetoxyethyl)-7-(4-N-piperidylbutyryloxy)-9-(5-phenyl-2-pentyloxy)-2,3,4,4a,5,6-hexahydro-1H-pyrido[1,2-a]quinoline Hydrochloride To a solution of 1.13 g. (2.5 mmole) dl-6-(2-acetoxyethyl)-7-hydroxy-9-(5-phenyl-2-pentyloxy)-2,3,4,4a,5,6-hexahydro-1H-pyrido[1,2-a]quinoline in 25 ml. methylene chloride is added 0.52 g. (2.5 mmole) 4-N-piperidylbutyric acid hydrochloride, 0.573 g. (2.78 mmole) dicyclohexylcarbodiimide and the mixture stirred at room temperature for six hours. It is cooled at 0° C. overnight, filtered, the filtrate evaporated and the residue triturated with ethyl ether to afford the desired hydrochloride salt.

Alternatively, the above filtrate is extracted with dilute hydrochloric acid. The aqueous phase is washed with ether, then neutralized with potassium hydroxide solution and extracted with ether. Evaporation affords the free base of the title compound.

Repetition of this procedure by employing the appropriate 6- (or 7)-hydroxy compound provided above provides the following compounds

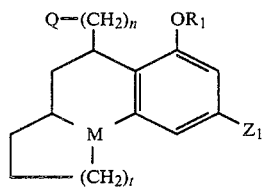

where n, t, M, Q and $Z_1$ are as defined for the above starting material and $R_1$ is as defined below.

| $R_1$ |
|---|
| $COCH_2CH_3$ |
| $CO(CH_2)_2CH_3$ |
| $CO(CH_2)_3CH_3$ |
| $COCH_2NH_2$ |
| $CO(CH_2)_2NH_2$ |
| $CO(CH_2)_4NH_2$ |
| $CO(CH_2)N(CH_3)_2$ |
| $CO(CH_2)_2NH(C_2H_5)$ |
| $CO(CH_2)_4NHCH_3$ |
| $CONH_2$ |
| $CON(C_2H_5)_2$ |
| $CON(C_4H_9)_2$ |
| $CO(CH_2)_3NH(C_3H_7)$ |
| $CO(CH_2)_2N(C_4H_9)_2$ |
| $COCH_2$—piperidino |
| $COCH_2$—pyrrolo |
| $CO(CH_2)_2$—morpholino |
| $CO(CH_2)_2$—N—butylpiperazino |
| $CO(CH_2)_3$—pyrrolidino |
| CO—piperidino |
| CO—morpholino |
| CO—pyrrolo |
| CO—N—(methyl)piperazino |
| $CO$—$C_6H_5$ |
| $COCH(CH_3)(CH_2)_2$—piperidino |
| CHO |

Basic esters are obtained as their hydrochloride salts. Careful neutralization with sodium hydroxide affords the free basic esters.

EXAMPLE 79

General Hydrochloride Acid Addition Salt Formation

Into an ethereal solution of the appropriate free base of formula (I), where one or more of M, $R_1$, Q and Z is a basic nitrogen containing group, is passed a molar excess of anhydrous hydrogen chloride and the resulting precipitate is separated and recrystallized from an appropriate solvent, e.g. methanol-ether.

Similarly, the free bases of formula (I) are converted to their corresponding hydrobromide, sulfate, nitrate, phosphate, acetate, butyrate, citrate, malonate, maleate, fumarate, malate, glycolate, gluconate, lactate, salicylate, sulfosalicylate, succinate, pamoate and tartarate salts.

EXAMPLE 80

6-Hydroxy-5-(2-hydroxyethyl)-8-(5-phenyl-2S-pentyloxy)-1,2,3,3aS,4,5R-hexahydropyrrolo[1,2-a]quinoline, 100 mg., is intimately mixed and ground with 900 mg. of starch. The mixture is then loaded into telescoping gelatin capsules such that each capsule contains 10 mg. of drug and 90 mg. of starch.

EXAMPLE 81

A tablet base is prepared by blending the ingredients listed below:

| Sucrose | 80.3 parts |
|---|---|
| Tapioca starch | 13.2 parts |
| Magnesium stearate | 6.5 parts |

7-Hydroxy-6-(2-hydroxyethyl)-9-(5-phenyl-2S-pentyloxy)-2,3,4,4aS,5,6R-hexahydro-1H-pyrido[1,2-a]quinoline is blended into this base to provide tablets containing 0.1, 0.5, 1, 5, 10 and 25 mg. of drug.

EXAMPLE 82

Suspensions of 7-hydroxy-6-(2-hydroxyethyl)-9-(5-phenyl-2RS-pentyloxy)-1,2,3,4,4aS,5,6R,10bS-octahydrophenanthrene are prepared by adding sufficient amounts of drug to 0.5% methylcellulose to provide suspensions having 0.05, 0.1, 0.5, 1, 5 and 10 mg. of drug per ml.

PREPARATION 1

5-Phenyl-2-pentyl Mesylate

To a stirred solution of 5-phenyl-2-pentanol (482 g.; 2.94 moles) in tetrahydrofuran (2250 ml.) at 0° C. was added methanesulfonyl chloride (300 ml.) at such a rate that the internal temperature does not rise above 10° C. (total addition time 4.5 hours). After addition is complete, the reaction mixture was allowed to warm to room temperature and stirring was continued for an additional hour. The reaction mixture was filtered and the supernate concentrated to a light yellow oil (2800 g.) which was dissolved in chloroform (2 liters) and washed with water (4×1 liter), brine (1×1 liter), charcoal treated (50 g.), dried (MgSO$_4$), filtered through diatomaceous earth and concentrated to a light orange oil (687 g., 95% yield). This material was suitable for use without further purification.

$^1$H-NMR (CDCl$_3$): 7.23 (s, 5H, aromatic), 4.53–5.13 (m, 1H, —CH—O—), 2.93 (s, 3H, O—SO$_2$—CH$_3$), 2.42–2.93 (m, 2H, —CH$_2$C$_6$H$_5$), 1.50–1.92 [m, 4H, —(CH$_2$)$_2$—], 1.23 (s, 3H, O—CH—CH$_3$) ppm.

PREPARATION 2

5-Phenyl-2R-pentyl Mesylate

By the method of Preparation 1, 5-phenyl-2R-pentanol is converted to title product.

PREPARATION 3

5-Phenyl-2S-pentyl Mesylate

By the method of Preparation 1, 5-phenyl-2S-pentanol was converted to title product.

Likewise, 4-phenyl-2S-butanol and 6-phenyl-2S-hexanol are converted to the corresponding mesylates.

PREPARATION 4

4-Phenyl-1-butyl Mesylate

By the method of Preparation 1, 4phenyl-1-butanol was converted to title product, a yellow oil; m/e 228; $^1$H-NMR (CDCl$_3$): 7.22 (bs, 5H, aromatic), 4.08–4.34 (m, 2H, —CH$_2$—O—), 3.93 (s, 3H, SO$_2$CH$_3$), 2.40–2.82 (m, 2H, CH$_2$C$_6$H$_5$), 1.51–1.93 (m, 4H, —CH$_2$CH$_2$—) ppm.

PREPARATION 5 d(+)-2-Octyl mesylate and l(−)-2-Octyl mesylate

By the method of Preparation 1, the optically active forms of 2-octanol were converted to:

l(−)-2-octyl mesylate, a colorless oil, [alpha]$_D^{25}$ = −9.695° (CHCl$_3$, C=2.6), $^1$H-NMR (CDCl$_3$): 4.79 (bg, 1H, —CH—O—), 2.97 (s, 3H, S—CH$_3$), 1.40 (d, 3H, CH$_3$—CH), 0.87 (t, 3H, CH$_3$CH$_2$), 1.0–2.0 [m, 10H, —(CH$_2$)$_5$—] ppm; and d(+)-2-octyl mesylate, [alpha]$_D^{25}$ = +9.238° (CHCl$_3$, C=2.8), $^1$H-NMR identical to the l(−) form.

PREPARATION 6

By the method of Preparation 1, the following mesylates are prepared from the corresponding alcohols 2-phenyl-1-butyl mesylate;
3-phenyl-1-butyl mesylate;
1-phenyl-2-butyl mesylate;
4-phenyl-2-butyl mesylate;
5-phenyl-1-pentyl mesylate;
3-(3-pyridyl)-1-propyl mesylate;
1-tridecanyl mesylate;
1-dodecyl mesylate;
2-decyl mesylate;
4-decyl mesylate;
3-octyl mesylate;
4-heptyl mesylate;
5-methyl-2-hexyl mesylate;
4-methyl-1-pentyl mesylate;
1-(3-chlorophenyl)-1-butyl mesylate; and
1-(3-fluorophenyl)-1-propyl mesylate.

PREPARATION 7

Ethyl 2-(2-Phenylethyl)acetoacetate

Ethyl acetoacetate (53.8 g., 0.29 mole) was dissolved in 110 ml. of anhydrous ethanol. Sodium methoxide (17.3 g., 0.36 mole) was added portionwise to the stirred solution, allowing the temperature to rise to 40°–50°. The mixture was then heated to reflux (80°–82°) and phenethyl bromide (53.8 g., 0.32 mole) added dropwise over 1 hour. Reflux was continued for 20 hours. The reaction mixture was cooled to 30°–35° and filtered over diatomaceous earth with ethanol wash. The combined filtrate and wash were concentrated in vacuo to a pot temperature of 50°, cooled to 25°, diluted with 150 ml. of hexane and 40 ml. of water, acidified to pH 6.5–7.0 with 6N HCl. The hexane layer was separated and washed with 25 ml. of fresh water. The aqueous layer were combined and back-washed with 40 ml. of fresh hexane. The hexane layers were combined, washed with 60 ml. of water, dried over 15 g. MgSO$_4$, filtered and evaporated to yield title product as an oil (62 g., 91%).

PREPARATION 8

5-Phenyl-2-pentanone

Product of the preceding Preparation (30.5 g., 0.13 mole) was combined with 130 ml. of ethanol, 25 ml. of water and KOH (85%, 20.6 g., 0.31 mole). The reaction mixture was refluxed for 3 hours, cooled, concentrated in vacuo to 80 ml., and diluted with 90 ml. of water and 60 ml. of hexane. The water layer was separated and washed with 40 ml. of fresh hexane. The combined organic layers were back-washed with 30 ml. of water, dried (MgSO$_4$), filtered and stripped of solvent to yield 12.8 g. of crude product as an oil, purified by distillation (9.5 g., b.p. 104°/2 mm.).

PREPARATION 9

5-Phenyl-2-pentanol

Under nitrogen, sodium borohydride (755 mg., 0.02 mole) was dissolved in 30 ml. of absolute ethanol and cooled to 0°-5°. Ketone of the preceding Preparation (10.3 g., 0.064 mole) was added dropwise with stirring over 30 minutes, maintaining the temperature 5°-15°. The temperature was increased to 22° for 2 hours, and then reduced to 10°-12° as 3 ml. of methanol was added over 5 minutes and 2 ml. of concentrated HCl was added over 30 minutes. The quenched reaction mixture was poured into 20 ml. of water and extracted with hexane (50 ml.). The extract was dried (MgSO$_4$), filtered, concentrated to an oil and distilled to yield title product (8.7 g., 83%, b.p. 90°-100°/0.3 mm.).

PREPARATION 10

5-Phenyl-2-pentyl Hydrogen Phthalate

Phthalic anhydride (21.5 g., 0.145 mole) was stirred with the alcohol of the preceding Preparation (23.7 g., 0.145 mole) and heated to 90°. The temperature is gradually increased to 130°, an exotherm occuring at some point above 90°. The temperature, when the exotherm occurs is not allowed to rise above 155°. Following the exotherm, the reaction is maintained at 130°-140° for 1 hour, then cooled to 50° and diluted with 125 ml. of acetonitrile. The resulting solution of title product is used directly in the next step.

PREPARATION 11

5-Phenyl-2S-pentyl Brucine Phthalate

Brucine (57.6 g., 0.146 mole) in 105 ml. of acetonitrile was added to the acetonitrile solution of ester from the preceding Preparation and the mixture heated to 55°-60°. Maintaining this temperature, isopropyl ether (610 ml.) is added in a steady stream. The solution is cooled gradually to 23°, and the crystalline material which begins to form at 45°-55°, granulated for 16 hours, recovered by filtration and air dried at 55° (33 g.). Highly resolved material has [alpha]$_D^{CHCl_3}$+40.0. If at this stage the rotation is less than +38.5°, it is recrystallized from acetonitrile-isopropyl ether (for 33 g. of crude, 130 ml. of acetonitrile and 300 ml. of isopropyl ether was used, with recovery of 26 g. of purified title product).

PREPARATION 12

5-Phenyl-2S-pentanol

S-Brucine salt of the preceding Preparation (10.0 g., 14.2 mmoles) was combined with 125 ml. of toluene and 150 ml. of water. With stirring the pH was adjusted to 1.7 with about 6 ml. of 3N HCl. The aqueous layer was separated and extracted 2×40 ml. toluene. Brucine was precipitated from the aqueous layer by adjusting the pH to 11.5 with 50% NaOH. Recrystallization from isopropyl alcohol provides material suitable for reuse. The toluene layers were combined, back-washed with 75 ml. of water, concentrated to 45-50 ml. Fresh water (65 ml.) and then KOH (85%, 1.90 g., 28.8 mmoles) were added and the mixture stirred for 1 hour at room temperature and then 2 hours at 82°-84°. The reaction mixture was cooled to 25°, the toluene layer separated and the aqueous layer washed 3×20 ml. toluene. The toluene layers were combined, washed 1×20 ml. saturated NaCl, dried (MgSO$_4$), filtered and concentrated to yield title product as an oil (1.91 g.), purified by distillation in vacuo (1.64 g., b.p. 85°-92°/0.1 mm., [alpha]$_D^{25}$+8.24 to +8.57°).

PREPARATION 13

5-Phenyl-2R-pentanol

To a solution of racemic 5-phenylpentan-2-ol (4.9 g., 0.03 mole) in 50 ml. toluene was added d-mandelic acid (4.5 g., 0.03 mole) and a trace of p-toluenesulfonic acid. This mixture was heated for 10 hours at reflux using a Dean Stark device to remove water. Upon cooling, 50 ml. of benzene was added and the reaction washed with 3×100 ml. of saturated NaHCO$_3$ solution, the organic phase dried (MgSO$_4$) and concentrated to yield 7.0 g. of a colorless oil (78%). A portion of this oil (5.4 g.) was subjected to column chromatographic separation using 500 g. of silica gel and an ethyl ether-hexane (1 to 4) solvent system. The separation of the diastereomeric mandelates could conveniently be followed by $^1$H-NMR. The first eluting 5-phenyl-2R-pentanol had the CH$_3$ doublet (J=7.0) centered at 1.05 ppm and the second eluting 5-phenyl-2S-pentanol at 1.25 ppm. Using a fraction collector, 150 15 ml. fractions were collected from the above column. Fractions 101-110 show an isomer ratio of ca. 95:5 of the first eluting isomer (HPLC). These fractions were combined and concentrated to yield 0.90 g.; [alpha]$_D^{25}$=37.56° (CHCl$_3$).

A portion of the purified first eluting isomer (0.80 g., 0.0027 mole) was dissolved in 25 ml. of methanol and 2.0 ml. of H$_2$O and 0.50 g. of K$_2$CO$_3$ (0.0036 mole) was added and this reaction stirred for 24 hours at 25°. Water (10 ml.) was then added and the reaction extracted with 2×25 ml. of EtOAc; the organic layers combined, dried (MgSO$_4$) and concentrated to yield 0.40 g. (90%) of 5-phenylpentan-2-ol, [alpha]$_D^{25}$=7.16° (CHCl$_3$).

PREPARATION 14

5-Phenyl-2S-pentanol

A sample of 9.9 g. (0.043 mole) of S(+)-propylene glycol 1-tosylate prepared from L-ethyl lactate according to Gombos et al., Chem. Ber. 109, p. 2145 (1976), was dissolved in 20 ml. of dry THF. This solution was added dropwise over 15 minutes to a rapidly stirred mixture of 98 ml. of 1.1M phenethyl magnesium bromide in THF (0.11 mole), immediately after 1.05 g. of cuprous chloride was added in one portion to the Grignard. The temperature of the initial cuprous chloride addition and of the subject tosylate addition was maintained at 18°-25° (upon the addition of the CuCl$_2$, the Grignard solution turned a deep purple). The reaction was then stirred for 1 hour at 25°, and quenched into 30 ml. of saturated NH$_4$Cl solution. The aqueous phase was separated and extracted 2× with 100 ml. portions of ethyl ether. The combined organic layer and washings were washed with brine (2×100 ml.), dried (MgSO$_4$) and concentrated to give 10.98 g. of crude title product as an oil. The pure S(+)-5-phenylpentan-2-ol was obtained by fractional high vacuum distillation. The purified S(+)-5-phenylpentan-2-ol had [alpha]$_D^{25}$=+7.94 (CHCl$_3$).

Other appropriate Grignard reagents are substituted for phenylethyl magnesium bromide to prepare a wide variety of other optically active alcohols useful in the present invention. Exemplary are:
4-phenyl-2S-butanol;
6-phenyl-2S-hexanol; and
2S-octanol.

PREPARATION 15

3-Bromo-5-(2-undecyl)anisole

3-Amino-5-(2-undecyl)anisole, prepared according to methods set forth by Johnson, U.S. Pat. No. 4,260,764 is diazotized and converted to the title compound according to procedures set forth by Bigelow, Org. Syntheses, Coll. Vol. I, pp. 135–137 (1941).

In the same manner, other aminoanisoles, also prepared by methods set forth by Johnson, are converted to:

3-bromo-5-(2-hexyl)anisole;
3-bromo-5-(3-ethyl-1-pentyl)anisole;
3-bromo-5-(5-phenyl-1-hexyl)anisole;
3-bromo-5-(6-phenyl-2-hexyl)anisole;
3-bromo-5-(6-phenyl-3-hexyl)anisole;
3-bromo-5-[6-(4-chlorophenyl)-2-hexyl]anisole;
3-bromo-5-[5-(4-fluorophenyl)-2-pentyl]anisole;
3-bromo-5-[6-(4-pyridyl)-2-hexyl]anisole;
3-bromo-5-[1-(1-heptyloxy)-2-propyl]anisole; and
3-bromo-5-[2-(2-phenylethoxy)-1-propyl]anisole.

PREPARATION 16

3-Methoxy-5-(2-undecyl)benzonitrile

3-Amino-5-(2-undecyl)anisole is diazotized and reacted with cuprous cyanide according to procedures set forth by Clarke and Read, Org. Syntheses, Coll. Vol. I, pp. 514–516 (1941) to produce the title product.

In the same manner other appropriate aminophenols are converted to:
3-methoxy-5-(5-phenyl-2-methyl-1-pentyl)benzonitrile;
3-methoxy-5-[5-(2-chlorophenyl)-1-hexyl]benzonitrile;
3-methoxy-5-[7-(3-fluorophenyl)-3-heptyl]benzonitrile; and
3-methoxy-5-[8-(3-pyridyl)-1-octyl]benzonitrile.

PREPARATION 17

3-Methoxy-5-(2-undecyl)benzoic Acid

The title nitrile of the preceding Preparation is hydrolyzed in methanolic sodium hydroxide at reflux. After five hours, the reaction mixture is neutralized with dilute hydrochloric acid, the methanol evaporated in vacuo and the aqueous residue extracted with ethyl acetate. Evaporation of solvent affords the title acid.

By the same method, the other nitriles of the preceding Preparation are converted to:
3-methoxy-5-(5-phenyl-2-methyl-1-pentyl)benzoic acid;
3-methoxy-5-[5-(2-chlorophenyl)-1-hexyl]benzoic acid;
3-methoxy-5-[7-(3-fluorophenyl)-3-heptyl]benzoic acid; and
3-methoxy-5-[8-(3-pyridyl)-1-octyl]benzoic acid.

If desired, the 3-methoxy-5-(2-undecyl)benzoic acid is resolved into its enantiomeric forms via salt formation with an optically active base, as set forth by Feiser and Fieser, Reagents for Organic Syntheses, John Wiley and Sons, 1967, pp. 977–978, thus affording:
3-methoxy-5-(2S-undecyl)benzoic acid; and
3-methoxy-5-(2R-undecyl)benzoic acid.

In like manner, 3-methoxy-5-(5-phenyl-2-methyl-1-pentyl)benzoic acid is resolved to yield:
3-methoxy-5-(5-phenyl-2S-methyl-1-pentyl)benzoic acid; and
3-methoxy-5-(5-phenyl-2R-methyl-1-pentyl)benzoic acid.

PREPARATION 18

3-Methoxy-5-(2-undecyl)benzoyl Chloride

The title acid of the preceding Preparation is reacted with excess thionyl chloride in methylene chloride diluent in the presence of a trace of dimethylformamide. After refluxing for 3 hours the acid chloride is recovered by evaporation of the solvent and excess thionyl chloride chased with toluene.

By the same method, the other acids of the preceding Preparation are converted to:
3-methoxy-5-(5-phenyl-2-methyl-1-pentyl)benzoyl chloride;
3-methoxy-5-[5-(2-chlorophenyl)-1-hexyl]benzoyl chloride;
3-methoxy-5-[7-(3-fluorophenyl)-3-heptyl]benzoyl chloride;
3-methoxy-5-[8-(3-pyridyl)-1-octyl]benzoyl chloride;
3-methoxy-5-(2S-undecyl)benzoyl chloride;
3-methoxy-5-(2R-undecyl)benzoyl chloride;
3-methoxy-5-(5-phenyl-2S-methyl-1-pentyl)benzoyl chloride; and
3-methoxy-5-(5-phenyl-2R-methyl-1-pentyl)benzoyl chloride.

PREPARATION 19

3-Methoxy-5-(2-undecyl)benzaldehyde

Method A

The title acid chloride of the preceding Preparation is subjected to hydrogenation under Rosenmund conditions, as set forth by Mosettig and Mozingo in Organic Reactions, Vol. 4, John Wiley and Sons, New York, 1948, pp. 362–377, producing the title product.

Method B

The title nitrile of Preparation 16 is subjected to the Stephen reduction under conditions set forth by Williams, Org. Syntheses, Coll. Vol. III, pp. 626–627 (1955).

Method C

The title acid chloride of the preceding Preparation is reacted with excess ethyl mercaptan to yield the corresponding thiol ester. Hydrogenolysis to the title aldehyde is effected by refluxing the thiol ester with Raney nickel in ethanol under conditions set forth by Wolfrom and Karbinos, J. Am. Chem. Soc. 68, pp. 1455–1456 (1946).

Method D

3-Methoxy-5-(2-undecyl)benzyl bromide is oxidized according to methods set forth by Kornblum et al., J.

Am. Chem. Soc. 81, pp. 4113–4114 (1959). The required benzyl bromide is prepared according to methods set forth by Althuis et al., U.S. Pat. No. 4,188,495.

Method E

3-Bromo-5-(2-undecyl)anisole is reacted with magnesium in ether to form the corresponding Grignard reagent, then reacted with ethyl orthoformate and hydrolyzed to title product according to procedures set forth by Smith and Nichols, J. Org. Chem. 6, pp. 489–506 (1941).

By methods A-D, the appropriate acid chlorides, nitriles or bromomethyl compounds are converted to:

3-methoxy-5-(5-phenyl-2-methyl-1-pentyl)benzaldehyde;

3-methoxy-5-[5-(2-chlorophenyl)-1-hexyl]benzaldehyde;

3-methoxy-5-[7-(3-fluorophenyl)-3-heptyl]benzaldehyde;

3-methoxy-5-[8-(3-pyridyl)-1-octyl]benzaldehyde;

3-methoxy-5-(2S-undecyl)benzaldehyde;

3-methoxy-5-(2R-undecyl)benzaldehyde;

3-methoxy-5-(5-phenyl-2S-methyl-1-pentyl)benzaldehyde; and 3-methoxy-5-(5-phenyl-2R-methyl-1-pentyl)benzaldehyde.

By method E, aryl bromides from an earlier Preparation are converted to:

3-hydroxy-5-(2-hexyl)benzaldehyde;

3-hydroxy-5-(3-ethyl-1-pentyl)benzaldehyde;

3-hydroxy-5-(5-phenyl-1-hexyl)benzaldehyde;

3-hydroxy-5-(6-phenyl-2-hexyl)benzaldehyde;

3-hydroxy-5-[6-(4-chlorophenyl)-2-hexyl]benzaldehyde;

3-hydroxy-5-[6-(4-fluorophenyl)-2-pentyl]benzaldehyde;

3-hydroxy-5-[6-(4-pyridyl)-2-hexyl]benzaldehyde;

3-hydroxy-5-[1-(1-heptyloxy)-2-propyl]benzaldehyde; and 3-bromo-5-[2-(2-phenylethoxy)-1-propyl]benzaldehyde.

PREPARATION 20

Benzyl Methanesulfonate

Under nitrogen methylene chloride (1.4 liter), benzyl alcohol (129.6 g., 1.2 moles) and triethylamine (182 g., 1.8 moles) were combined, stirred and cooled to −5° C. in an ice-water-acetone bath. A solution of methanesulfonyl chloride (150 g., 1.31 moles) in 100 ml. of methylene chloride was added over 49 minutes, maintaining the temperature between −5° and 2° C. After stirring for 10 minutes at 0°–2° C., the reaction was diluted with 500 ml. of water, precooled to 5° C. The organic layer was separated, washed 2×500 ml. of cold water, dried over MgSO$_4$, filtered and evaporated in vacuo to yield title product as a light yellow oil [190 g.; 85%, $^1$H-NMR (CDCl$_3$) delta (ppm): 2.9 (s, 3H), 5.2 (s, 2H), 7.4 (m, 5H); R$_f$ 0.75 (CH$_2$Cl$_2$)]. This product was refrigerated until used in the next step.

PREPARATION 21

Ethyl 2S-Benzyloxypropionate

Under nitrogen, benzyl methanesulfonate (181.5 g., 0.975 mole) was combined and stirred with S-ethyl lactate (ethyl 2S-hydroxypropionate; 393 g., 3.33 moles) and the resulting solution heated on a steam bath to 94° C. over 15 minutes and held for 1.5 hours at this temperature. The reaction mixture was cooled to 45° C., poured into 2 liters of cold toluene. Water (500 ml.) was added and the mixture stirred for 5 minutes. The aqueous phase was separated and extracted with 200 ml. fresh toluene. The organic layers were combined, washed in sequence 2×500 ml. H$_2$O, 1×500 ml. saturated NaHCO$_3$, 2×500 ml. water and 1×500 ml. saturated NaCl, dried over MgSO$_4$, filtered, and evaporated in vacuo to yield crude product as an oil [228 g., 112% [alpha]$_D^{25}$ −60.8°, C=1.11 (CHCl$_3$)], which $^1$H-NMR indicated to be contaminated with ethyl lactate. Distillation in vacuo gave, after an early boiling solvent fraction 1 [25 ml., b.p. to 79° C./1.2 mm.; [alpha]$_d$−6.9°, C=1.3 (CHCl$_3$)]; fractions 2–8 [74 ml., b.p. 82° C./1.3 mm to 114° C./3 mm.; [alpha]$_D$−42.1° to −76.2°, C=1.09–1.16 (CHCl$_3$)] as a mixture of S-ethyl lactate and title product; and fractions 9–12 [57 ml.; b.p. 115° C./3 mm., 98°–100°/0.75 mm., 102°–106° C./1.0 mm.; [alpha]$_D$−80.0° to −83.7°, C=1.01–1.17 (CHCl$_3$)] of substantially pure title product. A higher boiling pot residue of 49 g. remained. A portion of fraction 10 (3 g.) was voided of traces of ethyl lactate by taking up in 100 ml. of hexane and equilibrating with 30 ml. H$_2$O. The hexane layer was separated, washed 3×30 ml. H$_2$O, dried over MgSO$_4$, filtered and concentrated to an oil [2.4 g.; R$_f$ 0.32 (6:1 hexane: ethyl acetate); [alpha]$_D^{25}$ −83.3°, C=1.13 (CHCl$_3$)].

PREPARATION 22

2S-Benzyloxy-1-propanol

Fractions 2–9 and 12 from the above distillation (106.1 g. total weight, 0.45 moles of ethyl 2S-benzyloxypropionate and 0.25 moles of S ethyl lactate) was dissolved in 100 ml. of anhydrous ethanol and the solution added dropwise to a stirred mixture of NaBH$_4$ (37.85 g., 1.0 mole) and 500 ml. of anhydrous ethanol under nitrogen over a one hour period. The temperature was maintained at 25°–30° C. during addition by cooling with a 20° C. water bath. After stirring for 20 hours at ambient temperature, the reaction mixture was cooled to 10° C. and 95 ml. of 12N HCl (1.14 mole) added dropwise over 15 minutes under a sweep of nitrogen. The resulting slurry was filtered with 100 ml. ethanol wash. The filtrate and wash were combined and concentrated in vacuo to 150 ml. The concentrate was diluted with 200 ml. of water and 300 ml. of ethyl acetate, the pH was adjusted from 1.5 to 9.0 with 50 ml. of 4N NaOH (causing precipitated solids to dissolve) and the layers were separated. The aqueous phase was washed 1×100 ml. and then 1×50 ml. of ethyl acetate. The three organic layers were combined, washed 2×150 ml. H$_2$O and then 1×150 ml. saturated NaCl, dried over MgSO$_4$, filtered, and evaporated to yield title product as an oil [50.5 g.; [alpha]$_D^{25}$+47.9, C=1.08 (CHCl$_3$); +27.736 (neat); R$_f$0.1 (CH$_2$Cl$_2$)].

PREPARATION 23

2S-Benzyloxy-1-propyl Mesylate

Under nitrogen, 2S-benzyloxy-1-propanol (49.8 g., 0.3 mole), 400 ml. of CH$_2$Cl$_2$ and triethylamine (40.5 g., 0.4 mole) were combined, stirred and cooled to −5° C. in an ice-water-acetone bath. Maintaining −5° C., methanesulfonyl chloride (37.8 g., 0.33 mole) in 30 ml. CH$_2$Cl$_2$ was added over one hour. After stirring at −5° C. for 0.5 hour, H$_2$O (200 ml. at 5° C.) was added. The layers were separated and the aqueous layer washed 1×100 ml. CH$_2$Cl$_2$. The combined organic layers were washed in sequence 1×100 ml. H$_2$O, 1×100 ml. 1N HCl, 1×100 ml. H₂O, 1×100 ml. saturated NaHCO₃ and 1×100 ml. H₂O, dried over MgSO₄, filtered, and concentrated in vacuo to yield title product as an oil [72.2 g., 98.5%; [alpha]$_D^{25}$+7.7, C=1.00 (CHCl₃); R$_f$ 0.6 (CH₂Cl₂)].

PREPARATION 24

2S-Benzyloxy-1-propyl Iodide

Under nitrogen with stirring, sodium iodide (90 g., 0.6 mole) was dissolved in one liter dry acetone. At 32° C., 2S-benzyloxy-1-propyl mesylate (71.5 g., 0.293 mole) was added. The reaction mixture was warmed to 59°–60° C. (gentle reflux) and held for 20 hours, at which time tlc indicated about 20% starting material to remain. Additional sodium iodide (30 g., 0.2 mole) was added and refluxing continued for 3 hours. The reaction was cooled to room temperature and filtered with acetone wash. The combined filtrate and wash was concentrated to 150 ml. of oily solids, diluted with 300 ml. toluene and 200 ml. H₂O, the layers separated and the aqueous phase extracted 2×100 ml. toluene. The three organic layers were combined, washed 2×200 ml. H₂O, dried over MgSO₄, filtered and evaporated to yield title product as an oil [79 g., 96%, [alpha]$_D$= +8.0°, C=1.08 (CHCl₃), ¹H-NMR (CDCl₃) delta (ppm): 1.4 (d, 3H), 3-3.6 (m, 3H), 4.6 (s, 2H), 7.35 (s, 5H)].

PREPARATION 25

Ethyl 2-Benzoyl-4S-benzyloxyvalerate

Under nitrogen, sodium hydride (50% in oil, 13.6 g., 0.283 mole) was washed with 3×200 ml. of dry hexane. To the resulting hexane wet NaH, 130 ml. dimethylformamide was added, followed by the dropwise addition of ethyl benzoylacetate (54.4 g., 0.283 mole) over 45 minutes, maintaining the temperature 28°–32° C. with a 10° C. water bath and sweeping away evolved H₂ with N₂. After stirring for 85 minutes at 25° C., 2S-benzyloxy-1-propyl iodide (78 g., 0.283 mole) was added with 40 ml. of dimethylformamide for rinse. The reaction mixture was then heated and stirred at 122°–126° C. for 2 hours (during which solids precipitated), cooled to 70° C., diluted with 350 ml. toluene and 560 ml. of ice water, and the resulting layers separated. The aqueous layer was extracted 3×150 ml. toluene. The four organic layers were combined, washed 3×150 ml. H₂O and then 1×150 ml. saturated NaCl, dried over MgSO₄, filtered and concentrated in vacuo to yield title product as an oil (90 g., 94% [alpha]$_D^{25}$+15.8°, C=1.12 (CHCl₃); R$_f$ 0.35 (6:1 hexane:ethyl acetate)].

Substitution of an equivalent amount of S-propylene oxide for 2S-benzyl-1-propyl iodide in this process and operating in a closed container (i.e. under pressure) to avoid loss of the volatile epoxide affords a method for the preparation of ethyl 2-benzoyl-4S-hydroxyvalerate.

PREPARATION 26

4S-Benzyloxy-1-phenyl-1-pentanone

Ethyl 2-benzoyl-4S-benzyloxyvalerate (89 g., 0.26 mole), ethanol (175 ml.), water (175 ml.) and KOH (85%, 51 g., 0.8 mole) were combined with stirring under nitrogen, during which the temperature rose to 45° C. The reaction mixture was heated to 79° C. under a reflux condenser and held for 18 hours. The reaction mixture was cooled to 25° C., diluted with 350 ml. of water and 300 ml. of toluene, the layers separated, and the aqueous layer washed 1×200 ml. and 2×150 ml. toluene. The organic layers were combined, washed 2×200 ml. H₂O and 1×200 ml. saturated NaCl, dried over MgSO₄, filtered and concentrated in vacuo to yield title product as an oil [45.5 g., 65%; [alpha]$_D^{25}$+21.92°, C=1.20 (CHCl₃); R$_f$ 0.55 (6:1 hexane:ethyl acetate)].

The same method is used to convert ethyl 2-benzoyl-4S-hydroxyvalerate to 4S-hydroxy-1-phenyl-1-pentanone.

PREPARATION 27

5-Phenyl-2S-pentanol

4S-Benzyloxy-1-phenyl-1-pentanone (45 g., 0.168 mole) in 150 ml. of toluene, 15 ml. of absolute alcohol and 3 drops concentrated HCl were hydrogenated over 4 g. 50% water wet 5% Pd/C at 50-60 psig and 25° C. After hydrogenating for 6 hours, an additional 4 g. catalyst was charged and hydrogenation continued for 2.5 hours, by which time three equivalents of hydrogen were consumed and there had been no uptake over the final 1.5 hour period. The catalyst was recovered by filtration. The filtrate was neutralized by stirring over a 5 cc volume of solid NaHCO₃, dried over MgSO₄, filtered and concentrated in vacuo to yield title product as an oil [22 g., 80%; [alpha]$_D^{25}$+8.63, C=1.02 (CHCl₃); R$_f$ 0.2 (6:1 hexane:ethyl acetate)]. If desired the title product was further purified by simple distillation to remove traces of tlc origin material, b.p. 90-94/0.7 mm. with nearly quantitive recovery.

By the same procedure, with uptake of two rather than three equivalents of hydrogen, 4S-hydroxy-1-phenyl-1-pentanone is converted to 5-phenyl-2S-pentanol.

We claim:

1. A compound having the formula

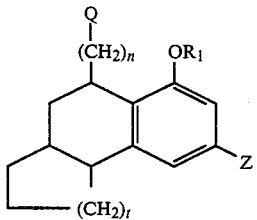

wherein n is zero, 1 or 2; t is 1 or 2, R₁ is H or (C₁–C₅)alkanoyl, Q is COR₅ or C(OR⁷)R₅R₆, where R₅ and R₆ are each H, (C₁–C₄)alkyl, phenyl or benzyl; R₇ is H, or when one or both of R₅ and R₆ are H, R₇ is H or (C₂–C₄)alkanoyl;

Z is (C₅–C₁₃)alkyl, (C₅–C₁₃)alkoxy, (C₅–C₁₃)alkoxyalkyl, (C₉–C₁₄)phenylalkyl, (C₉–C₁₄)phenylalkoxy or (C₉–C₁₄)phenylalkoxyalkyl.

2. A compound according to claim 1 wherein Z is (C₅–C₁₃)alkoxy or (C₉–C₁₄)phenylalkoxy.

3. A compound according to claim 2 wherein n is 1 and Q is CH₂OR₇.

4. A compound according to claim 3 wherein R₇ is H or acetyl.

5. A compound according to claim 4 wherein Z is OCH(CH₃) (CH₂)₄CH₃ or OCH(CH₃) (CH₂)₃C₆H₅.

6. A compound according to claim 5 having the absolute or relative stereochemical formula

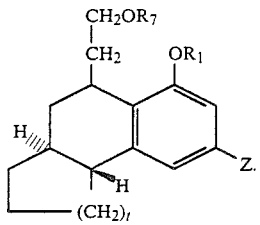

7. A compound according to claim 6 wherein Z is

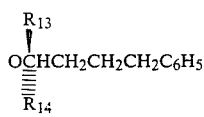

where one of $R_{13}$ and $R_{14}$ is H and the other is $CH_3$.

8. A compound according to claim 7 of the formula

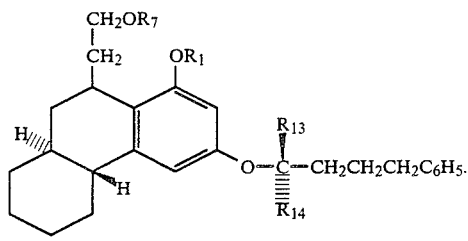

9. A compound according to claim 8 wherein $R_1$ and $R_7$ are each H.

10. The compound according to claim 9 of the formula

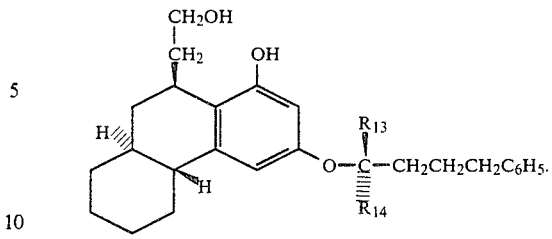

11. The compound according to claim 9 of the formula

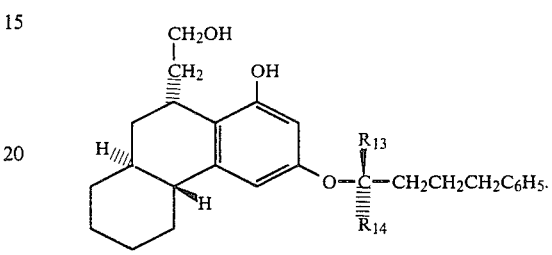

12. A method for producing analgesia in a mammalian subject which comprises orally or parenterally administering to said subject an analgesia-effective amount of a compound according to claim 1.

13. A pharmaceutical composition suitable for use as an analgesic which comprises a pharmaceutically-acceptable carrier and an analgesia-effective amount of a compound according to claim 1.

14. A method for prevention and treatment of nausea in a mammal subject to said nausea which comprises orally or parenterally administering to said mammal a compound according to claim 1 in an amount effective to prevent nausea.

15. A pharmaceutical composition suitable for use in prevention and treatment of nausea which comprises a pharmaceutically-acceptable carrier and a compound according to claim 1 in an amount effective to prevent nausea.

* * * * *